United States Patent
Wedeking et al.

(10) Patent No.: US 7,186,397 B2
(45) Date of Patent: *Mar. 6, 2007

(54) METAL COMPLEXES DERIVATIZED WITH FOLATE FOR USE IN DIAGNOSTIC AND THERAPEUTIC APPLICATIONS

(75) Inventors: Paul W. Wedeking, Pennington, NJ (US); Ruth E. Wager, Rockville, MD (US); Thangavel Arunachalam, Plainsboro, NJ (US); Kondareddiar Ramalingam, Dayton, NJ (US); Karen E. Linder, Kingston, NJ (US); Ramachandran S. Ranganathan, Princeton, NJ (US); Adrian D. Nunn, Lambertville, NJ (US); Natarajan Raju, Kendall Park, NJ (US); Michael F. Tweedle, Princeton, NJ (US)

(73) Assignee: Bracco International B.V., Amsterdam (NL)

( * ) Notice: Subject to any disclaimer, the term of this patent is extended or adjusted under 35 U.S.C. 154(b) by 1062 days.

This patent is subject to a terminal disclaimer.

(21) Appl. No.: 09/752,867

(22) Filed: Dec. 30, 2000

(65) Prior Publication Data

US 2001/0004454 A1 Jun. 21, 2001

Related U.S. Application Data

(62) Division of application No. 09/477,072, filed on Jan. 3, 2000, now Pat. No. 6,221,334, which is a division of application No. 09/080,157, filed on May 16, 1998, now Pat. No. 6,093,382.

(51) Int. Cl.
*A61K 51/00* (2006.01)
*A61M 36/14* (2006.01)

(52) U.S. Cl. .......... 424/1.73; 424/1.11; 424/9.1; 424/1.65

(58) Field of Classification Search .......... 424/1.11, 424/1.65, 1.69, 9.1, 1.73; 534/7, 10–16; 530/400, 530/403; 435/7.1
See application file for complete search history.

(56) References Cited

U.S. PATENT DOCUMENTS

| | | | |
|---|---|---|---|
| 4,639,365 | A | 1/1987 | Sherry |
| 5,055,288 | A | 10/1991 | Lewis et al. |
| 5,069,216 | A | 12/1991 | Groman et al. |
| 5,108,921 | A | 4/1992 | Low et al. |
| 5,141,739 | A | 8/1992 | Jung et al. |
| 5,248,492 | A | 9/1993 | Groman et al. |
| 5,262,176 | A | 11/1993 | Palmacci et al. |

(Continued)

FOREIGN PATENT DOCUMENTS

| | | |
|---|---|---|
| WO | WO 90/01295 | 2/1990 |
| WO | WO 90/01899 | 3/1990 |
| WO | WO 90/01900 | 3/1990 |
| WO | WO 91/07911 | 6/1991 |
| WO | WO 92/11037 | 7/1992 |
| WO | WO 96/11023 | 4/1996 |
| WO | WO 96/11712 | 4/1996 |
| WO | WO 96/36367 | 11/1996 |

*Primary Examiner*—Dameron L. Jones
(74) *Attorney, Agent, or Firm*—Kramer Levin Naftalis & Frankel LLP

(57) ABSTRACT

Diagnostic and therapeutic compositions in the form of complexes for enhancing transmembrane transport of a diagnostic or therapeutic agent and methods for their use. The complexes contain the $\alpha$, $\gamma$, or bis isomers of folate receptor-binding analogs of folate, a metal chelated by a ligand, and in one embodiment, a chemotherapeutic agent.

20 Claims, 32 Drawing Sheets

U.S. PATENT DOCUMENTS

| | | |
|---|---|---|
| 5,284,646 A | 2/1994 | Menz et al. |
| 5,314,679 A | 5/1994 | Lewis et al. |
| 5,336,506 A | 8/1994 | Josephson et al. |
| 5,342,606 A | 8/1994 | Sherry et al. |
| 5,352,432 A | 10/1994 | Menz et al. |
| 5,358,704 A | 10/1994 | Desreux et al. |
| 5,373,093 A | 12/1994 | Vallarino et al. |
| 5,399,338 A | 3/1995 | Born et al. |
| 5,416,016 A | 5/1995 | Low et al. |
| 5,478,576 A | 12/1995 | Jung et al. |
| 6,093,382 A * | 7/2000 | Wedeking et al. ......... 424/1.65 |
| 6,221,334 B1 * | 4/2001 | Wedeking et al. ......... 424/1.65 |

* cited by examiner

Binding of $^{153}$Gd-DO3A-APA-($\alpha$)-folate, $^{153}$Gd-DO3A-APA-($\gamma$)- folate or $^3$H folate to KB cells at 37°C

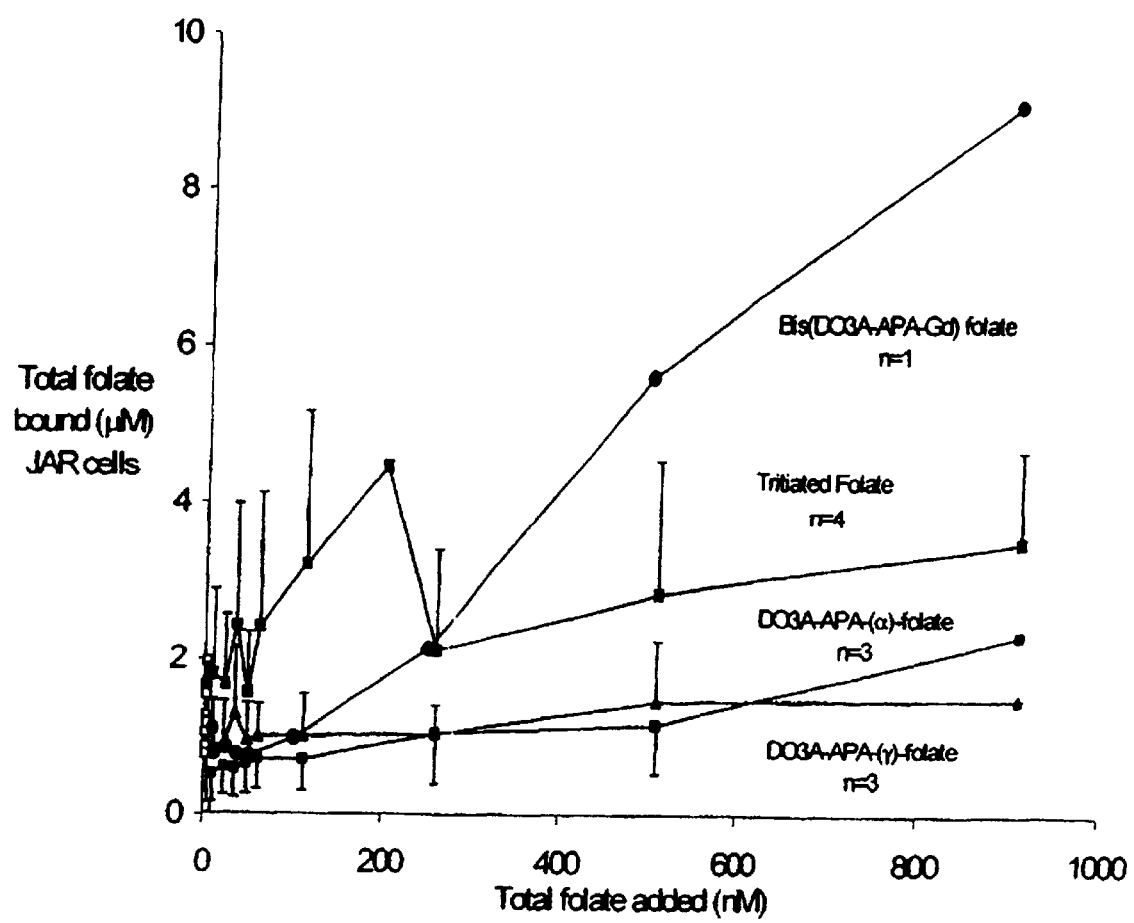

Binding of ³H-folate and alpha or gamma isomer of ¹⁵³Gd-DO3A-APA-folate to KB cells at 4°C in the presence and absence of excess folate.

Washout of $^{153}$Gd(DO3A-APA)-(α- or γ-)folate or $^{3}$H-folate from JAR cells

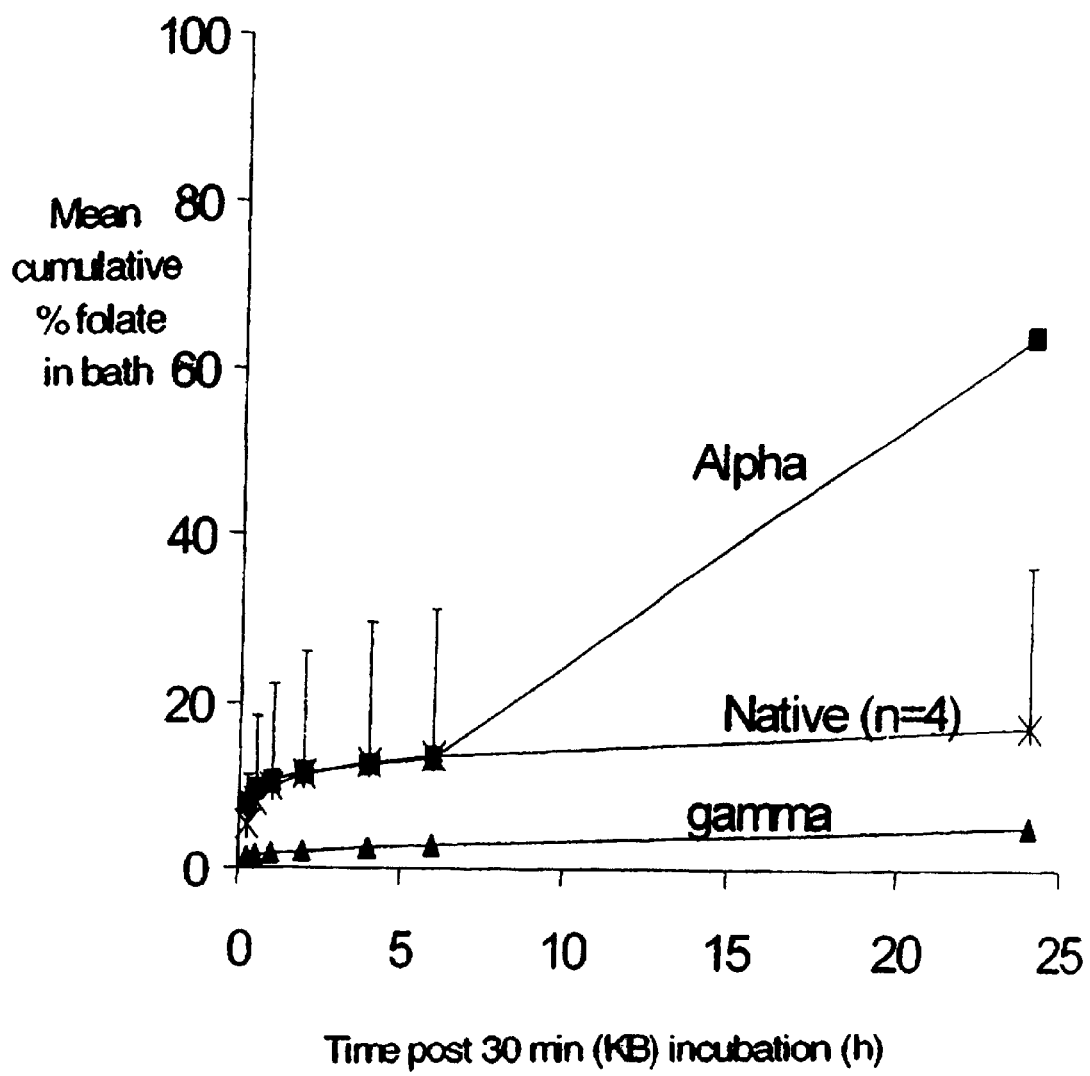

Binding of $^3$H-folate and alpha or gamma isomer of $^{99m}$Tc-Oxa-folate to KB cells at 4°C in the presence and absence of excess folate.

Exchange (with 250 nm cold folate in the medium) of folates from KB cells

Exchange (with 250 nm cold folate in the medium) of folates from JAR cells

5a

6

7          2

9a

10

15a: R=H
15b: R=CH3

16b

17a: R=H
17b: R=CH3

16a: R=H
16b: R=SO₂CF₃

15a: R=H
15b: R=CH3

20

21a: R=H
21b: R=CH3

24a: R=H
24b: R=CH₃

15a: R=H
15b: R=CH3

25

26a: R=H
26b: R=CH3

27a: R=H
27b: R=CH3

30a: R=H
30b: R=CH₃

36

46

47

48

49

50      51      52a: X=Phthalimido, 52b: X=NH$_2$

53a: X=Br
53b: X= Phthalimido

51

METAL COMPLEXES DERIVATIZED WITH FOLATE FOR USE IN DIAGNOSTIC AND THERAPEUTIC APPLICATIONS

This application is a divisional of co-pending application Ser. No. 09/477,072 filed Jan. 3, 2000, now U.S. Pat. No. 6,221,334 which in turn is a divisional of application Ser. No. 09/080,157 filed on May 16, 1998, now U.S. Pat. No. 6,093,382.

BACKGROUND OF THE INVENTION

1. Field of the Invention

The present invention relates to diagnostic and therapeutic compositions, methods of their use, and processes of their preparation.

More particularly, the invention relates to:

(a) Magnetic resonance diagnostic compositions for visualization of tissues that over-express folate binding protein, comprising ligands chelated to superparamagnetic or paramagnetic metals and coupled to folate-receptor binding ligands;

(b) Radiodiagnostic compositions for visualization of tissues, comprising ligands chelated to radioactive gamma-emitting metals and coupled to folate-receptor binding ligands;

(c) Compositions for radiotherapy or for neutron capture therapy, comprising ligands chelated to radioactive alpha or beta-emitting metals or to metals suitable for neutron capture therapy and coupled to folate-receptor binding ligands; and (d) Compositions for chemotherapy, comprising certain derivatives of folic acid coupled to a cancer chemotherapy drug through the alpha carboxylate of folic acid or coupled through both the alpha and gamma carboxylates.

2. Reported Developments

The folate-based diagnostic and therapeutic agents of the present application are designed for use in Nuclear Medicine, Magnetic Resonance Imaging (MRI), and neutron capture therapy applications. Magnetic resonance (hereinafter sometimes referred to as MR) imaging is well known and widely used by the prior art for obtaining spatial images of parts of a patient for clinical diagnosis. The image is obtained by placing the patient in a strong external magnetic field and observing the effect of this field on the magnetic properties of protons contained in and surrounding the organ or tissue of the patient. The proton relaxation times, called $T_1$ or spin-lattice or longitudinal relaxation time, and $T_2$ or spin-spin or transverse relaxation time depend on the chemical and physical environment of the organ or tissue being imaged. In order to improve the clarity of the image, a diagnostic agent is administered intravenously (hereinafter sometimes referred to as I.V.) and is taken up by the organs, such as the liver, spleen, and lymph nodes to enhance the contrast between healthy and diseased tissues.

The contrast agents used in MR imaging derive their signal-enhancing effect from the inclusion of a material exhibiting paramagnetic, ferrimagnetic, ferromagnetic or superparamagnetic behavior. These materials affect the characteristic relaxation times of the imaging nuclei in the body regions into which they distribute causing an increase or decrease in MR signal intensity. There is a need for contrast agents such as those of the present invention, that selectively enhance signal intensity in particular tissue types, as most MR contrast agents are relatively non-specific in their distribution.

Nuclear medicine procedures and treatments are based on internally distributed radioactive materials, such as radiopharmaceuticals or radionuclides, which emit electromagnetic radiations as gamma rays or photons. Following I.V., oral or inhalation administration, the gamma rays are readily detected and quantified within the body using instrumentation such as scintillation and gamma cameras. The gamma-emitting agents of the present invention are designed to selectively localize in particular targeted tissues by transmembrane transport, yielding either high signal intensity in these tissue types for imaging purposes, or high radiation dose, for radiotherapy purposes.

Transmembrane transport of exogenous molecules, such as diagnostic agents, is also known by the prior art. One method of transmembrane delivery, receptor-mediated endocytosis, is the movement of extracellular ligands bound to cell surface receptors into the interior of the cells through invagination of the membrane. This process is initiated by the binding of a ligand to its specific receptor. Folates, which are required for the survival and growth of eukaryotic cells, are taken up into cells by receptor-mediated transport after binding to folate binding protein on the cell membrane. The cellular uptake of exogenous molecules can be enhanced by conjugation of these molecules to folate. Such conjugates have been used to target folate receptors to enhance cellular uptake of exogenous molecules, including some diagnostic agents. The uptake of substances by receptor-mediated endocytosis (hereinafter sometimes termed RME) is a characteristic ability of some normal, healthy cells. RME transport systems have been found on normal macrophages, hepatocytes, fibroblasts and reticulocytes. On the other hand, conversion of normal cells into tumor cells can be associated with an increase or decrease in the activity of receptors performing RME or, sometimes, with changes in the levels of receptor expression.

The use of neutron capture therapy for the treatment of cancer is well known to those skilled in the art. Briefly the system comprises administering a target substance that emits short-range radiation when it is irradiated with neutrons. Boron-10 has traditionally been used for neutron capture therapy, but more recently Gadolinium-157, which has a very high cross section for neutrons and emits short range Auger-electrons, has been used. [Brugger, R. M. and Shih, J. A., *Strahlentherapie Und Onkologie,* 165, 153–156, 1989; Brugger, R. M. and Shih, J. A., *Medical Physics,* 19, 733–744, 1992]. Specificity is achieved by using neutrons of appropriate energy and the selective distribution of the gadolinium within the tumor tissue. In the past, neutron capture therapy has suffered from insufficient concentration of target substance in the desired cells and in the case of gadolinium, has suffered from the exclusion of the gadolinium from the inside of the cell. The use of the folate-containing gadolinium compounds of this invention is advantageous because of the large amounts of gadolinium that are specifically taken up by the desired cells. The internalization of the compounds of this invention following binding to folate binding protein is beneficial because of the short range of the Auger electrons. In addition, the gadolinium compounds of this invention can be used as MRI contrast agents that selectively target the cells that are to be treated by neutron capture therapy. The imaging data can provide the radiotherapist with spatial information beneficial for planning the radiotherapy procedure, using the same gadolinium atoms as are used as the target for the neutrons.

The following illustrative studies describe relevant properties of the folate receptor.

Folic acid or pteroyl glutamic acid is a vitamin consisting of a pteridine ring linked by a methylene bridge to a para-aminobenzoic acid moiety, which is joined through an amide linkage to a glutamic acid residue. Folic acid and folates are well absorbed from the diet primarily via the proximal portion of the small intestine. Following their absorption from the digestive system, dietary folates are rapidly reduced by dihydrofolate reductase and other enzymes to tetrahydrofolic acid and derivatives thereof.

Folates are required for the survival and growth of eukaryotic cells, so their cellular uptake is assured by at least two independent transport mechanisms. Reduced folates are internalized via a carrier-mediated low affinity ($K_m$ 1–5 µM) anion-transport system that is found in nearly all cells. Folic acid and 5-methyl tetrahydrofolate can also enter cells via a high affinity ($K_d$ values in the nanomolar range) membrane-bound folate-binding protein (hereinafter sometimes referred to as FBP) that is anchored to the cell membrane via a glycosylphosphatidylinositol (hereinafter sometimes referred to as GPI) moiety. This process has been studied in MA104 cells, where experiments have shown that 5-methyltetrahydrofolate is taken up into the cell after binding to glycosylphosphatidylinositol (GPI)-anchored FBP that has clustered in cell structures known as caveolae. The caveolae then seal the folate binding protein-folate complex off from the extracellular space and transport folate into the cell. Once inside, the folate dissociates from FBP and diffuses into the cytoplasm, where it is rapidly coupled to one or more glutamic acid residue, slowing diffusion out of the cell. The caveolae and FBP then migrate to the membrane surface for another round of folate uptake.

There are two major isoforms of the human membrane folate binding proteins, α and β. The two isoforms have ~70% amino acid sequence homology, and differ dramatically in their stereospecificity for some folates. Both isoforms are expressed in both fetal and adult tissue; normal tissue generally expresses low to moderate amounts of FR-β. FR-α is expressed in normal epithelial cells and is frequently strikingly elevated in a variety of carcinomas, with the exception of squamous cell carcinomas of the head and neck. Several papers have reported the overexpression of folate binding protein in cancer. See for example:

Ross J F, Chaudhuri P K, Ratman M, "Differential regulation of folate receptor isoforms in normal and malignant tissues in vivo and in established cell lines. Physiologic and clinical implications", Cancer, 1994, 73(9), 2432–2443;

Rettig, W, Garin-Chesa P, Beresford H, Oettgen H, Melamed M. Old L., "Cell-surface glycoproteins of human sarcomas: differential expression in normal and malignant tissues and cultured cells", Proc. Natl. Acad. Sci U.S.A., 1988, 85, 3110–3114;

Campbell I G, Jones T A, Foulkes W D, Trowsdale J., "Folate-binding protein is a marker for ovarian cancer", Cancer Res., 1991, 51, 5329–5338;

Coney L R, Tomassetti A, Carayannopoulos L, Frasca V, Kamen B A, Colnaghi M I, Zurawski V R Jr, "Cloning of a tumor-associated antigen: MOv18 and MOv19 antibodies recognize a folate-binding protein", Cancer Res. 1991, 51, 6125–6132;

Weitman S D, Lark R H, Coney L R, Fort D W, Frasca V, Zurawski V R Jr, Kamen B A, "Distribution of the folate receptor (GP38) in normal and malignant cell lines and tissues", Cancer Res., 1992, 52, 3396–3401;

Garin-Chesa P, Campbell I, Saigo P, Lewis J, Old L, Rettig W, "Trophoblast and ovarian cancer antigen LK26. Sensitivity and specificity in immunopathology and molecular identification as a folate-binding protein", Am. J. Pathol., 1993, 142, 557–567;

Holm J, Hansen S I, Hoier-Madsen M, Sondergaard K, Bzorek M, "Folate receptor of human mammary adenocarcinoma", APMIS, 1994, 102, 413–419;

Franklin W A, Waintrub M., Edwards D, Christensen K, Prendergrast P, Woods J., Bunn P A, Kolhouse J F, "New anti-lung cancer antibody cluster 12 reacts with human folate receptors present on adenocarcinoma", Int. J. Cancer, 1994, 8 (Suppl.) 89–95.

Miotti S, Canevari S, Menard S, Mezzanzanica D, Porro G, Pupa S M, Regazzoni M, Tagliabue E, and Colnaghi M I, "Characterization of human ovarian carcinoma-associated antigens defined by novel monoclonal antibodies with tumor-restricted specificity", Int. J. Cancer, 1987, 39, 297–303; and Vegglan R, Fasolato S, Menard S, Minucci D, Pizzetti P, Regazzoni M, Tagliabue E, Colnaghi M I, "Immunohistochemical reactivity of a monoclonal antibody prepared against human ovarian carcinoma on normal and pathological female genital tissues", Tumori, 1989, 75, 510–513.

Folate binding proteins are also present in normal adult oviduct epithelium and in kidney distal and proximal tubules, where they serve to prevent excessive loss of folate via the urine. Kidneys may, as a result, be a significant source of toxicity. Folic acid in high doses has been reported to be nephrotoxic and a kidney-specific tumor promoter, as it is rapidly concentrated in the kidney and precipitated in the tubules as urinary pH drops, causing obstructive nephropathy. This injury results in diffuse renal cell proliferation and hypertrophy. Rats given i.v. injections of folic acid (250 mg/kg) in 0.3 M sodium bicarbonate showed an increase in the ratio of kidney to body weight that reached 165% of control by 24 h after treatment. See for example:

Klinger E L J, Evan A P, Anderson R E, "Folic acid-induced renal injury and repair", Arch. Pathol. Lab. Med. 1980, 104, 87–93;

Hsueh W. Rostorfer H H, "Chemically induced renal hypertrophy in the rat", Lab. Invest. 1973, 29, 547–555; and Dong L. Stevens J L, Fabbro D, Jaken S, "Regulation of Protein Kinase C isozymes in kidney regeneration", Cancer Res. 1993, 53, 4542–4549.

Overexpression of FBP by a number of different tumors has led a number of investigators to explore its potential as a delivery system for toxins or poorly permeable compounds coupled to folic acid and as a means to increase selective delivery of antifolate drugs such as methotrexate to tumors. The amount of FBP on the membrane of ovarian cancer cells is high ($1 \times 10^6$ molecules/cell). IGROV cells in culture can bind $^3$H folic acid at a level of 10–12 pmol/$10^6$ cells; MA104 cells bind 1–2 pmol folic acid/$10^6$ cells. FBP has a very high affinity for folic acid and some of its reduced folate cofactors ($K_d$~1–10 nM); this presumably favors folate uptake at the usual folate concentrations that exist in vivo (5–50 nM). The recycling rate for the folate binding protein (in vitro) has been reported to range from ~30 min in MA104 cells to 5 hr in L1210 cells. Several antifolate drugs have been shown to bind to FBP; these compounds, of which methotrexate is characteristic, have been used to antagonize the growth of cancer cells. See, for example:

Orr R B, Kamen B A, "UMSCC38 cells amplified at 11q13 for the folate receptor synthesize a mutant nonfunctional folate receptor", Cancer Res. 1994, 54, 3905–3911;

Anthony A C, "The biological chemistry of folate receptors", Blood, 1992, 79, 2807–2820; and Spinella M J, Brigle K E, Sierra E E, Goldman, I D, "Distinguishing between folate receptor-α-mediated transport and reduced folate carrier-mediated transport in L1210 leukemia cells", J. Biol. Chem., 1995, 270, 7842–7849.

These studies indicate an essential fact necessary to distinguish between normal cells and tumor cells when delivering pharmaceutical or diagnostic agents into a patient using folates to be internalized by FBP. FBP levels are low in many normal tissue types while, in comparison, FBP levels are high in many tumor cells. This difference between the folate receptor levels allows selective concentration of pharmaceutical or diagnostic agents in tumor cells relative to normal cells, thereby facilitating treatment or visualization of tumor cells.

In culture, cells were successfully targeted through FBP using folate-conjugated protein toxins that would not normally penetrate the cell membrane through diffusion, as well as with folate-derivatized drug/antisense oligonucleotide-carrying liposomes. See, for example:

Leamon C P, Low P S, "Cytotoxicity of momordin-folate conjugates in cultured human cells", J. Biol. Chem., 1992, 267, 24966–24967;

Leamon C P, Paston I, Low P S, "Cytotoxicity of folate-pseudomonas exotoxin conjugates towards tumor cells", J. Biol. Chem., 1993, 268, 3198–3204;

Lee R J, Low P S, "Delivery of liposomes into cultured KB cells via folate receptor-mediated endocytosis", J. Biol. Chem., 1994, 269, 3198–3204;

Wang S, Lee R J, Cauchon G, Gorenstein D G, Low P S, "Delivery of antisense oligonucleotides against the human epidermal growth factor receptor into cultured KB cells with liposomes conjugated to folate via polyethyleneglycol", Proc. Natl. Acad. Sci U.S.A., 1995, 92, 3318–3322; and Wang S, Lee R J, Mathias C J, Green M A, Low P S, "Synthesis, purification and tumor cell uptake of Ga-67-Deferoxamine-folate, a potential radiopharmaceutical for tumor imaging", Bioconj. Chem., 1996, 7, 56–63.

The prior art has spent considerable energy in studying folate binding protein as a potential target for delivery of exogenous molecules into cells that express folate binding protein, as further illustrated hereunder.

U.S. Pat. No. 5,416,016 and WO 96/36367 (Low et al.) are directed to a method for enhancing transmembrane transport of exogenous molecules and disclose such delivery wherein the method comprises: contacting a membrane of a living cell with a complex formed between an exogenous molecule and a ligand of folic acid and folate analogs to initiate receptor-mediated transmembrane transport of the ligand complex. The exogenous molecules include a large variety of compounds, peptides, proteins and nucleic acids, analgesics, antihypertensive agents, antiviral agents, antihistamines, cancer drugs, expectorants, vitamins, plasmids and diagnostic agents.

The synthetic methods described in these documents were not regioselective, and mixtures containing folic acid coupled to the exogenous molecule through either the α- or γ-carboxylate of folate are expected to form. In the process disclosed in U.S. Pat. No. 5,416,016 these mixtures were not separated.

WO 96/36367 distinguishes between the two isomers of DF-folates, i.e., those where deferoxamine is coupled to the folate moiety through the α- or through the γ-carboxyl group of folate, based on their competition with free folate for the cell surface FBP: it was found that the ax-conjugate was unable to compete with free folate for the cell surface FBP. In a comparative test a 50% decrease in bound [$^3$H] folic acid was observed in the presence of an equimolar amount of the DF-folate (γ) conjugate, while the DF-folate (α) isomer displayed no ability to compete with the radiolabeled vitamin.

Wang et al., supra, studied the uptake of $^{67}$Ga-deferoxamine-folate into KB tumor cells (a human nasopharyngeal epidermal carcinoma cell line that greatly overexpresses the folate binding protein) as a potential radiopharmaceutical. When 0.15 μCi (100 pmol) of $^{67}$Ga-DF-folate (deferoxamine coupled to folic acid via the γ-carboxylate of folate) was incubated with monolayers of KB cells, the final % uptake of the compound by the KB cells was 32% of the applied radioactivity. The compound had very low non-specific binding as indicated by very low activity levels bound to a receptor-negative cell line control.

Wang et al. subsequently published another report* stating that folic acid derivatives that are modified at the alpha carboxylate have no affinity for cell surface folate receptors. They reported the preparation of FITC-EDA-folate derivatives containing a fluorescein moiety (FITC) linked to folate through either the α- or γ-carboxylate of folate (via an ethylenediamine [EDA] spacer). The two isomers were incubated with KB cells that overexpress FBP. The cells were then washed to remove unbound compound and assayed for cell-associated fluorescence. The γ-isomer of FITC-EDA-folate showed half maximal binding to KB cells at a concentration of 1.6 nM (binding comparable to native folate), but the α-isomer of FITC-EDA-folate had "virtually no affinity for the cell surface receptors".

*Wang, Susan; Luo, Jin; Lantrip, Douglas A.; Waters, David J.; Mathias, Carla J.; Green, Mark A.; Fuchs, Philip L.; Low, Philip S. Design and Synthesis of [$^{111}$In]DTPA-Folate for Use as a Tumor-Targeted Radiopharmaceutical. Bioconjugate Chem. (1997), 8(5), 673–679.

The folate-based agents of the present application were designed for use in nuclear medicine, neutron capture therapy, or MRI applications. Based on the teachings in WO96/36367 that only folate adducts coupled to exogenous molecules through the gamma carboxylate of folate are recognized by FBP, we devised regiospecific syntheses for the preparation of these folate conjugates, rather than using the non-regiospecific methods used by others. The conjugates prepared by these regiospecific routes contained metal chelating ligands coupled to folate through its gamma carboxylate. The corresponding alpha isomers were prepared for use as negative controls. Surprisingly, when the ability of the alpha and gamma isomers to bind to FBP in tumor cells in vitro was compared, the alpha isomers (our "negative" controls) bound to FBP to the same extent as the gamma isomers in a variety of in vitro studies (vide infra). This result was surprising in light of the reports of Wang et al. Also surprising was our subsequent finding that folate compounds derivatized with metal chelates at both the alpha and gamma carboxylate of folate (bis derivatives) were also able to bind to FBP.

We also performed studies with the alpha and gamma isomers in tumor-bearing animals, where ability of the alpha isomers to localize in the tumors was surprisingly found to be equal to or greater than that observed with the corresponding gamma conjugates. In addition, the clearance behavior of the two isomers was compared, both in vivo and in vitro. As discussed in greater detail later, the urinary clearance of the alpha isomers from the body was significantly and unexpectedly higher than that observed with the corresponding γ-isomer or with $^3$H folate. This may be an advantage for some nuclear medicine and radiotherapy applications for these compounds, because retention in non-target organs causes higher radiation dose to the patient and lower target to background ratios. Compounds that are more rapidly excreted from the body provide an improved margin of safety.

We have also discovered that the alpha isomers of the folate conjugates of the present invention also show unexpectedly faster clearance from cells in vitro. Studies were performed to compare the clearance of metal complexes coupled to the γ- or α-carboxylate of folates or to both the α- and γ-carboxylates of folates (hereinafter sometimes termed bis derivatives) from KB and JAR cells. We obtained the surprising finding that the clearance rate of the α isomer and of the bis isomer from KB and JAR cells is significantly faster than that of the corresponding γ isomer or of $^3$H folate.

Based on this surprising discovery we have also found that the clearance rate of folate-based diagnostic agents designed for use in nuclear medicine or MRI applications can be varied or tailor-made by using various proportions of the α-isomer, the bis isomer and γ-isomer of such diagnostic agents. In addition to tailor-making the rate of clearance from certain organs, such as the kidney, liver, brain, liver, kidneys and from various tissues such as tumors that over-express folate binding protein, the use of chelating agents chosen for the compounds of the present invention provides a greater margin of safety against the toxicity of the metal used in the chelates.

Experiments from our laboratories on the cellular uptake of monomeric folate conjugates of Gd chelates designed for use in MR applications indicate that structural modifications that bring about an increase the intensity of the MR signal are advantageous, as the signal intensity obtainable with this technique is determined by the quantity of paramagnetic or superparamagnetic metal that can be localized in the target tissues. This is, in turn, limited by the quantity of folate binding protein present in those tissues. The desired increase in signal intensity could be achieved by attaching multimeric Gd chelates to a single folate residue and/or by the use of enhanced relaxivity Gd chelates, that are, as a result of their structure, expected to provide higher intrinsic signal intensity per Gd atom. Based on these observations the following concepts are presented for the design of new monomeric and multimeric folate conjugates of Gd chelates in order to enable MR imaging of tumors and other tissues that over-express the folate binding protein.

SUMMARY OF THE INVENTION

In accordance with the present invention, diagnostic and therapeutic compositions, methods for use, and processes for their preparations are provided. More particularly, the invention is directed to the following medical/pharmacological diagnostic and therapeutic areas of the art.

a) MR Diagnostic Composition for Visualization of Tissues that Over-express FBP using MRI The composition comprises macrocyclic and non-macrocyclic ligands chelated to superparamagnetic or paramagnetic metals and selectively coupled to folate-receptor binding ligands through the alpha, or both the alpha and gamma carboxylate of the folate-receptor binding ligand. Polyaza macrocyclic ligands with enhanced relaxivity properties and compounds that contain more than one Gadolinium per folate are especially preferred. Derivatives of folic acid and of methotrexate (MTX) are included in the composition and use of the present invention.

Polyaza macrocyclic ligands chelated to superparamagnetic or paramagnetic metals and coupled to folate-receptor binding ligands through the gamma carboxylate of folate are also included in the composition and use of the present invention. Enhanced relaxivity ligands and ligands that contain more than one Gd per folate are especially preferred. Derivatives of folic acid and of methotrexate (MTX) are included in the composition and use of the present invention.

b) Radiodiagnostic Composition for Visualization of Tissues using Nuclear Medicine Techniques The composition comprises:

macrocyclic and non-macrocyclic ligands chelated to radioactive gamma-emitting metals and coupled to folate-receptor binding ligands through either the alpha, or both the alpha and gamma carboxylate of the folate-receptor binding ligand; and selected macrocyclic and non-macrocyclic ligands chelated to radioactive gamma-emitting metals and coupled to folate-receptor binding ligands through the gamma carboxylate of the folate-receptor binding ligand. Both derivatives of folic acid and of methotrexate (MTX) are included for use in the composition.

c) Composition for Radiotherapy

The composition comprises:

macrocyclic and non-macrocyclic ligands chelated to radioactive alpha or beta-emitting metals that are coupled to folic acid receptor binding ligands through the alpha carboxylate or through both the alpha and gamma carboxylate of the folate-receptor binding ligand, and selected ligands chelated to radioactive alpha or beta-emitting metals and coupled to folate-receptor binding ligands through the gamma carboxylate of the folate-receptor binding ligand. Both derivatives of folic acid and of methotrexate (MTX) are included for use in the composition.

In particular embodiments of compositions (b) and (c) the invention is directed to a radio-diagnostic or radiotherapeutic agent comprising a chelated radioactive metal complexed with a folate receptor-binding ligand, which on administration to a patient is capable of enhancing the transport of the radioactive metal across the membrane of living cells, and of beneficially affecting the biodistribution thereof, thereby facilitating visualization or radiotherapy of the part of the body being examined by nuclear medicine diagnostic or radiotherapy techniques. A suitable radiotherapeutic composition according to the invention comprises, as the active ingredient, a folate-metal chelate derivative that bears an alpha- or beta-emitter that is suitable for radiotherapy. Suitable radionuclides for radiotherapy are e.g. those that are listed in "Radionuclides for Therapy", ed. P. Schubiger and P. H. Hasler, 1986.

In particular embodiments of composition a) the invention is directed to a paramagnetic diagnostic agent comprising a chelated paramagnetic metal conjugated to a folate receptor binding ligand, which on administration to a patient is capable of enhancing the transport of the paramagnetic metal across the membrane of living cells, and beneficially affecting the biodistribution thereof, thereby facilitating visualization of the part of the body being examined by Magnetic Resonance Imaging diagnostic techniques. A second embodiment of this invention comprises a method for radiotherapy by neutron capture techniques, comprising administering to a patient said composition, wherein the metal is gadolinium and, after localization in the desired tissues, irradiating said tissues with neutrons to achieve emission of Auger electrons by the gadolinium to the extent that the desired tissue is damaged.

d) Composition for Chemotherapy

The composition comprises: derivatives of folic acid (but not methotrexate) coupled to a cancer-chemotherapy drug through the alpha carboxylate of folic acid, or coupled through both the alpha and gamma carboxylate.

In a particular embodiment of the composition, the invention is directed to a chemotherapeutic agent comprising a chemotherapeutic compound complexed with a folate receptor-binding ligand through its alpha carboxylate functionality, which on administration to a patient is capable of enhancing the transport of the chemotherapeutic agent across the membrane of living cells, and decreasing the uptake to non-target organs thereby facilitating treatment of the tumor being targeted.

In all of these inventions, unmetallated ligand may be coinjected with the metal complexes of the ligand to affect the biodistribution of the metal complex in a useful way such as enhanced clearance.

BRIEF DESCRIPTION OF THE DRAWINGS

FIG. 1A shows binding of $^{153}$Gd-folates or $^3$H folate to JAR cells at 37° C.;

FIG. 3A shows washout of $^{153}$Gd(DO3A-APA)-($\alpha$- or $\gamma$-)folate or $^3$H-folate from KB cells;

FIGS. 7, 7A and 7B show the synthetic scheme for the preparation of the folic acid bis(DO3A-APA) conjugate 14;

FIGS. 11 and 11A show the synthetic scheme for the preparation of the triflyloxy mixedester 20;

FIGS. 13 and 13A show the synthetic scheme for the preparation of the alkylating agent 25;

DETAILED DESCRIPTION OF THE INVENTION

Figure 1:
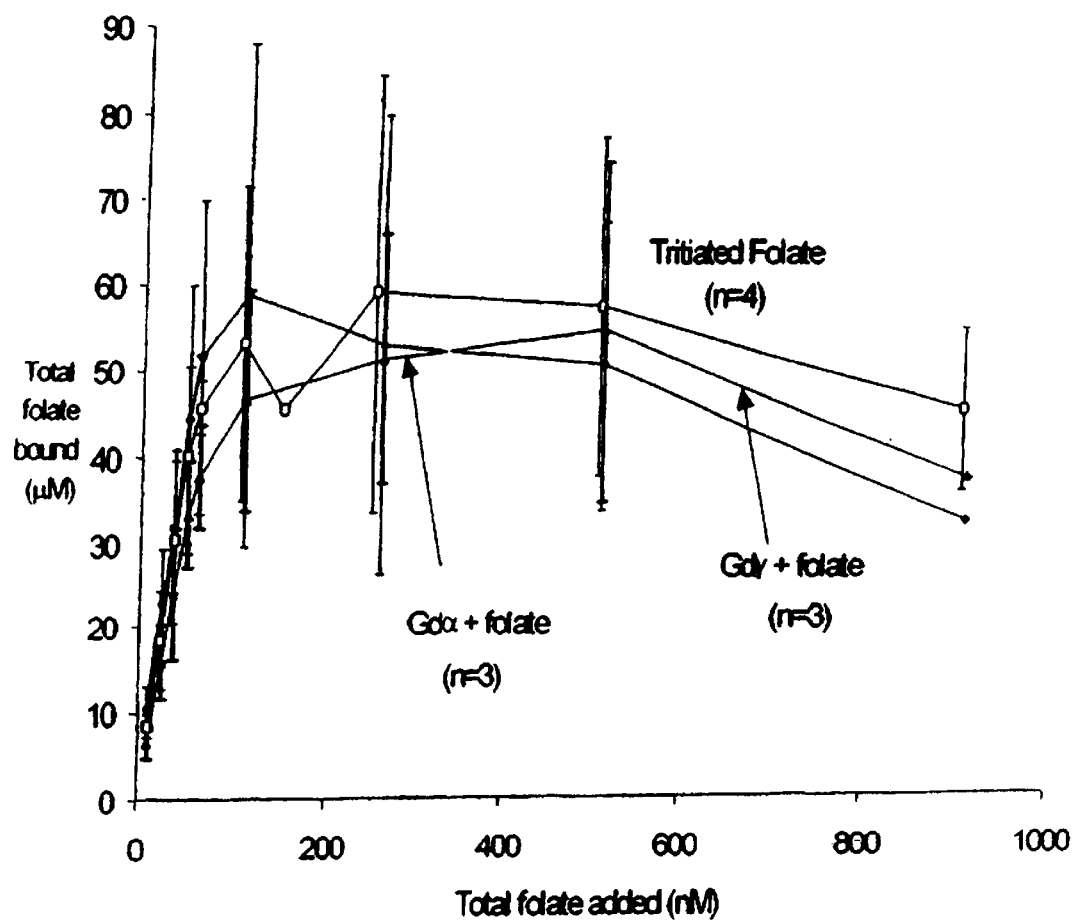
FIG. 1 shows binding of $^{153}$Gd-DO3A-APA-($\alpha$)-folate, $^{153}$Gd-DO3A-APA-($\gamma$)-folate or $^3$H folate to KB cells at 37° C.

1. General Description of the Folate Conjugates

Compounds of the present invention include derivatives of folic acid and methotrexate. The structure of folic acid is shown as FIG. Ia. Monomeric folic acid derivatives of the present invention are shown as FIG. Ib. Monomeric methotrexate derivatives of the present invention are shown as FIG. Ic.

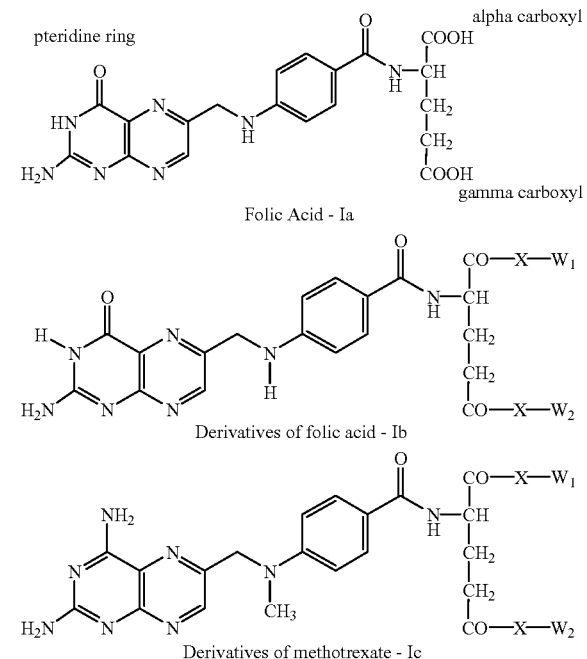

In these structures, each X may independently be —O—, —S—, —NR—, or —NH—. The group $W_1$ is attached via X to the alpha carboxylate of the folic acid or methotrexate derivative; the group $W_2$ is attached at the corresponding gamma carboxylate. Metal chelating ligands (K) and their optional chelated metals (M) and any linking groups needed to couple these chelates to the folate-receptor binding moiety can be attached as part of $W_1$ (alpha derivatives), $W_2$ (gamma derivatives) or both $W_1$ and $W_2$ (bis derivatives). Compounds that are derivatized at $W_1$ (alpha and bis derivatives) are preferred.

Several structural variations are possible with this formulation. For example, folate-receptor binding ligands of the present application comprising a single folate-receptor binding residue that is conjugated through its alpha carboxylate via an optional linking group (A)p to one metal-chelating ligand ($K_1$) that is optionally chelated to one metal ($M_1$) could be described by the general formula shown below.

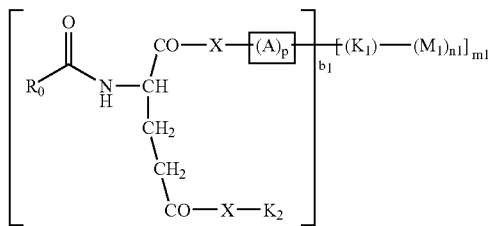

wherein $R_0$ is a folate-receptor binding residue of formula and the dashed line indicates the point of attachment of R.

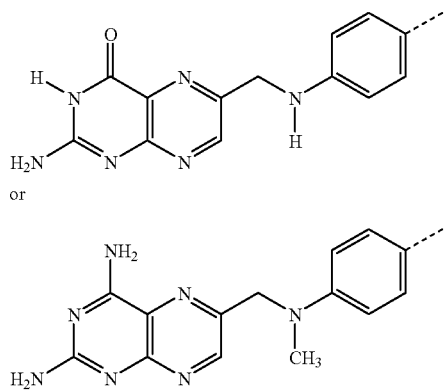

$K_1$ is a metal chelating ligand radical that is coupled to the remainder of the molecule via a linking group (A)p;
Each X is independently —O—, —S—, —NH— or —NR—;
$K_2$ is —H, -alkyl, -alkenyl, -alkynyl, -alkoxy, -aryl, -alkyl, —CON(R2)2, -glutamate, -polyglutamate;
$M_1$ is a metal, $n_1$ is 0 or 1 (0=metal absent, 1=metal present);
$b_1$ is 1 [1 receptor binding residue per chelating ligand radical $K_1$]
$m_1$ is 1 [one chelating ligand per linking group (A)p]
If the gamma carboxylate of this compound was then also derivatized with a second metal chelating group ($K_5$) and chelated metal ($M_5$), a bis derivative of the structure below is formed:

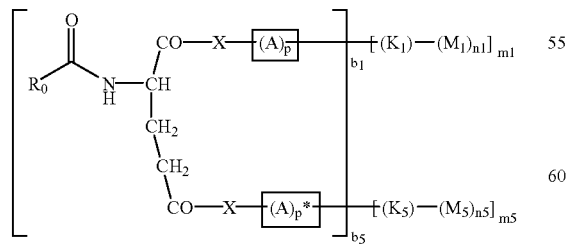

wherein $n_1$, $n_5$, $b_1$, $b_5$, $m_1$, and $m_5$ are all equal to 1.
If a single metal-chelating ligand $K_1$ is derivatized with 2 side arms, each of which is coupled to a different folate receptor binding residue through its alpha carboxylate, a different sort of bis compound is formed, wherein $n_1$ and $m_1=1$ and $b_1=2$, as shown schematically below:

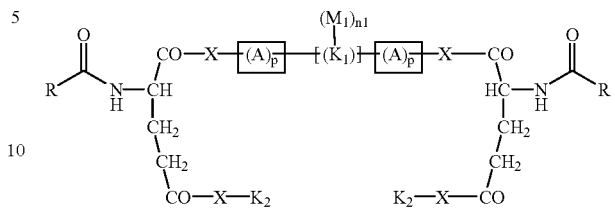

The alpha and alpha/gamma (bis) derivatives of formula II of the present application are generally defined as given below. In this definition, derivitization at the alpha position by a chemotherapeutic drug, rather than a metal-chelate is also considered.

A folate-receptor binding ligand comprising one or more folate-receptor binding residues, at least one of which is conjugated through its alpha carboxylate via an optional linking group to
(i) one or more macrocyclic or non-macrocyclic metal-chelating ligand radicals that are optionally chelated to paramagnetic, superparamagnetic, radioactive or non-radioactive metals capable of either being detected outside the body by imaging means for diagnosis or capable of providing a therapeutic or radiotherapeutic effect; or
(ii) a chemotherapeutic drug
wherein said folate receptor binding ligand has the structure of formula II:

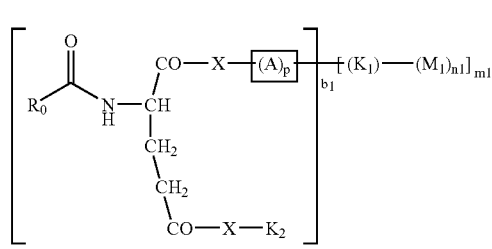

wherein $R_0$ is a folate-receptor binding residue of formula:

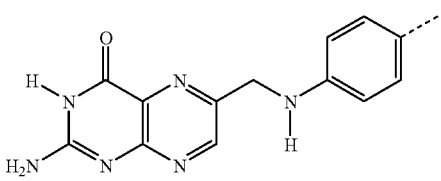

or

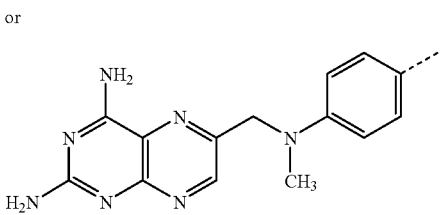

each X is independently —O—, —S—, —NH—, or —$NR_1$—;
n1 is 0 or 1;
b1 is 1 to 3;

m1 is 1 to 81;

each $K_1$ is independently
(a) a macrocyclic or non-macrocyclic metal-chelating ligand radical that is optionally chelated to a paramagnetic, superparamagnetic, radioactive or non-radioactive metal $M_1$, or
b) a chemotherapeutic drug;

—$K_2$ is —H, -alkyl, -alkenyl, -alkynyl, -alkoxy, -aryl, -alkyl, —$CON(R_2)_2$, -glutamate, -polyglutamate, or —$K_3$;

—$K_3$ is

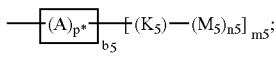

wherein
—$K_5$ is either
(a) a macrocyclic or non-macrocyclic metal-chelating ligand that is optionally chelated to a paramagnetic, superparamagnetic, radioactive or non-radioactive metal $M_5$, or
(b) a chemotherapeutic drug;

n5 is 0 or 1;
b5 is 1 to 3;
m5 is 1 to 81;

—(A)p— and —(A)p*— are each independently optional linkers comprising a straight or branched chain wherein the moieties "A" are the same or different and selected from the group consisting of: —$CH_2$—, —$CHR_3$—, —$CR_4R_5$—, —CH═CH—, —CH═$CR_6$—, >$CR_7$—$CR_8$<, —C═C—, —$CR_9$═$CR_{10}$—, —C≡C—, -cycloalkylidene-, -cycloalkenyl-, -arylidene-, -heterocyclo-, carbonyl (—CO—), —O—, —S—, —NH—, —HC═N—, —$CR_{11}$═N—, —$NR_{12}$—, —CS—,

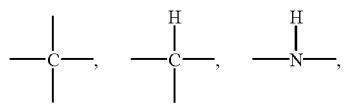

and
p and p* are independently 0 to 24, or
—X—[(A)]p— and —X—[(A)p]*— may each independently be the group —Q— wherein —Q— is —[C(R')(R")]$_{s1}$—[C(t)($R_{21}$)]$_{s2}$—[C($R_{22}$)($R_{23}$)]$_{s3}$—$X_3$—Y—$X_4$—; wherein
each s1, s2, s3, and s4 is independently 0 to 2;
each $X_3$, $X_4$, $X_5$, and $X_6$ is independently a single bond, —O—, —S—, or —N($R_{24}$)—;
Y is a single bond, —C($R_{25}$)($R_{26}$)—, or Y1 wherein, Y1 is —C(═$X_5$)—$X_6$—W—, wherein
W is a single bond, -alkylidene-, -cycloalkylidene-, -arylidene-, -alkenylidene-, or -alkynylidene-, whose carbon atoms may or may not be substituted;
t is H, $R_{27}$, —C(O)$OR_{28}$, —P(O)($OR_{29}$))OH, —P(O)($OR_{30}$))$OR_{31}$, —P(O)($OR_{32}$)$R_{33}$, —P(O)(OH)$R_{34}$—C(O)N($R_{35}$)($R_{36}$), or —C(O)NH($R_{37}$);
each R' and R" is independently a single bond, H, alkyl, alkoxy, cycloalkyl, hydroxyalkyl, aryl, or heterocyclo, each of which is optionally substituted,
each $R_3$ through $R_5$, $R_7$, $R_8$, $R_{21}$ through $R_{23}$, and $R_{25}$ through $R_{27}$ is independently H, alkyl, alkoxy, halogen, hydroxy, cycloalkyl, hydroxyalkyl, aryl, or heterocyclo, each of which is optionally substituted;
each $R_1$, $R_2$, $R_6$, $R_9$ through $R_{12}$, $R_{24}$, and $R_{28}$ through $R_{37}$ is independently H, alkyl alkenyl, cycloalkyl, aryl, a 5- or 6-membered nitrogen or oxygen containing heterocycle;

or a salt thereof.

The compounds described above are all derivatized at the alpha position of the folate receptor binding residue, as they all contain at least one moiety $K_1$ (wherein $K_1$ is a macrocyclic or non-macrocyclic metal-chelating ligand that optionally contains a paramagnetic, radioactive or non-radioactive metal, or is a chemotherapeutic drug). Alternatively, for selected metal chelating group(s) and structural motifs, the metal chelate(s) may be placed only at the gamma position. In these cases, $W_1$ of formula Ib or Ic can be a group such as H, alkyl, alkenyl, alkynyl, alkoxy, aryl, alkyl-$CON(R_3)_2$, glutamate or polyglutamate.

The nature of the linking side chain (A)p can be varied. For both folic acid and methotrexate derivatives of the present application, —(A)p and/or —(A)p* are optional linkers that can be any chemical moiety which serves to physically distance, or otherwise isolate, the metal-chelating ligand or chemotherapeutic agent from the rest of the folate binding group. If p=0, then $K_1$ or $K_2$ will be directly linked to X. If p=≧1, then A, or the various A units can form a straight or branched chain, and can be derivatized with one or with multiple metal chelating groups. It is understood that p can be any convenient value depending upon the design choices for the desired complex. Preferably, p is ≦24 and most preferably p≦10.

The compounds of the present application are used for the preparation of diagnostic, therapeutic or radiotherapeutic compositions used for visualization, therapy or radiotherapy of tissues or organs that overexpress folate-binding protein. Said compositions comprising:
a) a pharmaceutically acceptable carrier; and
b) a folate-receptor binding ligand comprised of one or more folate-receptor binding residues each of which is conjugated through at least one of its carboxylate moieties via an optional linking group to either a) one or more polydentate macrocyclic or non-macrocyclic metal-chelating ligand residues that are optionally chelated to radioactive or non-radioactive metals capable of either being detected outside the body by imaging means for diagnosis or capable of providing a therapeutic or radiotherapeutic effect; or b) a chemotherapeutic drug.

The metal chelating groups can be either macrocyclic or non-macrocyclic multidentate metal chelating ligands, and the structure of these ligands and the metals that are chelated to them may be varied depending on the use envisioned for them. For compounds of the present application that are used for Magnetic Resonance Imaging applications, chelating polyaza macrocyclic ligands that form stable compounds with superparamagnetic or paramagnetic metals, and chelating ligands that provide enhanced relaxivity properties (vide infra) are preferred. For such applications, gadolinium is the preferred metal.

Novel dendrimeric structures that contain multiple metal chelating groups can be envisioned that are especially useful for therapeutic or radiotherapeutic applications where it is useful to deliver a large quantity of the chelated metal or therapeutic drug that is used for visualization or therapy or radiotherapy into the targeted tissue. For example, com pounds which have the general structure depicted by formula VII,

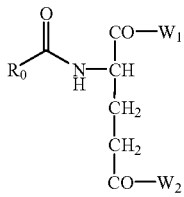

VII wherein $R_0$ is a folate-receptor binding residue of formula:

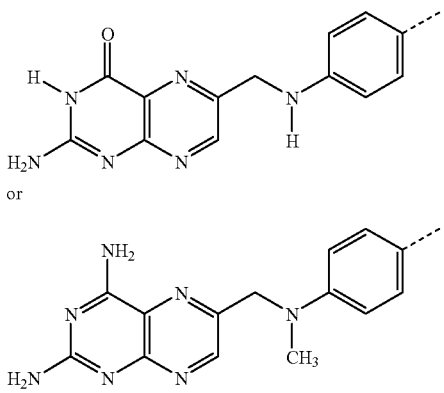

or dendrimeric structures could be prepared such that $W_1$ or $W_2$ contains multiple metal chelating groups. For example, if either $W_1$ or $W_2$ or both contained a radical of formula VIIIc:

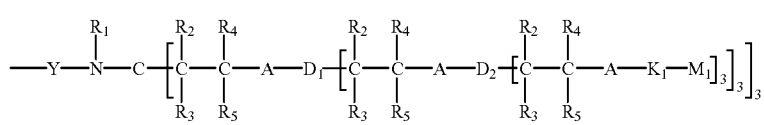

VIIIc wherein $K_1$ is a metal chelating ligand radical and $M_1$ is a metal ion, the resulting dendrimeric complex could be used to deliver high concentrations of gadolinium metal to cells that express high levels of folate binding protein, for use in magnetic resonance imaging applications or for subsequent neutron capture therapy. Similarly, if derivatized with metal chelates that bind radiotherapeutic metal isotopes, such compounds could be used to deliver high concentrations of alpha- or beta-emitting radionuclides for radiotherapy applications.

Several specific variations of these structures and others are described further below, wherein the nature of the metal-chelating groups, metals and linking groups are selected to fine-tune the properties of the compound to its intended use.

2. Detailed Description of the Macrocyclic Polyaza Ligands and their Folate Conjugation The polyaza macrocyclic compounds described below can be used for the visualization, therapy or radiotherapy of tissues or organs that overexpress folate-binding protein, depending upon what metal is used. If the compounds are derivatized with a paramagnetic metal such as gadolinium (Gd), they may be used as contrast agents for MRI techniques, after selective uptake of these compounds in tissues that overexpress folate binding protein.

Experiments from our laboratories on the cellular uptake of monomeric folate conjugates of Gd chelates using KB cells (a cell line that overexpresses FBP) indicated that obtaining adequate signal intensity in Magnetic Resonance Imaging experiments with these targeted imaging agents was very challenging, and that it was an advantage to make modifications that caused a significant increase in signal intensity. This desired increase in signal intensity could be achieved by a) attaching multiple Gd chelates to a single folate residue and/or by b) the use of enhanced relaxivity Gd chelates, which are expected to provide higher intrinsic signal intensity per Gd atom. The use of more than one folate residue per molecule also appears to be propitious based on the work of E. C. Wiener et al., Investigative Radiology, 1997, 32, 748–7544, who estimated that greater than ~10 gadolinium atoms per folate would be required for successful contrast enhancement in magnetic resonance imaging.

Based on these observations, the following concepts are presented for the design of new monomeric and multimeric folate conjugates of Gd chelates in order to enable MR imaging of tumors that over-express the folate binding protein. Said chelates can also be used in radiodiagnostic and radiotherapeutic techniques, if a suitable radioactive metal is substituted for gadolinium.

A) General Structures for Monomeric and Multimeric Polyaza-macrocyclic Ligands Conjugated to Folate Moieties The structures disclosed are further modifications of ligand motifs that have been demonstrated to possess enhanced relaxivity as discussed in our co-pending applications WO 95/31444 (Nov. 23, 1995), Ser. No. 08/010,909 (Jan. 29, 1993), U.S. Pat. Nos. 5,573,752, and 5,358,704. The aim of making the modifications is to enable conjugation of such enhanced relaxivity ligands to targeting vectors such as folate receptor binding compounds. The relaxivity of a paramagnetic compound is a measure of its signal enhancing effect when used as a contrast agent for MRI. Enhanced relaxivity compounds provide a stronger signal enhancing effect per molecule than can be obtained with the typical relaxation agents that are used for contrast enhancement. We have found that certain macrocyclic metal-chelating ligand motifs, when chelated to paramagnetic metals such as gadolinium, provide an unexpectedly strong signal-enhancing effect. If such enhanced relaxivity chelates are incorporated into a compound that targets a particular tissue such as the folate receptor, localization at the target results in a higher signal intensity than can be obtained if the comparable compound were derivatized with normal chelates for Gd, such as DTPA.

The amine-thiocarboxylate and carboxylate-containing macrocycles depicted by formula VIa below are conjugatable enhanced relaxivity motifs that can be used for coupling to targeting vectors such as folate. These intermediates are an integral part of this invention, and can be used to prepare conjugates that contain one, or preferably greater than one metal chelate per folate residue. Such multimeric compounds are particularly useful, as multiple paramagnetic metals are localized at the target tissue upon binding of a single folate receptor binding moiety. The presence of multiple paramagnetic metal chelates per molecule, coupled with the enhanced relaxivity properties provided by each of these metal chelates, should significantly improve the sensitivity of magnetic resonance imaging agents designed for the detection of folate-receptor positive tissue.

(i) Intermediate Ligands Bearing Free Carboxylate, Thiocarboxylate or Amino Functions for Conjugation to Folate Moieties The conjugatable polyaza macrocyclic ligands are depicted by formula VIa. These intermediates contain at least one free amine, carboxylate or thiocarboxylate functionality that can be used for conjugation to targeting vectors such as folate.

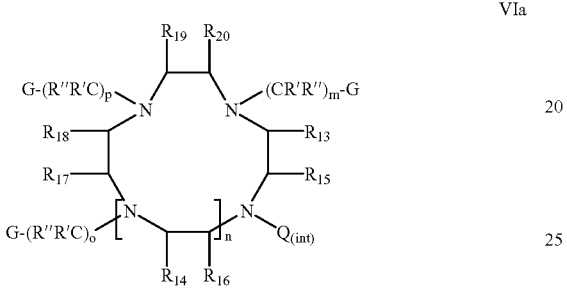

wherein
n is 0 or 1;
each m, o, and p is independently 1 or 2;
—Q(int) is a conjugatable amine-, carboxylate- or thiocarboxylate-containing group of formula —[C(R')(R")]$_{s1}$—[C(t)(R$_{21}$)]$_{s2}$—[C(R$_{22}$)(R$_{23}$)]$_{s3}$—X$_3$—Y—X$_4$; wherein
s1, s2, s3, and s4 are independently 0 to 2;
X$_3$ is a single bond, —O—, —S—, —NH— or —NR$_{24}$— if Y is present, or X$_3$ is —OH, —SH, —NH$_2$ or —N(R$_{24}$)H if Y and X$_4$ are absent;
X$_4$ is a single bond, —OH, —COOH, —SH, —NHR$_{24}$ or —NH$_2$;
Y is a single bond, —C(R$_{25}$)(R$_{26}$)—, or Y1
wherein,
Y1 is —C(=X$_5$)—X6—W—, wherein
X$_5$ is =O or =S;
X$_6$ is a single bond, —SH, —NH(R$_{38}$), —NH$_2$ or —OH if W and X$_4$ are absent, and is —S—, —O—, —NH—, or —N(R$_{39}$)—, if W and X$_4$ are present;
W is a single bond, or is -alkylidene-, -cycloalkylidene-, -arylidene-, -alkenylidene-, or -alkynylidene-, whose carbon atoms may or may not be substituted;
t is —H, —R$_{27}$, —C(O)OR$_{28}$, —P(O)(OR$_{29}$))OH, —P(O)(OR$_{30}$))OR$_{31}$, —P(O)(OR$_{32}$)R$_{33}$, —P(O)(OH)R$_{34}$—C(O)N(R$_{35}$)(R$_{36}$), or —C(O)NH(R$_{37}$);
each —G is independently —C(O)OR''', —P(O)(OR''')OH, —P(O)(OR''')$_2$, —P(O)(OR''')R", —P(O)(OH)R"—C(O)N(R''')$_2$, or —C(O)NH(R''');
each —R' and —R" is independently a single bond, —H, -alkyl, -alkoxy, -cycloalkyl, -hydroxyalkyl, -aryl, or -heterocyclo, each of which is optionally substituted,
each —R''' is independently —H, -alkyl, -cycloalkyl, -hydroxyalkyl, -aryl, or -heterocyclo, each of which is optionally substituted,
each —R$_{13}$ through —R$_{23}$, and —R$_{25}$ through —R$_{27}$ is independently —H, -alkyl, alkoxy, -halogen, -hydroxy, -cycloalkyl, -hydroxyalkyl, -aryl, or -heterocyclo, each of which is optionally substituted;
each —R$_{24}$, and —R$_{28}$ through —R$_{39}$ is independently —H, -alkyl, -alkenyl, cycloalkyl, aryl, a 5- or 6-membered nitrogen or oxygen containing heterocycle, each of which is optionally substituted;
or R$_{13}$ together with R$_{15}$, and R$_{17}$ together with R$_{18}$, independently form, together with the carbon atoms in the polyazamacrocycle to which they are attached, a fused fully or partially saturated non-aromatic cyclohexyl ring which may be unsubstituted or substituted by one or more halogen, alkyl, ether, hydroxy, or hydroxyalkyl groups, and which may be further fused to a carbocyclic ring, or R$_{13}$ and R$_{15}$ are each hydrogen and R$_{17}$, together with R$_{18}$, forms a fused fully or partially saturated non-aromatic cyclohexyl ring as defined above, or R$_{13}$, together with R$_{15}$, forms a fused fully or partially saturated non-aromatic cyclohexyl ring as defined above, and R$_{17}$ and R$_{18}$ are hydrogen;
or a salt thereof.

(ii) Monomeric Conjugates Bearing one Folate and one or two Polyaza Macrocyclic Ligand Moieties The conjugatable intermediates of formula VIa can be used to prepare the monomeric folate receptor binding conjugates of formula II:

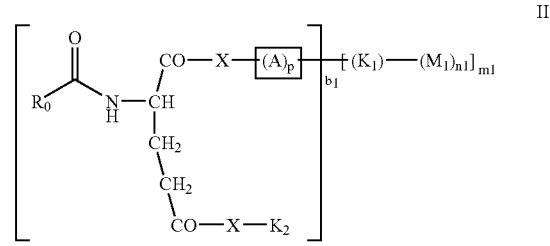

wherein R$_0$ is a folate-receptor binding residue of formula:

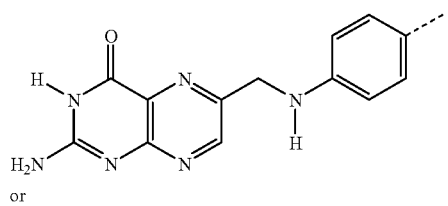

or

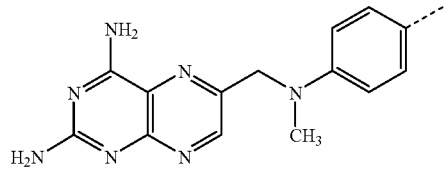

each X is independently —O—, —S—, —NH—, or —NR$_1$—;
n1 is 0 or 1;
b1 is 1–3;
m1 is 1

$K_1$ is —H, -alkyl, -alkenyl, -alkynyl, -alkoxy, -aryl, -alkyl, —CON($R_2$)$_2$, -glutamate,- or polyglutamate, or a metal chelating ligand radical of formula VI:

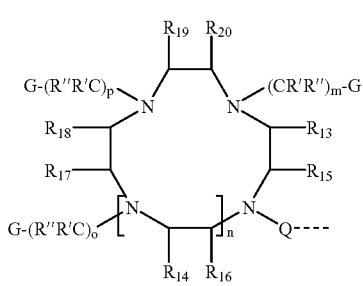

that is optionally chelated to a radioactive or paramagnetic metal;

$K_2$ is —H, -alkyl, -alkenyl, -alkynyl, -alkoxy, -aryl, -alkyl, —CON($R_2$)$_2$, -glutamate, -polyglutamate, or

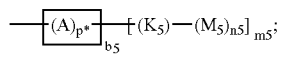

wherein
- $K_5$ is a macrocyclic ligand radical of formula VI that is optionally chelated to a radioactive or paramagnetic metal $M_5$; with the proviso that at least one $K_1$ or $K_2$ must contain a ligand of formula VI;
- n5 is 0 or 1;
- b5 is 1;
- m5 is 1;
- —(A)p— and —(A)p*— are —Q—;
- Q is —[C(R')(R")]$_{s1}$—[C(t)($R_{21}$)]$_{s2}$——[C($R_{22}$)($R_{23}$)]$_{s3}$—$X_3$—Y—$X_4$—; wherein
- s1, s2, s3, and s4 are independently 0 to 2;
- $X_3$, $X_4$, $X_5$, and $X_6$ are independently a single bond, —O—, —S—, —NH, or —N($R_{24}$)—;
- Y is a single bond, —C($R_{25}$)($R_{26}$)—, or $Y_1$ wherein, $Y_1$ is —C(=$X_5$)—$X_6$—W—, wherein
  - W is a single bond, -alkylidene-, -cycloalkylidene-, arylidene-, -alkenylidene-, or -alkynylidene-, whose carbon atoms may or may not be substituted;
  - t is H, $R_{27}$, —C(O)O$R_{28}$, —P(O)(O$R_{29}$))OH, —P(O)(O$R_{30}$))O$R_{31}$, —P(O)(O$R_{32}$)$R_{33}$, —P(O)(OH)$R_{34}$—C(O)N($R_{35}$)($R_{36}$), or C(O)NH($R_{37}$);
- each G is independently —C(O)OR''', —P(O)(OR''')OH, —P(O)(OR''')$_2$, —P(O)(OR''')R''', —P(O)(OH)R'''—C(O)N(R''')$_2$, or —C(O)NH(R''');
- each —R' and —R" is independently a single bond, —H, -alkyl, -alkoxy, -cycloalkyl, -hydroxyalkyl, -aryl, or -heterocyclo, each of which is optionally substituted,
- each —R'" is independently —H, -alkyl, -cycloalkyl, -hydroxyalkyl, -aryl, or -heterocyclo, each of which is optionally substituted,
- each —$R_{13}$ through —$R_{23}$, and —$R_{25}$ through —$R_{27}$ is independently —H, -alkyl, alkoxy, -halogen, -hydroxy, -cycloalkyl, -hydroxyalkyl, -aryl, or -heterocyclo, each of which is optionally substituted;
- each —$R_{24}$, and —$R_{28}$ through —$R_{39}$ is independently —H, -alkyl, -alkenyl, cycloalkyl, aryl, a 5- or 6-membered nitrogen or oxygen containing heterocycle, each of which is optionally substituted;

or $R_{13}$ together with $R_{15}$, and $R_{17}$ together with $R_{18}$, independently form, together with the carbon atoms in the polyazamacrocycle to which they are attached, a fused fully or partially saturated non-aromatic cyclohexyl ring which may be unsubstituted or substituted by one or more halogen, alkyl, ether, hydroxy, or hydroxyalkyl groups, and which may be further fused to a carbocyclic ring, or $R_{13}$ and $R_{15}$ are each hydrogen and $R_{17}$, together with $R_{18}$, forms a fused fully or partially saturated non-aromatic cyclohexyl ring as defined above, or $R_{13}$, together with $R_{15}$, forms a fused fully or partially saturated non-aromatic cyclohexyl ring as defined above, and $R_{17}$ and $R_{18}$ are hydrogen;

or a salt thereof.

Compounds of formula II that contain metal-chelating ligand radicals of formula VI having enhanced relaxivity properties are especially preferred.

(iii) Multimeric (dendrimeric) Conjugates Bearing one Folate and more than one Polyaza Macrocycle Moiety The dendrimeric conjugates described herein contain multiple metal chelating ligands. Such multimeric compounds are particularly useful as contrast agents for MRI, as multiple paramagnetic metals can be localized at the target tissue upon binding of a single folate receptor binding moiety. If these metal chelates are chosen to have enhanced relaxivity properties, said dendrimers may provide improved sensitivity if used as MRI contrast agents designed for the detection of folate-receptor positive tissue, or improved efficacy if used for neutron capture therapy, due to the increased concentration of gadolinium in the cells. However, it is understood that said structures could also be prepared using ligands that are suitable for chelation to radioactive metals, for use in radiotherapy or radiodiagnosis.

Said dendrimeric conjugates are represented by formulae VIIa–VIId, all of which have the general structure depicted by formula VII:

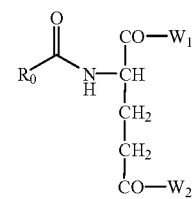

wherein $R_0$ is a folate-receptor binding residue of formula:

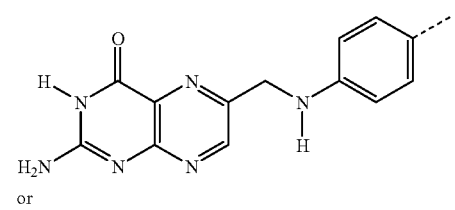

or

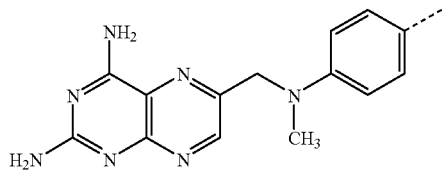

Variations in $W_1$ and $W_2$ (denoted by formulas VIIa–VIId below) represent dendrimers of generations 1, 2, 3, and 4, respectively. Such dendrimeric structures allow the incorporation of multiple metal chelating residues per molecule. Compounds where the metal-chelating ligand radical is present on $W_1$ and not on $W_2$ (alpha derivatives) are preferred. In the description below, the metal chelating radical is a derivative of the macrocyclic ligand intermediates of formula VIa. However, other ligand systems are also envisioned.

a. Dendrimeric Conjugates of Formula VIIa–VIId Bearing one Folate Residue and More than one Metal Chelating Residues (1) Ratio 1:3 or 1:6 dendrimer VIIa of the first generation:
These are described by formula VII:
wherein
for the first generation dendrimers of formula VIIa, bearing one folate-receptor binding residue and 3 or 6 metal chelating ligand radicals:
$W_1$ and $W_2$ of formula VII are each independently —OR''', —SR''', —NR'''R''''—CON($R_2$)$_2$, -glutamate, -polyglutamate, or —$K_6$; wherein each —R''' is independently —H, -alkyl, -aryl, -cycloalkyl, -hydroxyalkyl, or -heterocyclo;
with the proviso that either $W_1$, $W_2$, or both $W_1$ and $W_2$ of formula VIIa must be —$K_6$, where —$K_6$ is a residue of formula VIIIa:

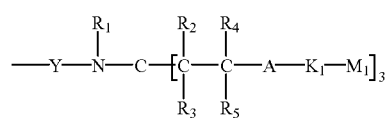

VIIIa wherein
Y is a single bond or —Y'—C(=X)— wherein
  X is =O or =S;
  Y' is N($R_6$)—Z—; wherein
    Z is a single bond, -alkylidene-, -vinylidene-, -cycloalkylidene-, or -arylidene-;
  A is —C(=O)—, C(=S), or —CH$_2$—N($R_7$)—;
  $M_1$ is a superparamagnetic, paramagnetic, radioactive or non-radioactive metal that is optionally bound to $K_1$;
  $K_1$ is a macrocyclic metal chelating ligand radical of formula VI;
    that is attached through the free —N(R)— atom of the function Q if A is —C(O)— or —C(S)—, or through the free —C(O)— atom of the function Q if A is —CH$_2$—N($R_7$)—;
  $R_1$ to $R_7$ is H, alkyl, hydroxyalkyl, alkoxy, alkoxyalkyl, cycloalkyl, or aryl.

(2) Ratio 1:9 or 1:18 dendriner VIIb of the second generation
These are described by formula VIIb:
wherein
$W_1$ and $W_2$ of formula VII are each independently —OR''', —SR''', —NR'''R'''', or —$K_7$, and —$K_7$ is a residue of formula VIIIb;
with the proviso that either $W_1$, $W_2$, or both $W_1$ and $W_2$ must be —$K_7$ (a residue of formula VIIIb):

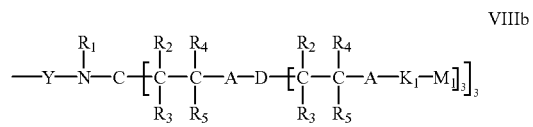

VIIIb wherein
X, Y, X', Z, A, $K_1$, $M_1$, R''' and all R groups are defined as in formula VIIa;
D is —N($R_6$)—C— if A is —C(O)— or —C(S)— and —C(=$X_2$)—E—N($R_7$)—C— if A is —CH$_2$—N($R_7$)—;
  wherein E is a single bond, alkylidene, vinylidene, cycloalkylidene, or arylidene and $X_2$ is =O or =S;

(3) Ratio 1:27 or 1:54 dendrimer VIIc of the third generation
These are described by formula VIIc
wherein
$W_1$ and $W_2$ of formula VII are each independently —OR''', —SR''', —NR'''R''', or —$K_8$; wherein —$K_8$ is a residue of formula VIIIc;
with the proviso that either $W_1$, $W_2$, or both $W_1$ and $W_2$ of the compounds of formula VIIc must be —$K_8$:

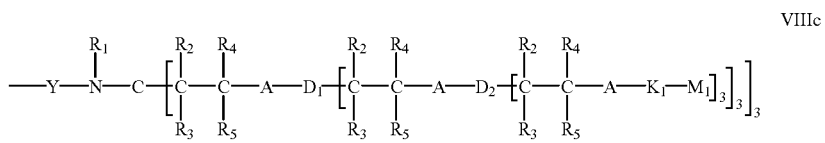

VIIIc wherein,

X, Y, X', Z, A, $K_1$, $M_1$, R''' and all R groups are defined as in formula VIIa;
$D_1$ and $D_2$ are independently —N($R_6$)—C— if A is C(O) or C(S), and —C(=$X_2$)—E—N($R_7$)—C if A is —CH$_2$—N($R_7$)—;
  wherein E is a single bond, alkylidene, vinylidene, cycloalkylidene, or arylidene and $X_2$ is =O or =S;

(4) Ratio 1:81 or 1:162 dendrimer VIId of the fourth generation

These are described by formula VIId wherein $W_1$ and $W_2$ of formula VII are each independently —OR''', —SR''', —NR'''R''' or —$K_9$;
wherein —$K_9$ is a residue of formula VIIId;
with the proviso that either $W_1$, $W_2$, or both $W_1$ and $W_2$ must be —$K_9$ (a residue of formula VIIId):

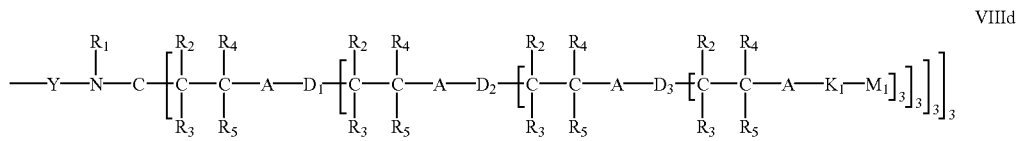

wherein,

X, Y, X', Z, A, $K_1$, $M_1$, R''' and all R groups are defined as in formula VIIa;

$D_1$, $D_2$, and $D_3$ are independently —N($R_6$)—C— if A is —C(O)— or —C(S)—, and —C(=$X_2$)—E—N($R_7$)—C if A is —$CH_2$—N($R_7$)—;

wherein E is a single bond, alkylidene, vinylidene, cycloalkylidene, or arylidene and $X_2$ is =O or =S;

b. Multimeric Conjugates Bearing more than one Folate and Polyaza Macrocyclic Ligand Residues Dendrimeric conjugates of this type are depicted by formulae IXa, IXb, IXc, and IXd representing dendrimers of generations 1, 2, 3, and 4, respectively.

(1) Ratio 3:3 dendrimer IXa of the first generation

Dendrimers with a ratio of three folate receptor binding residues to three metal chelating residues are depicted by formula IXa:

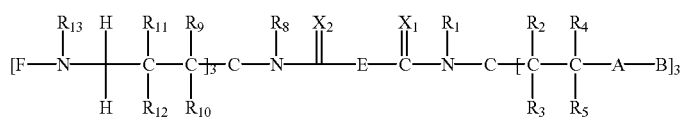

wherein

F is a folate-receptor binding residue of formula:

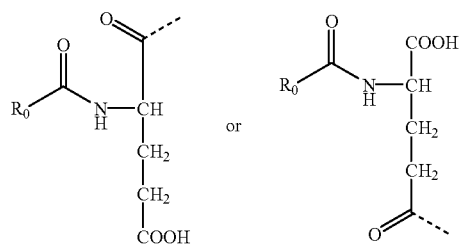

wherein $R_0$ is a residue of formula:

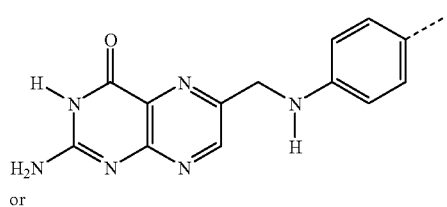

or

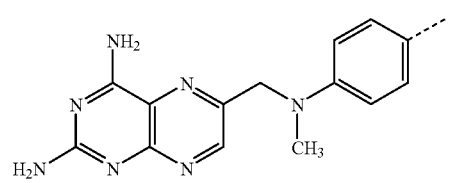

dentoes the point of attachment of the residues above.

$X_1$ and $X_2$ are independently =O or =S;

A is —C(O)—, —C(S)— or —$CH_2$—N($R_7$)—;

B is a metal chelating ligand radical of formula VI attached through the free N atom of the function —Q— if A is —C(O)— or through the free C(O) atom of the function Q if A is —$CH_2$—N($R_7$)—;

E is a single bond, alkylidene, vinylidene, cycloalkylidene, or arylidene;

—$R_1$, —$R_6$ through —$R_8$, —$R_{13}$, and —$R_{14}$ are independently —H, -alkyl, -hydroxyalkyl, -cycloalkyl, or -aryl;

—$R_2$ through —$R_5$ and —$R_9$ through —$R_{12}$ are independently —H, -alkyl, -hydroxyalkyl, -alkoxy, -hydroxyalkyl, -halogen, -cycloalkyl, -aryl or -heterocyclo;

(2) Ratio 9:9 Dendrimner IXb of the Second Generation

Dendrimers with a ratio of nine folate receptor binding residues to nine metal chelating ligand residues are depicted by formula IXb:

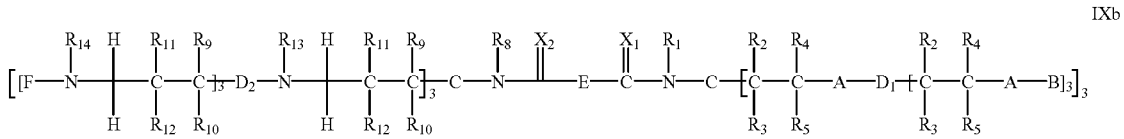

IXb wherein
- A, B, E, F, $X_1$ through $X_4$ are as defined for the compounds of formula IXa;
- $D_1$ and $D_2$ are each independently —N($R_6$)—C— if A is C(O) or C(S)—, and —C(=$X_3$)—E—N($R_7$)—C if A is —$CH_2$—N($R_7$)—;
- $R_1$ to $R_{14}$ is H, alkyl, hydroxyalkyl, alkoxy, alkoxyalkyl, cycloalkyl, or aryl.

(3) Ratio 27:27 Dendrimer IXc of the Third Generation

Dendrimers with a ratio of 27 folate receptor binding residues to 27 metal chelating ligand residues are depicted by formula IXc:

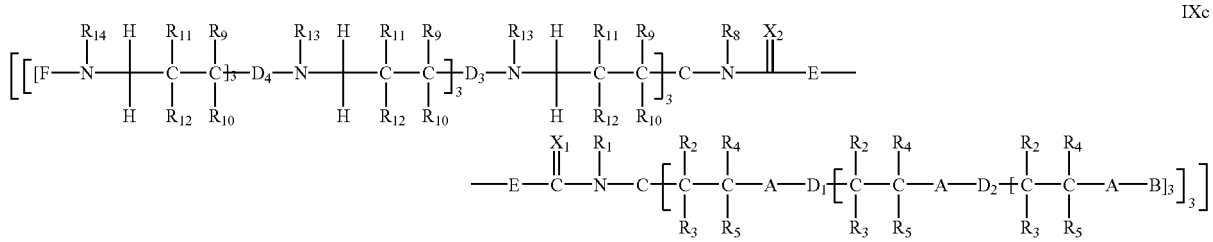

IXc wherein
- $D_1$, $D_2$, $D_3$, and $D_4$ are independently —N($R_6$)—C— if A is C(O) or —C(=$X_3$)—E—N($R_7$)—C if A is —$CH_2$—N($R_7$)—; and all other groups are as defined above.

(4) Ratio 81:81 Dendrimer IXd of the Fourth Generation

Dendrimers with a ratio of 81 folate receptor binding residues to 81 metal chelating residues are depicted by formula IXd:

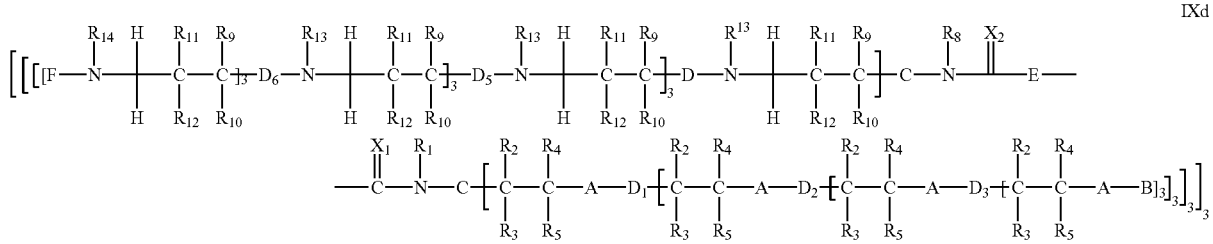

IXd wherein
- A, B, E, F, $K_1$, $M_1$ and all —R groups are is defined as in formula IXc;
- $X_1$, $X_2$ and $X_3$ are independently =O or =S; and
- $D_1$, $D_2$, $D_3$, $D_4$, $D_5$, and $D_6$ are independently —N($R_6$)—C— if A is C(O) or C(S), and —C(=$X_3$)—E—N($R_7$)—C if A is —$CH_2$—N($R_7$)—;

It is readily conceivable that those skilled in the art could visualize dendrimers of higher generations and also dendrimers having any combinations of folate residues and polyaza macrocyclic ligand residues by the appropriate choice of precursors. Though such structures are not specifically shown, the scope of the present invention will encompass such structures. In addition, it should be obvious that these dendrimers could be prepared with metal chelating ligands other than the polyaza macrocycles shown here.

(B) Methods for the Preparation of Folate Conjugates with Polyaza Macrocyclic Ligands (i) Preparation of the DOTA monoamide conjugates of the Present Invention a. The APADO3A γ-folate conjugate 6

Figure 5:
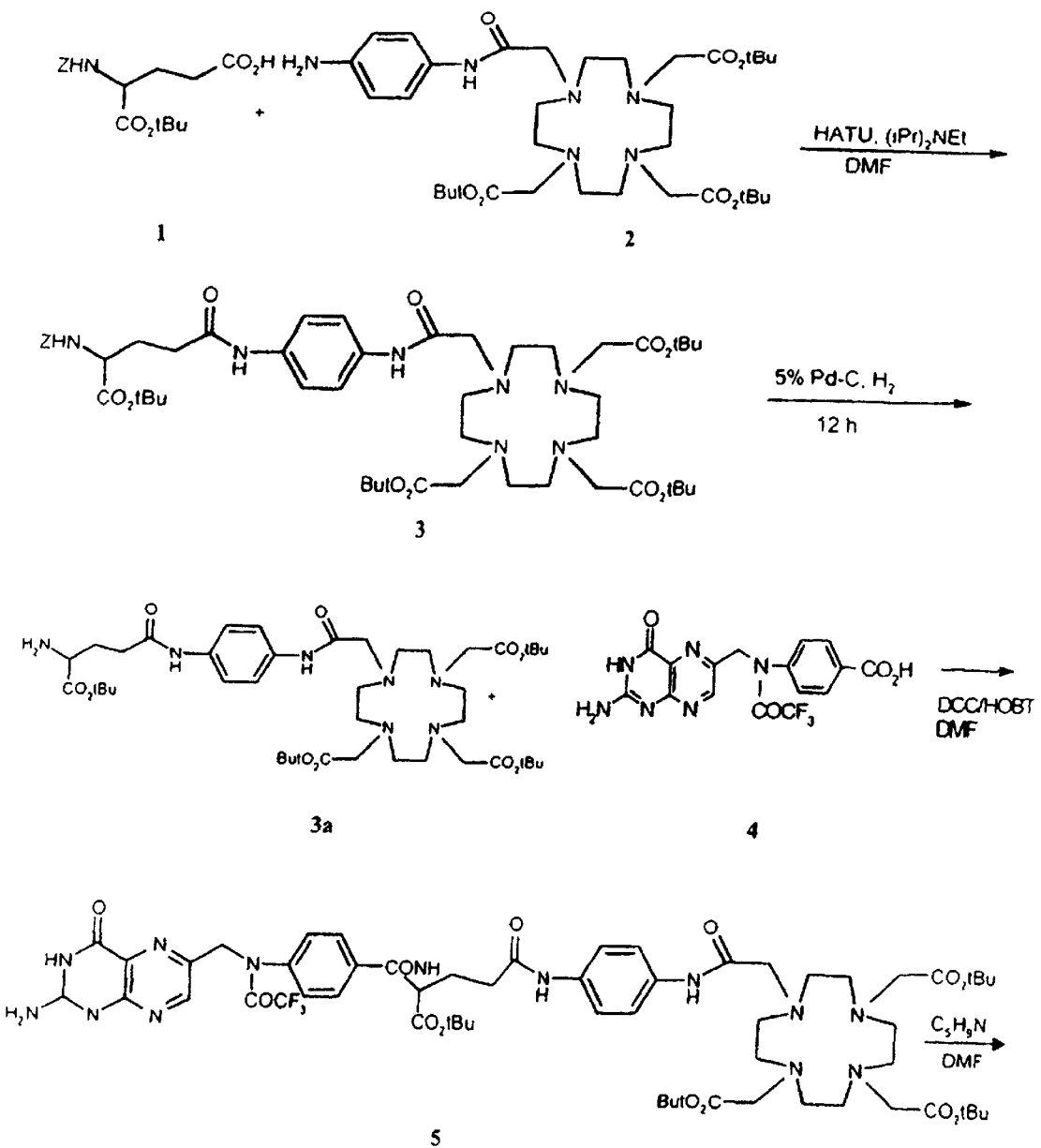
FIGS. 5 and 5A show the synthetic scheme for the preparation of the $\gamma$-isomer of the folic acid APADO3A conjugate 6.
Figure 5A:
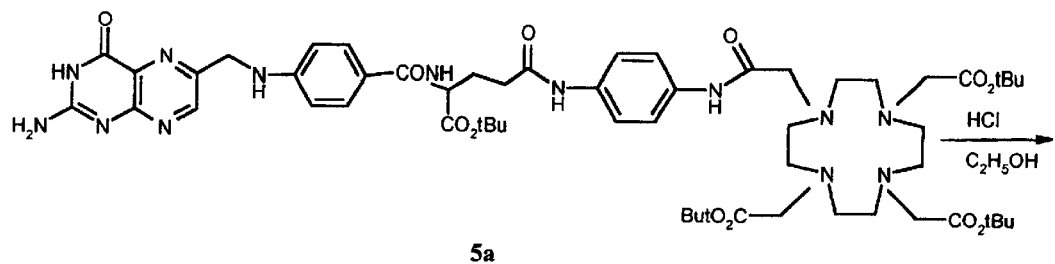
Figure 5A:
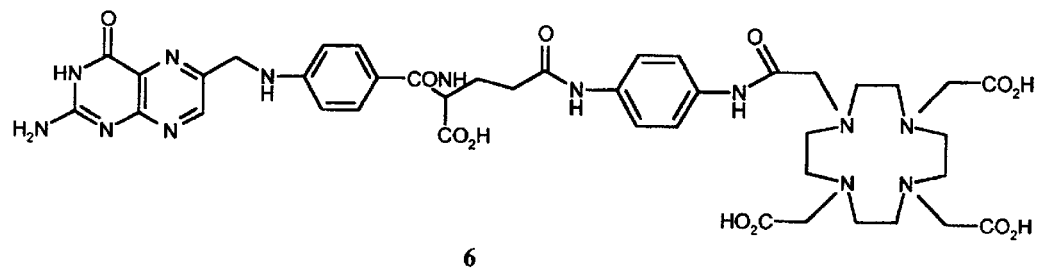
Figure 5A:
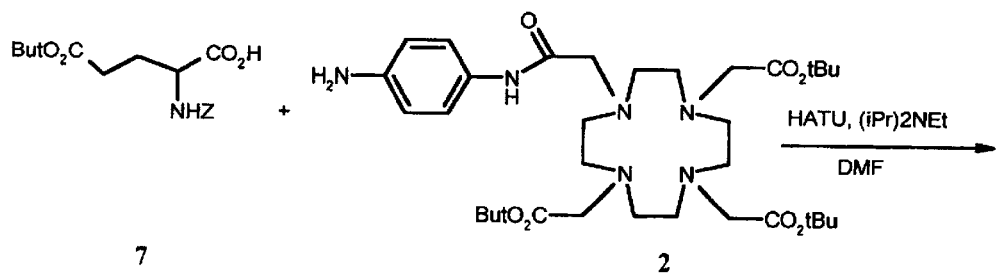

The synthetic scheme for the preparation of the γ-isomer of the folic acid APADO3A conjugate 6 is given in FIGS. 5 and 5A. It is to be understood that other ligands can be complexed with the γ-carboxylate of the folic acid analogously to that of DO3A.

APADO3A tris-t-butyl ester 2 was coupled with the α-carboxy protected glutamate derivative 1 to obtain 3. Deprotection and further coupling with the pteroic acid derivative 4 provided 5. Successive deprotections finally furnished the desired γ-folate conjugate 6.

b. The α-folate conjugate 10

Figure 6:
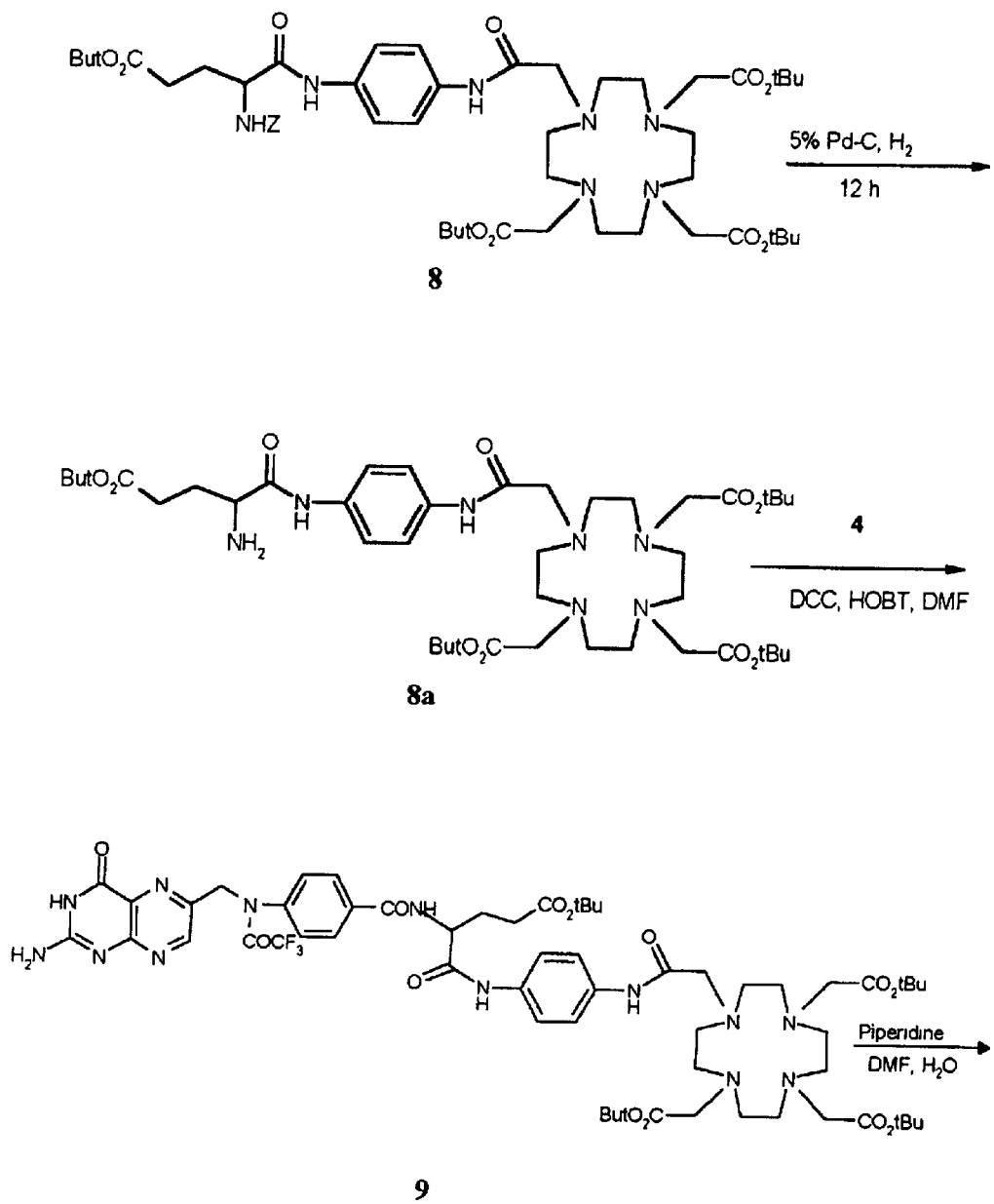
FIG. 6 and 6A show the synthetic scheme for the preparation of the $\alpha$-isomer of the folic acid APADO3A conjugate 10.
Figure 6A:
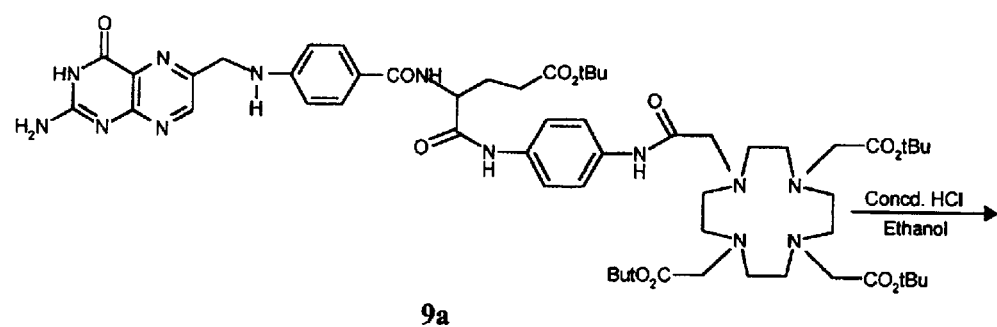
Figure 6A:
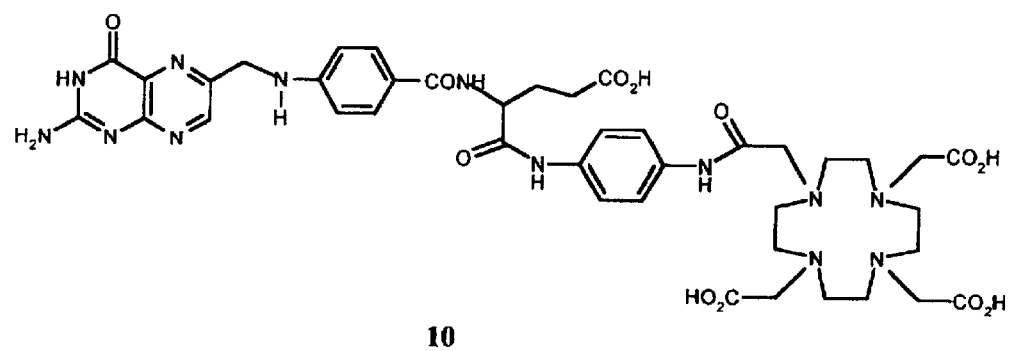

The synthetic scheme for the preparation of the α-isomer of folic acid APADO3A conjugate 10 is given in FIGS. 6A and 6B. It is to be understood that other chelating ligands can be conjugated to the α-carboxylate of folic acid analogously to that of DO3A.

APADO3A tris-t-butyl ester 2 was coupled with the γ-carboxy protected glutamate derivative 7 to obtain 8. Deprotection and further coupling with the pteroic acid derivative 4 provided 9. Successive deprotections finally furnished the desired α-folate conjugate 10.

c. The α,γ-bis folate conjugate 14.

Figure 7:
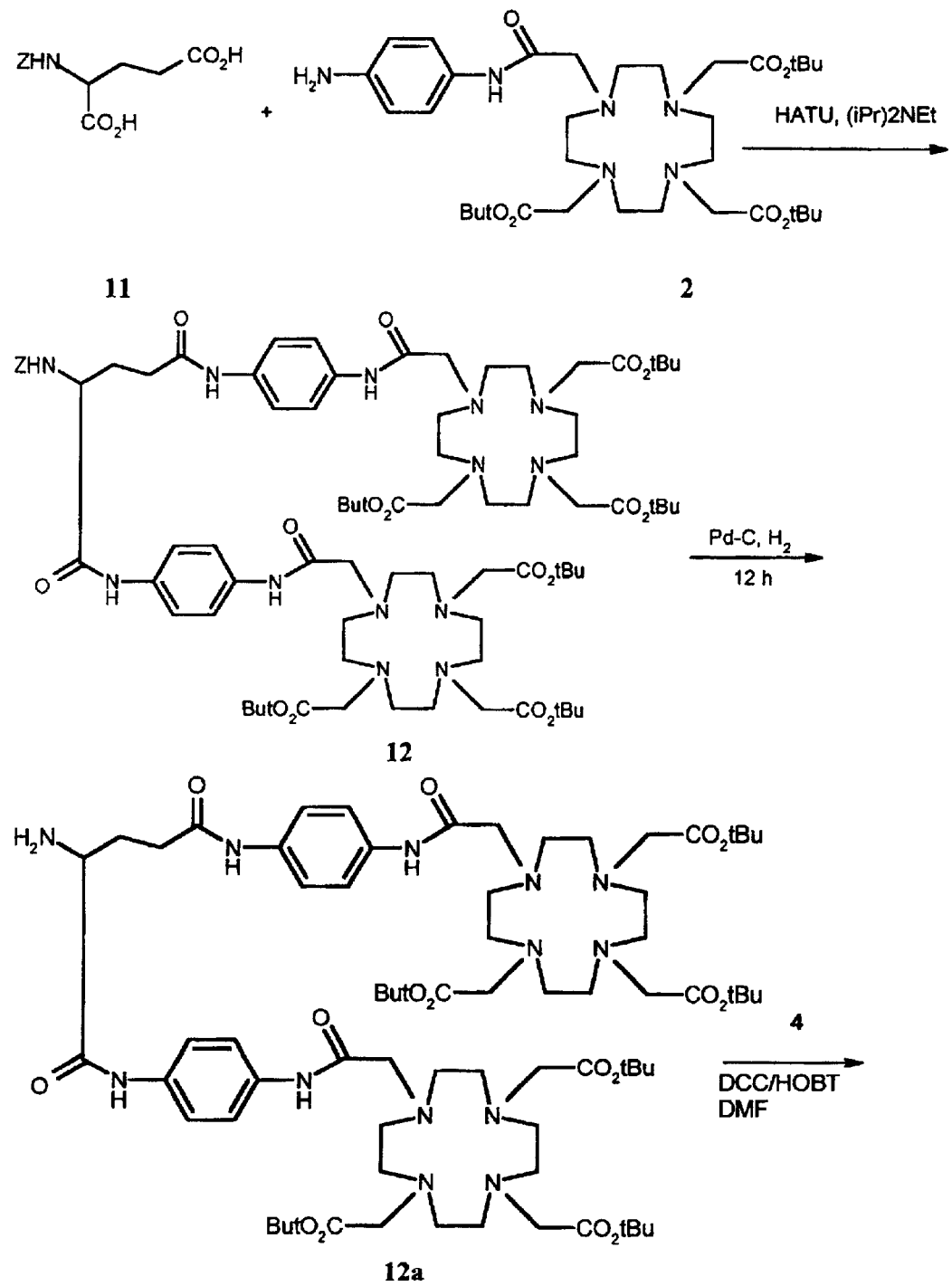
Figure 7A:
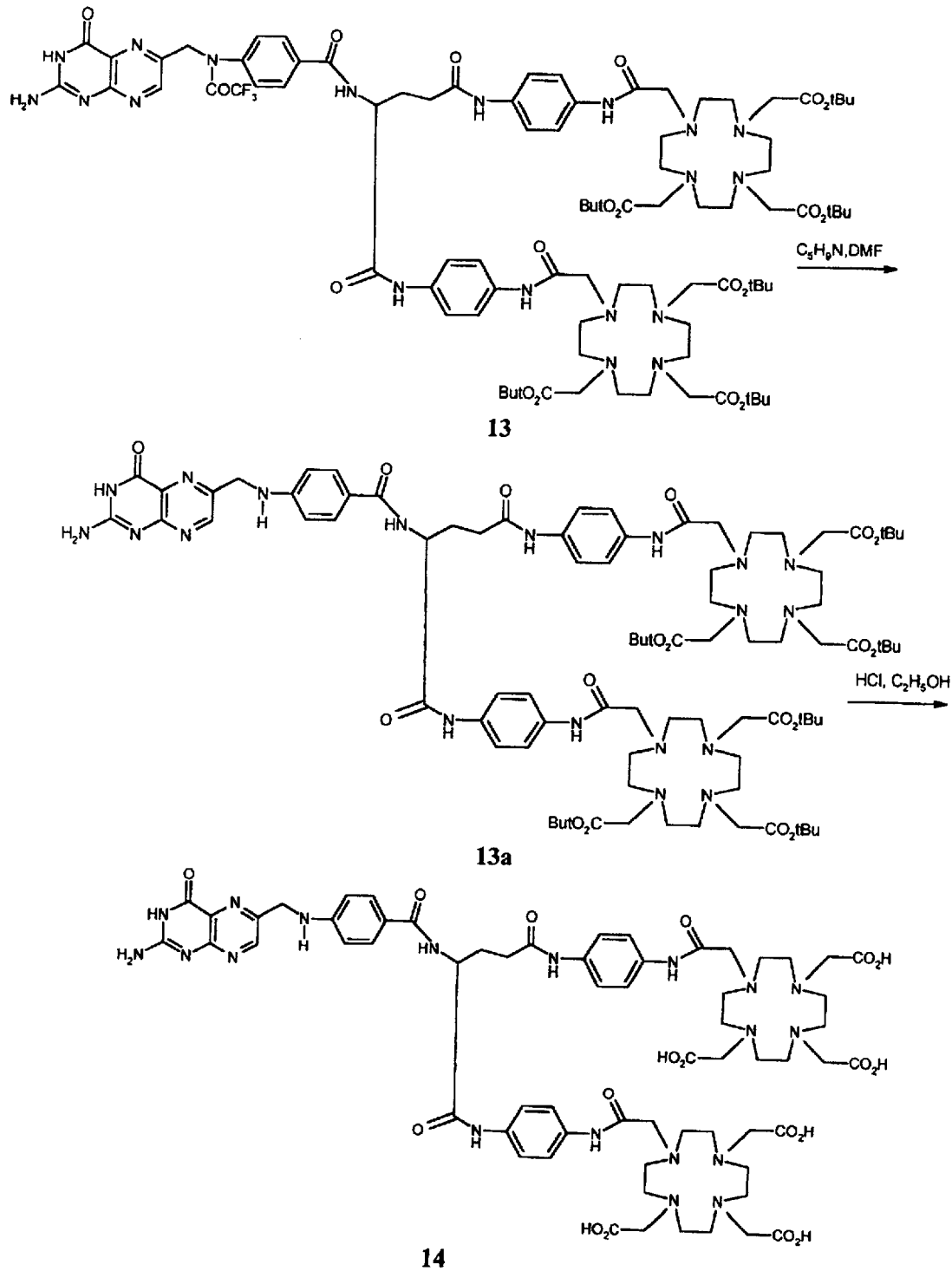

The synthetic scheme for the preparation of the folic acid bis(DO3A-APA) conjugate 14 is given in FIGS. 7, 7A, and 7B. It is to be understood that other macrocyclic or non-macrocyclic metal chelating ligands could be conjugated to the (α)- or (γ)- or both carboxylates of the folic acid analogously to that of DO3A, using coupling, protection and de-protection schemes well known to those skilled in the art.

APADO3A tris-t-butyl ester 2 was coupled with the N-protected glutamate derivative 11 to obtain 12. Deprotection and further coupling with the pteroic acid derivative 4 afforded 13. Successive deprotections finally furnished the desired α, γ-bis folate conjugate 14.

(ii) Preparation of Conjugatable Enhanced Relaxivity Polyaza Macrocyclic Ligands Our co-pending application WO 95/31444, published Nov. 23, 1995, teaches that the property of enhanced relaxivity is conferred on a molecule by the substitution of methyl groups on 3 or 4 of the macrocyclic carbon atoms and/or the carboxymethyl arms of DOTA or DO3A. In this manner the enhanced molecules M4DOTA, M4DO3A, DOTMA, DO3MA, and M4DOTMA are obtained. Replacement of one of the carboxymethyl arms of DOTA by the phosphonomethyl arm also provides the enhanced relaxivity molecule MPDO3A. The present invention will show pathways for the preparation of conjugatable enhanced relaxivity molecules based on these structures.

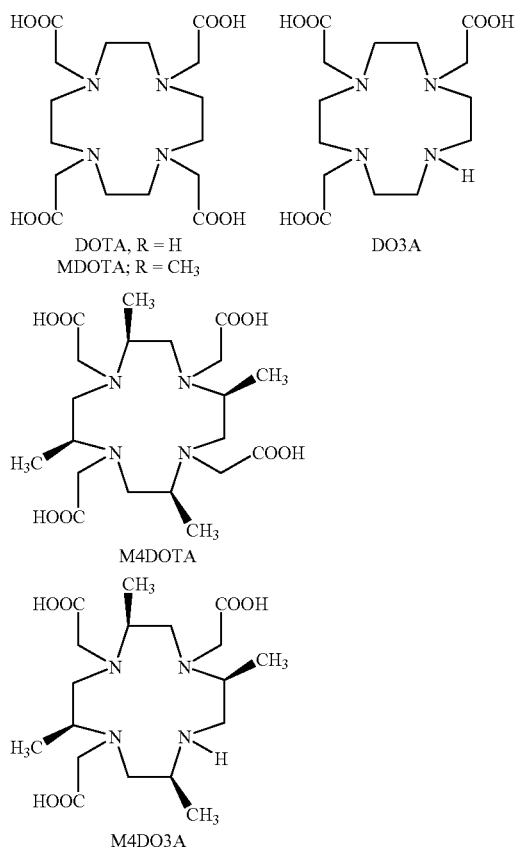

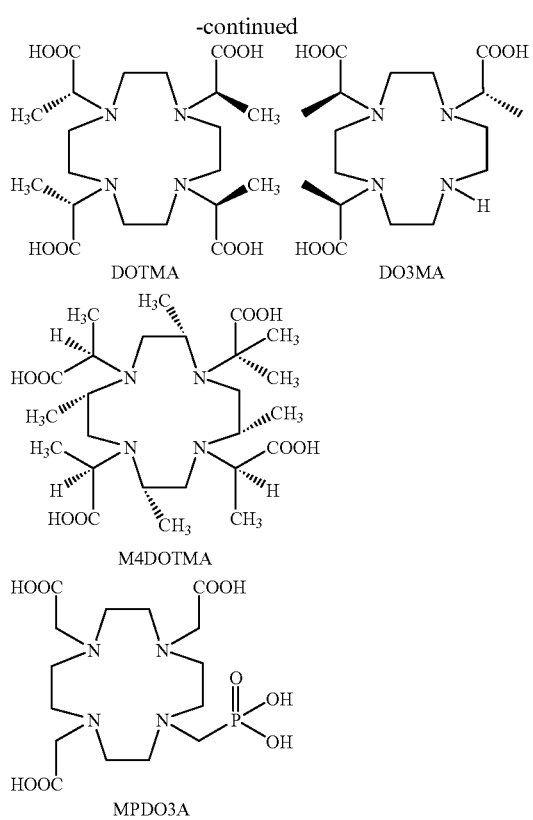

Figure 8:
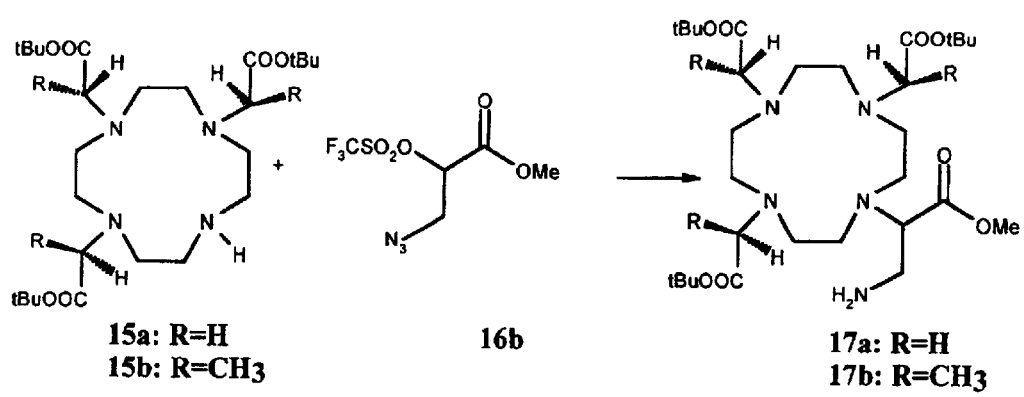
FIG. 8 shows the synthetic scheme for the preparation of a DO1MA analog 17a bearing a conjugable amino function, along with carboxyl protection that is necessary for conjugation, starting from DO3A-tris-t-butyl ester 15a, said DO1MA analog 17a could also be prepared starting from DO3MA-tris-t-butyl ester 15b.

A DO1MA analog 17a bearing a conjugatable amino function, along with carboxyl protection that is necessary for conjugation, could be prepared starting from DO3A-tris-t-butyl ester (15a) as shown in FIG. 8. A DOTMA analog 17b bearing a conjugatable amino function, along with carboxyl protection that is necessary for conjugation, could also be prepared starting from DO3MA-tris-t-butyl ester (15b) as shown in FIG. 8.

The preparation of 15a is described in U.S. Pat. No. 5,573,752 by Ranganathan et al. DO3MA is described in S. I. Kang et al., Inorg. Chem., 1993, 32, 2912–2918. DO3MA-tris-t-Bu ester 15b could be prepared from DO3MA by treatment with isobutylene in the presence of catalytic amounts of concentrated $H_2SO_4$. Alternatively, 15b could be made from 1,4,7,10-tetraazacyclododecane by tris-alkylation with t-butyl 2-triflyloxy-D-lactate following the methodology of S. I. Kang et al. (loc cit). t-Butyl 2-triflyloxy-D-lactate is readily obtained from commercially available t-butyl (D)-lactate by triflylation with triflic anhydride.

The preparation of the conjugatable ligand 17a has been achieved by the alkylation of 15a with methyl 3-azido-2-triflyloxy-propionate (16b) followed by catalytic hydrogenation in the presence of Pd/C catalyst. Similar alkylation of 15b with 16b is expected to afford the conjugatable ligand 15b bearing the amino function.

Figure 9:
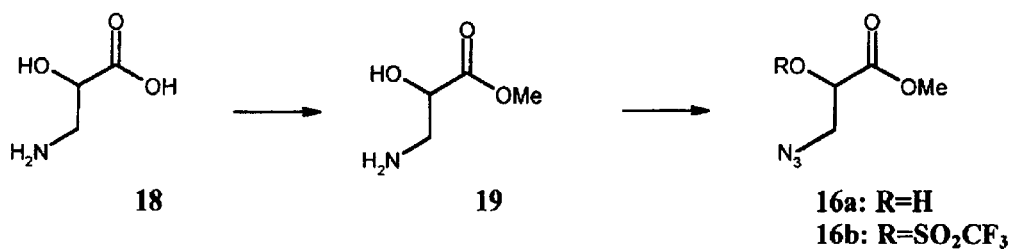
FIG. 9 shows the synthetic scheme for the preparation of azido-triflate 16b.

The azido-triflate 16b was prepared as shown in FIG. 9. Isoserine (18) was esterified by treatment with MeOH in the presence of concentrated HCl to obtain 19. The diazo transfer reaction on 19 by treatment with triflyl azide in the presence of $Cu^{2+}$ ion as described by P. B. Alper et al. in Tetrahedron Letters 1996, 37, 6029–6032, followed by triflylation by treatment with triflic anhydride and 2,6-lutidine gave the azido-triflate 16b.

Figure 10:
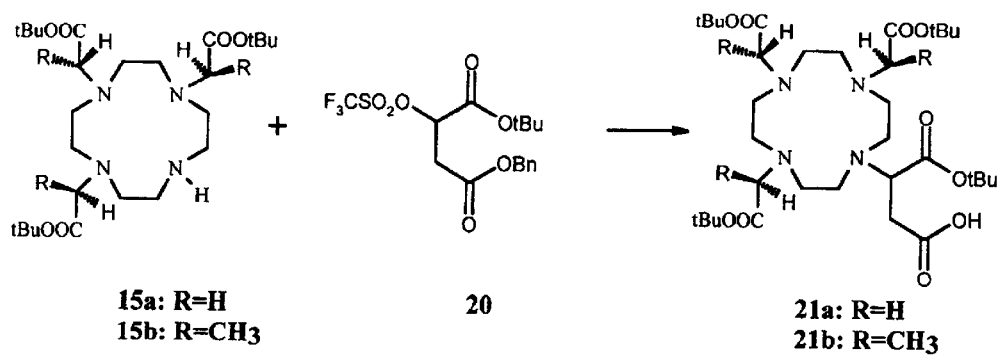
FIG. 10 shows the synthetic scheme for the preparation of the DO1MA analog 21a or DOTMA analog 21b bearing a conjugable carboxyl function starting from 15a or 15b, respectively.

The DO1MA analog 21a or DOTMA analog 21b bearing a conjugatable carboxyl function could be prepared starting from 15a or 15b, respectively, as shown in FIG. 10. For example, alkylation of 15b by the mixed diester, t-butyl benzyl 2-triflyloxy-malate 20, followed by debenzylation, employing catalytic hydrogenolysis, is expected to afford the enhanced relaxivity DOTMA analog 21b bearing the carboxyl function.

Figure 11:
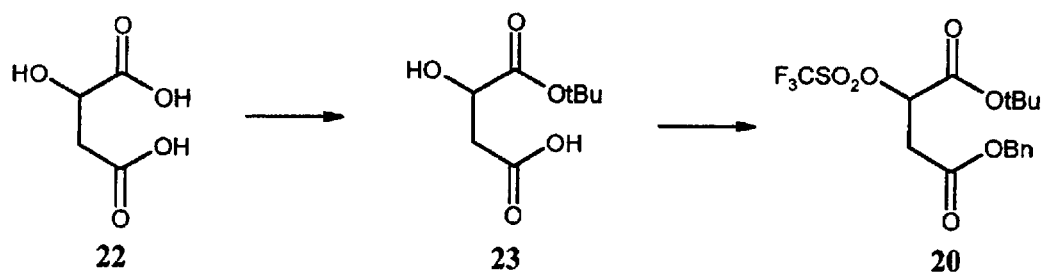
Figure 11:
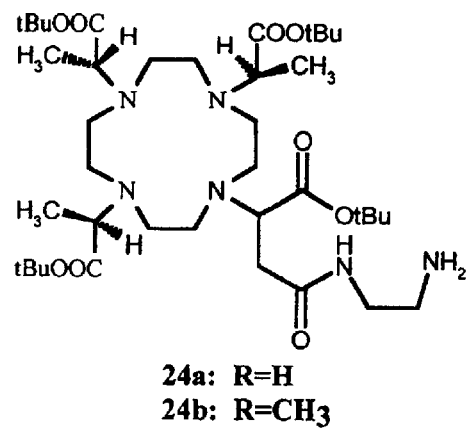

The triflyloxy mixed ester 20 could be readily made as shown in FIGS. 11 and 11A. t-Butyl malate 23 is made from malic acid (22) following the procedure described by N. Balcheva et al. in Eur. Polym. J., 1991, 27, 479–482. Selective benzylation of 23 by treatment with benzyl chloride and triethylamine, following the procedure described in S. I. Kang et al., Inorg. Chem., 1993, 32, 2912–2918 in the case of lactic acid, followed by triflylation with triflic anhydride and 2,6-lutidine is expected to furnish the synthon 20.

The carboxyl group bearing enhanced relaxivity DOTMA analog 21a or 21b could be readily converted into an amino group bearing ligands 24a or 24b, respectively, by first coupling 21a or 21b with a mono-protected ethylenediamine derivative such as ZNHCH$_2$CH$_2$NH$_2$ using HATU and diisopropylethylamine and then removing the Z group by catalytic hydrogenolysis in the presence of Pd/C catalyst.

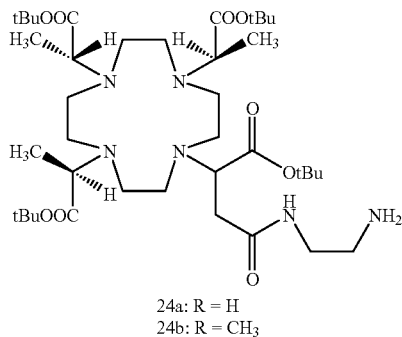

24a: R = H
24b: R = CH$_3$

Figure 12:
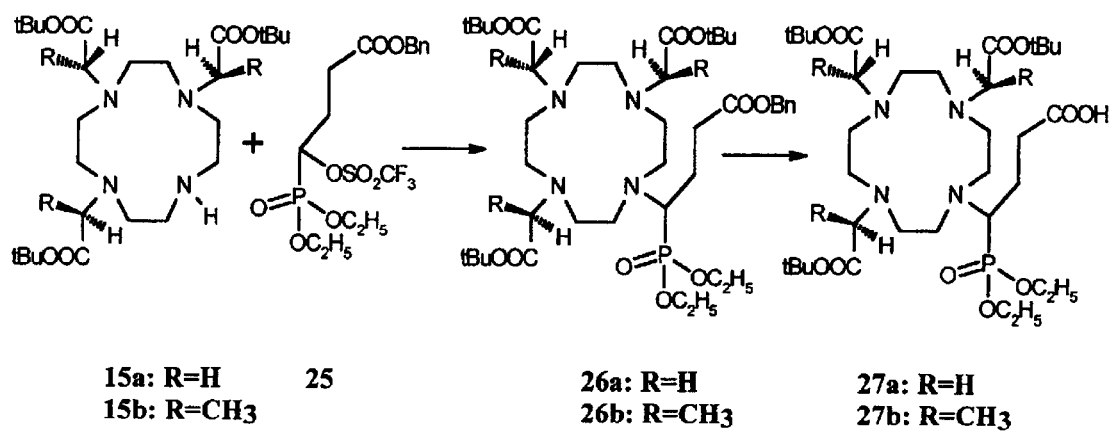
FIG. 12 shows the synthetic scheme for the preparation of the conjugable MPDO3A analogs 27a and 27b.

Conjugatable MPDO3A analogs 27a and 27b containing the carboxyl group are also accessible by methods shown in FIG. 12.

Alkylation of compound 15a by the triflate 25 is expected to provide the orthogonally protected ligand 26a. Debenzylation of 26a by catalytic hydrogenolysis will provide the carboxyl group containing enhanced relaxivity MPDO3A ligand 27a. Similar alkylation of 15b by the triflate 25 is expected to afford the MPDO3A analog 27b via the benzyl ester 26b.

Figure 13:
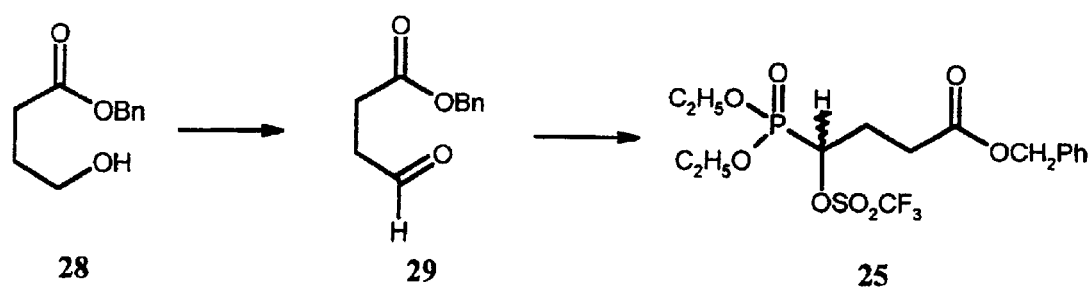
Figure 13:
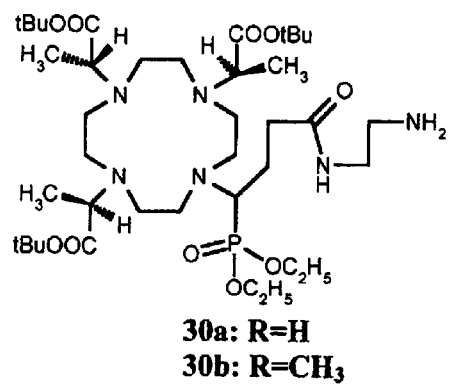

The alkylating agent 25 that is necessary for the above transformations could be prepared as shown in FIGS. 13 and 13A. Benzyl 4-Hydroxybutyrate (28) is prepared from 4-hydroxybutyric acid by selective benzylation with benzyl bromide as described in S. I. Kang et al., Inorg. Chem., 1993, 32, 2912–2918 in the case of lactic acid.

Oxidation of 28 by treatment with pyridinium chlorochromate will afford the aldehyde 29. Successive treatment of 29, first with triethylphosphite and then with triflic anhydride in the presence of a hindered base such as diisopropylethyl amine at low temperature is expected to furnish the trifluoromethanesulfonyloxy derivative 25.

The carboxyl group bearing enhanced relaxivity MPDO3A analogs 27a and 27b could be converted into amino group bearing ligands 30a and 30b, respectively, by first coupling 27a or 27b with a mono-protected ethylenediamine derivative such as ZNHCH$_2$CH$_2$NH$_2$ using HATU and diisopropylethyl amine, followed by catalytic hydrogenolysis in the presence of Pd/C catalyst.

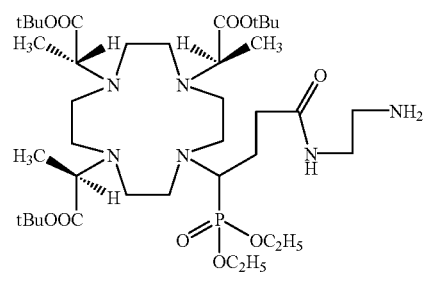

Figure 14:
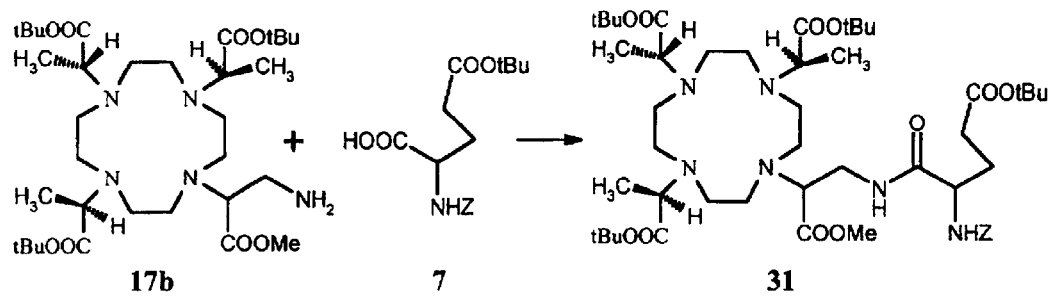
FIGS. 14 and 14A show the synthetic scheme for the preparation of the $\alpha$-folate conjugate 35a of the amino group-bearing enhanced relaxivity ligand 17b.
Figure 14:
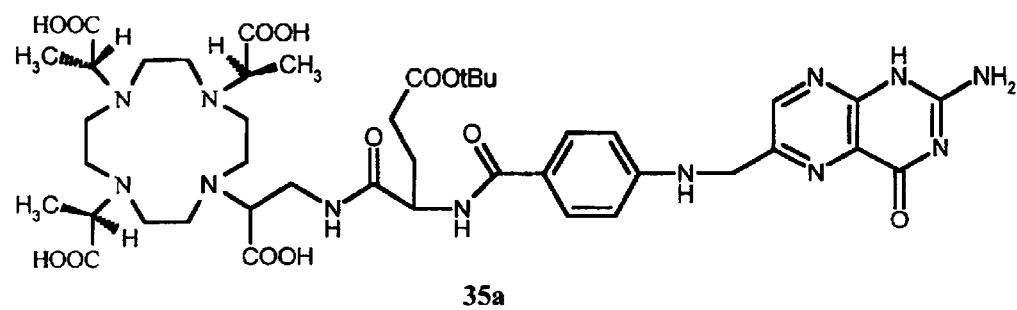
Figure 14:
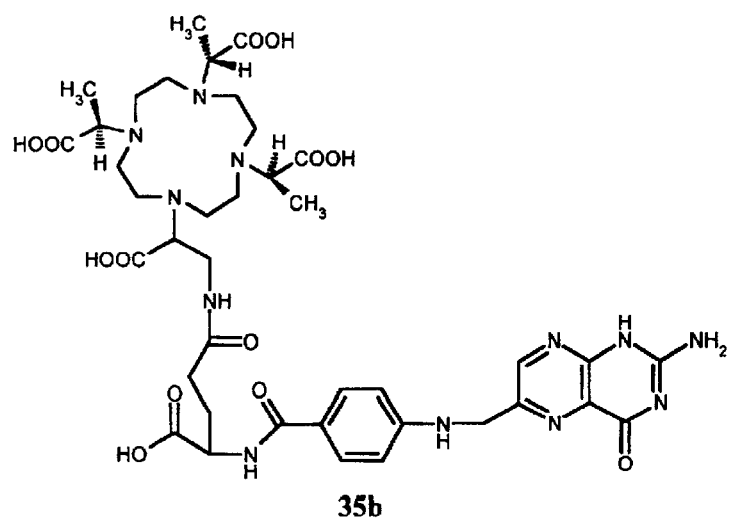
Figure 14A:
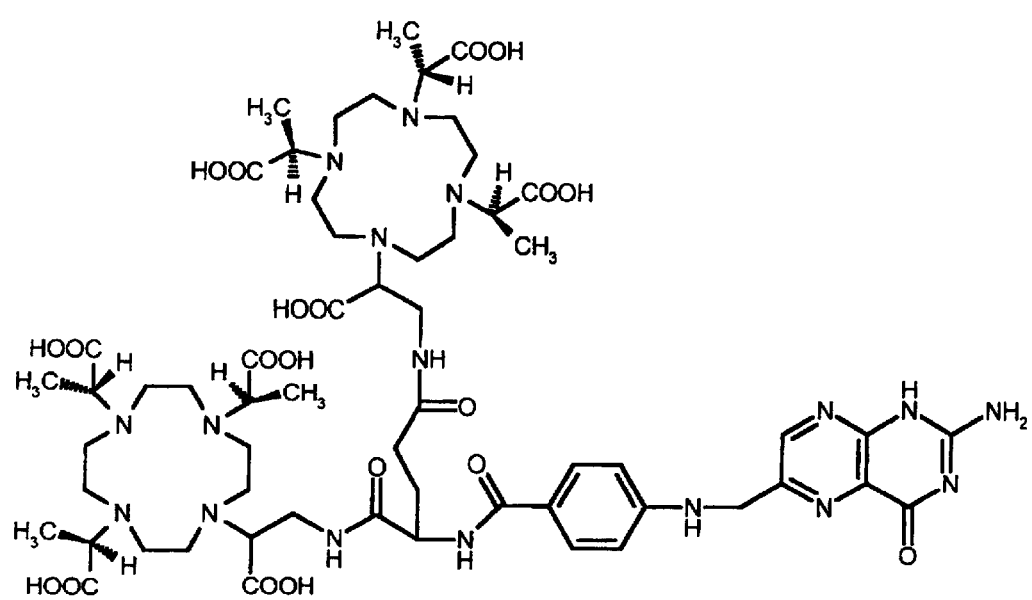

30a: R = H
30b: R = CH$_3$ (ii) Preparation of Monomeric Folate Conjugates with Enhanced Relaxivity Polyaza Macrocyclic Ligands The α-folate conjugate 35a of the amino group-bearing enhanced relaxivity ligand 17b could be prepared as shown in FIGS. 14 and 14A. Coupling ligand 17b with the γ-protected glutamate derivative ZNH-E(OtBU)-OH (7) using HATU and diisopropylethylamine in a solvent such as dimethylformamide is expected to furnish the product 31.

Removal of the benzyloxycarbonyl group of 31 and further coupling with N-trifluoroacetyl-pteroic acid (4) employing DCC and HOBT, followed by sequential deprotection with piperidine, aqueous base, and finally ethanolic HCl, is expected to provide the desired folate conjugate 35a.

The corresponding γ folate conjugate 35b can be prepared by a similar approach starting from the α protected glutamate derivative ZNH-E-(OtBu) (1). The α, γbis-conjugate 36 could also be made by coupling folic acid directly with two equivalents of the ligand 17b as per methods described above for the protected glutamic acid derivatives. Other enhanced relaxivity ligands such as 24 and 30 could be substituted for 7 in the above reactions to obtain the corresponding folate conjugates.

(iii) Preparation of Multimeric Folate Conjugates with Enhanced Relaxivity Polyaza Macrocyclic Ligands As discussed above, preparation of multimeric folate conjugates of Gd chelates could deliver a higher Gd concentration into the target cells, thereby increasing the signal intensity during MR imaging. The synthesis of suitable linkers for the preparation of such compounds will first be presented followed by the conjugation methods to obtain the folate conjugates.

a. Linker chemistry

Dendrimeric linkers are well known in literature. For example D. A. Tomalia and J. R. Dewald present examples of star burst dendrimers in U.S. Pat. No. 4,631,337. Smart cascade polymers are described by J. K. Young et al., Macromolecules, 1994, 27, 3464–3471. In the present invention the nitro-tris-carboxylate 37 and the tris-BOC protected tetra-amine 38, described by J. K. Young et al. (loc. cit.), are used as starting materials to develop a novel orthogonally protected tris-amino-tris carboxylate derivative 39.

Figure 15:
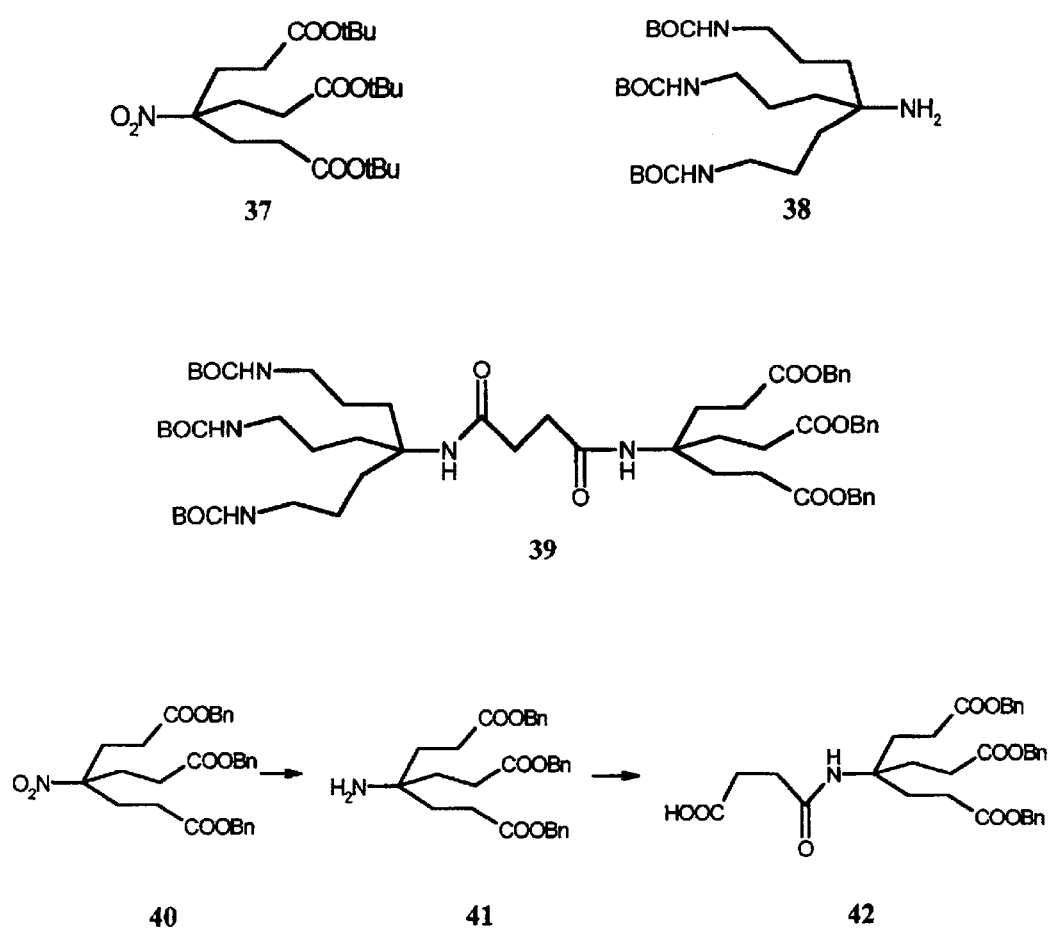
FIG. 15 shows the synthetic scheme for the preparation of the succinic monoamide tri-carboxylic ester 42.

The preparation of the succinic monoamido tri-carboxylic ester 42 was carried out as shown in FIG. 15.

Treatment of the nitro-tris-tBu ester 37 with trifluoroacetic acid followed by alkylation with benzyl bromide in pyridine provided the nitro-tris-benzyl ester 40. Reduction of the nitro group with Al/Hg gave the amine 41, which upon treatment with succinic anhydride in pyridine provided the succinic mono-amide 42.

Figure 16:
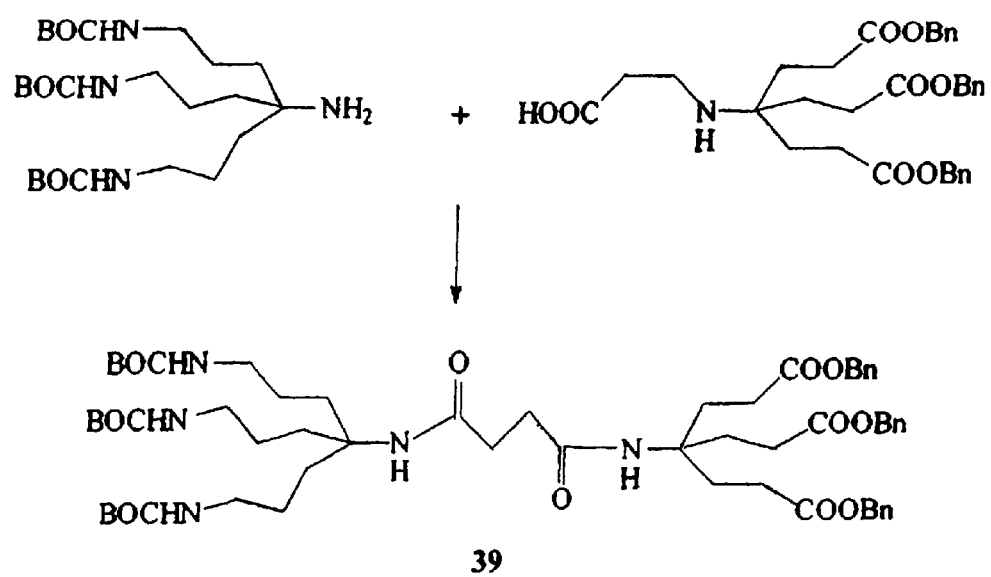
FIG. 16 shows the synthetic scheme for coupling amine 38 with the carboxylic acid 42 employing carbonyldiimidazole in dimethylformamide.

Coupling of the amine 38 with the carboxylic acid 42 employing carbonyldiimidazole in dimethylformamide, as shown in FIG. 16, yielded the orthogonally protected tris amino-tri carboxylate linker molecule 39.

b. Preparation of multimeric folate conjugates

The multimeric folate conjugate with enhanced relaxivity ligands, in which one folate moiety will be linked to three enhanced relaxivity ligand moieties, could be made as follows.

Figure 17:
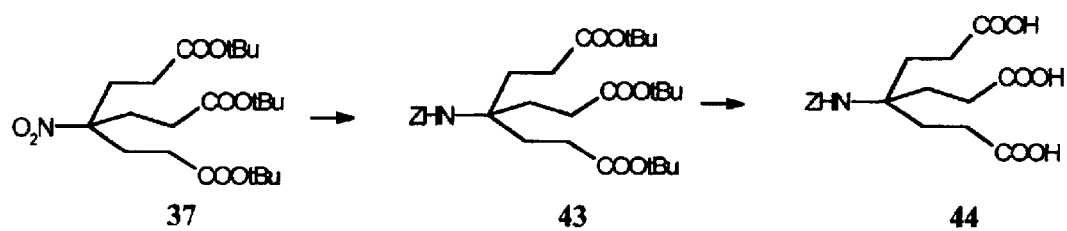
FIGS. 17 and 17A show the synthetic scheme for the preparation of the protected amino tricarboxylic ester 44.
Figure 17:
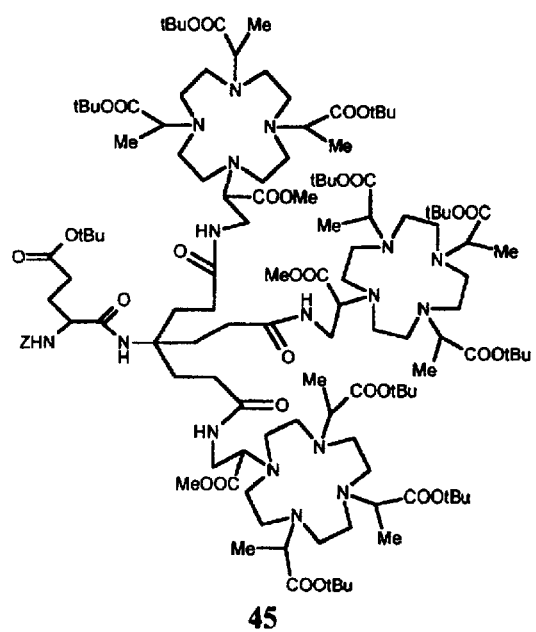
Figure 17A:
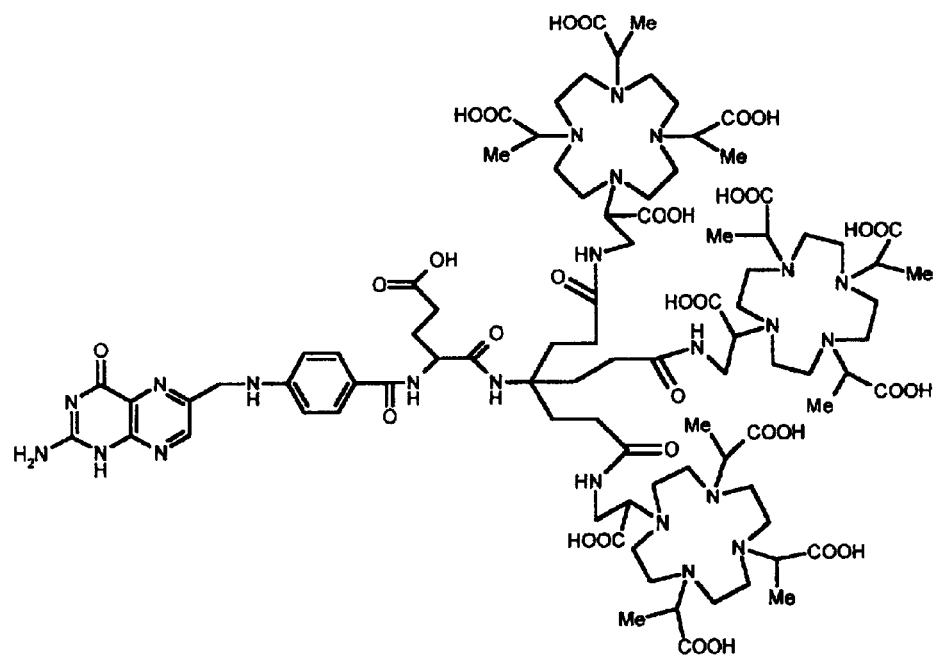
Figure 17A:
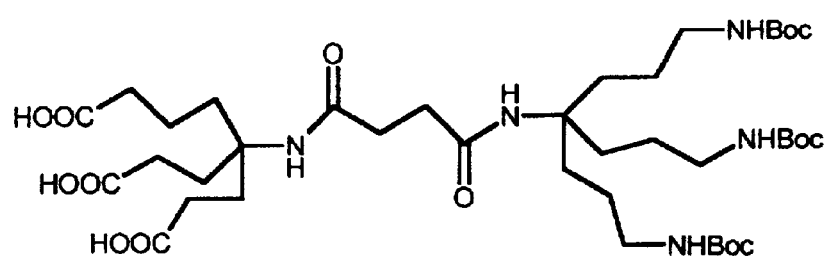
Figure 17B:
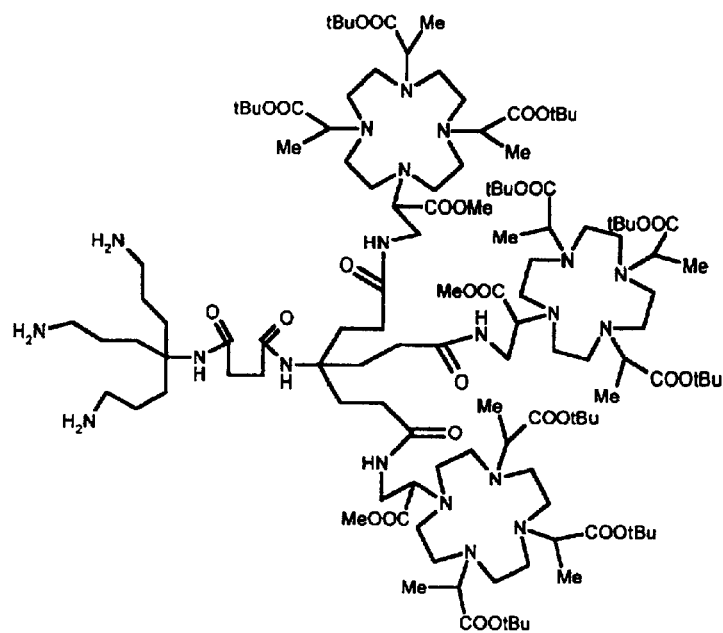
Figure 17B:
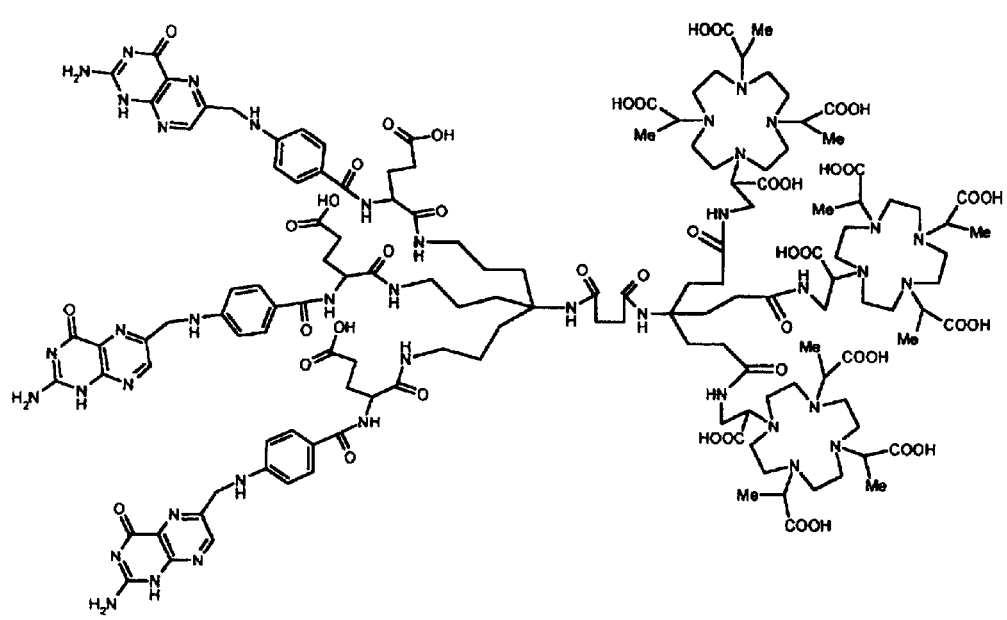

The linking molecule viz., the protected amino tricarboxylic ester 44, that is necessary for this preparation was made as shown in FIGS. 17 and 17A. The nitro-tris-t-butyl ester 37 was reduced to the corresponding amino-tris-t-butyl ester by catalytic hydrogenation using Raney Ni catalyst and then protected as the Z derivative to obtain the tris-t-butyl ester 43. Trifluoroacetic acid deprotection furnished the Z protected mono-amino-tris-carboxylic acid 44.

Coupling of the tris-acid 44 with the enhanced relaxivity ligand 15b, deprotection of the amino group by catalytic hydrogenolysis, and further coupling with the γ-tBu protected glutamate derivative 7 will give the protected glutamide 45.

Removal of the Z group in compound 45, further coupling with the pteroic acid derivative 4, and deprotection employing successively piperidine, aqueous base, and finally TFA will afford the desired multimeric folate conjugate 46. The corresponding γ folate analog can be made starting from the α protected glutamate derivative ZNH-E-(OtBu) (1).

A multimeric folate conjugate with enhanced relaxivity ligands in which three folate moieties are linked to three ligand moieties could be prepared from the 3:3 linker 39, described above. Compound 39 could be subjected to catalytic hydrogenation in the presence of Pd/C to obtain the tris-acid 47.

Coupling with three equivalents of ligand 15b, followed by selective deprotection of the BOC groups in the presence of t-Bu esters, as described by F. S. Gibson et al., J. Org. Chem. 1994, 59, 3216–3218, will provide the tris amine 48.

Coupling of the tris-amine 48 with 7, deprotection of the amino group, coupling with three equivalents of the pteroic acid derivative (4), and deprotection, employing successively piperidine, aqueous base, and finally TFA, will afford the desired multimeric folate conjugate 49. The corresponding γ folate analog can be made starting from the -α-protected glutamate derivative ZNH-E-(OtBu) (1).

(iv) Alternate Molecular Designs for Folate Conjugated Polyaza Macrocyclic Ligands The methods provided for the monomeric and multimeric folate conjugates of enhanced relaxivity ligands are by way of examples only. It is understood that other multimers of different ratios of folate to the ligand and of higher generations could be made by the methods described that are well known to those skilled in the art and they all will fall within the scope of the present invention. These new conjugates are intended for the MRI imaging of tumors that over-express the folate binding protein.

To increase the [Gd] at the folate site in vivo it is also possible to visualize multimers other than those based on the dendrimeric linkers presented above. For example the Gd chelate can be incorporated into naturally occurring or unnatural amino acids carrying linkable functionalities such as carboxy or amino groups. These chelate bearing amino acids can be converted into peptides by methods well known to those familiar with peptide synthesis. The fenestrae of the capillaries will allow a size of up to about decameric Gd chelate polymers as linear polymers and about the same size as cyclic or globular polymers.

Specifically Gd chelates containing the amino acid building blocks as free amino acids attached to, for example, Gd(R-DO3A) where R contains a Gd-binding oxygen atom capable of forming a five membered chelate ring with one nitrogen of the DO3A macrocycle, and a free amino acid, can be synthesized into multimers of from 5 to 20 units, with about 10 units being preferred, using an automated amino acid synthesizer such as an Advanced Chemtech 57. The terminal amino acid may be conjugated to the folate in the ways presented elsewhere herein. For cyclic peptides a lysine is inserted (unconjugated with Gd chelate, and the gamma amino group of the lysine can contain the folate targeting vector. Such bifunctional peptides are also part of this invention.

3. Detailed Description of the Oxa-PnAO Ligands and their Folate Conjugates

For imaging of tissues that overexpress folate binding protein using nuclear medicine techniques, ligands that can chelate 99 m-technetium are preferred, as this radioisotope has imaging characteristics that are optimal for detection by commercially available gamma cameras. Experiments from our laboratories on the cellular uptake of folate conjugates of technetium (Tc) chelates using KB cells indicate that, surprisingly, localization of such conjugates in tumors that overexpress folate binding protein is feasible using either the α- or γ-isomer of oxa-PnAO folate. Radioimaging studies with these compounds in folate-deprived tumor-bearing mice showed good localization of the alpha derivative in tumor and kidneys, with negligible uptake by liver. Detailed description of these chelates and methods for their synthesis are now described.

A. General Structures for Oxa-PnAO Ligand Intermediates for Conjugation Conjugated Folate Moieties The structures disclosed are further modifications of ligand motifs that were described by Ramalingam et al. in U.S. Pat. No. 5,627,286. The aim of making the modifications is to enable conjugation to targeting vectors such as folates. Derivatives of these intermediates wherein folic acid and methotrexate are coupled to these ligands through the alpha carboxylate have the general formulae IIIa, IIIb, and IIIc:

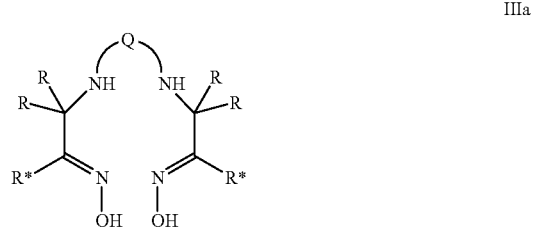

IIIa

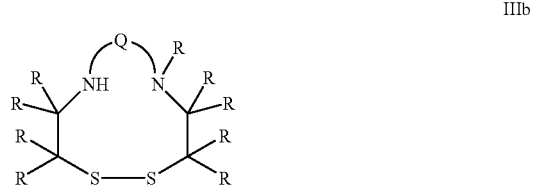

IIIb

-continued

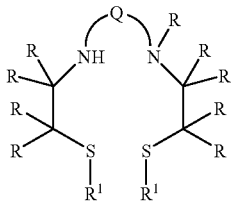
IIIc wherein Q is the group —(C(RR))$_{m1}$—Y$^1$ (C(RR))$_{m2}$—(Y$^2$—(C(RR))$_{m3}$)$_n$—, wherein
Y$^1$ and Y$^2$ are independently —CH$_2$—, —NR—, —O—, —S—, —SO—, —SO$_2$— or —Se—;
n is 0 or 1; and m1, m2 and m3 are integers independently selected from 0 to 4, provided that the sum of m1 and m2 is greater than zero;
all R and R* groups are independently —R$^4$, —Cl, —F, —Br, —OR$^5$, —COOR$^5$, —CON(R$^5$)$_2$, —N(R$^5$)$_2$, -alkyl-COOR$^5$, -alkyl-C(O)—N(R$^5$)$_2$; -alkyl-N(R$^5$)$_2$; —C(O)—OR$^5$; —C(O)—N(R$^5$)$_2$; -aryl-N(R$^5$)$_2$; acyl; acyloxy; heterocyclo; hydroxyalkyl; —SO$_2$—R$^5$; -alkyl-SO$_2$—R$^5$; or —[R$^3$], or
two R groups, or an R group and an R* group, taken together with the one or more atoms to which they are bonded, form a saturated or unsaturated, spiro or fused, carbocyclic (such as fused 1,2-phenyl) or heterocyclic ring which may be unsubstituted or substituted by one or more groups R or R* groups above,
with the proviso that a carbon atom bearing an R group is not directly bonded to more than one heteroatom; and that at least one R or R* is, or contains a folate-receptor binding radical —[R$^3$] of formula IV:

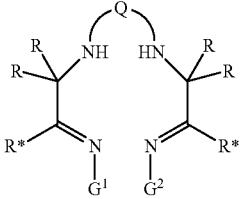
IV wherein R$_0$ is a folate-receptor binding residue of formula:

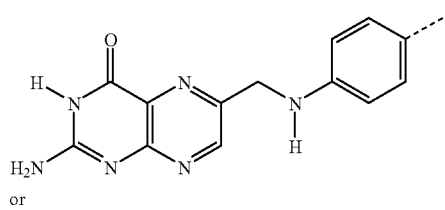

or

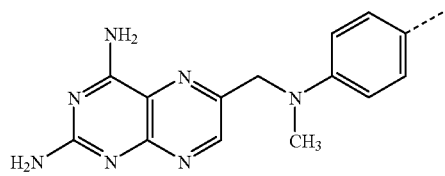

and where each X is independently —O—, —S—, —NH— or —N(R$_2$)—;

K$_2$ is —H, -alkyl, -alkenyl, -alkynyl, -alkoxy, -aryl, -alkyl, —CON(R$_2$)$_2$, -glutamate, or -polyglutamate;
A is a linking group; and p is 0 or a positive integer;
R$^1$ is hydrogen, a thiol protecting group, or the group —R$^3$ defined above; and
R$_2$ is independently hydrogen, alkyl, alkenyl, alkynyl, or aryl.
with the proviso that a carbon atom bearing an R group is not directly bonded to more than one heteroatom;

Folate conjugates of hydrazone-containing ligands having the structure disclosed in U.S. Pat. No. 5,651,954, incorporated herein by reference, are also useful for the preparation of metal complexes of the present invention.

The ligands have the following formula V:

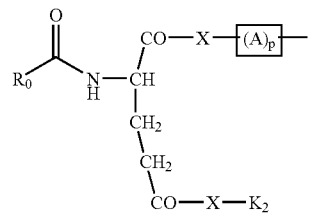
V wherein
Q is the group —(C(RR))$_{m1}$—(Y$^1$)$_n$—(C(RR))$_{m2}$—(Y$^2$—(C(RR))$_{m3}$)$_{n1}$;
Y$^1$ and Y$^2$ are each independently —CH$_2$—, —NR—, —O—, —S—, —SO—, —SO$_2$— or —Se—;
n and n1 are each independently 0 or 1; and m1, m2 and m3 are independently 0 or an integer from 1 to 4; provided that m1 and m2 are not both 0, that m1+m2+n+n1 is less than 6 and that a carbon atom bearing an R group is not directly bonded to more than one heteroatom;
each R and R* group is independently: R$^1$; -alkoxy; -hydroxy; -halogen, especially fluoro; -haloalkyl; —OR$^1$; —C(O)—R$^1$; —C(O)—N(R$^1$)$_2$; —N(R$^1$)$_2$; —N(R$^1$)—COR$^1$; -alkyl-C(O)—N(R$^1$)$_2$; alkyl-N(R$^1$)$_2$—; -alkyl-N(R$^1$)—COR$^1$; -aryl-C(O)—OR$^1$; -aryl-C(O)—N(R$^1$)$_2$; aryl-N(R$^1$)$_2$—; -aryl-N(R$^1$)—COR$^1$; -nitrile; -acyl; -acyloxy; -heterocyclo; -hydroxyalkyl; alkoxyalkyl; hydroxyaryl; arylalkyl; —SO$_2$—R$^1$; -alkyl-SO$_2$—R$^1$; or —R$^3$,
each R$^1$ is independently hydrogen, alkyl, alkenyl, alkynyl or aryl; and one to three of R, R*, or R$^2$ is, or contains a folate-receptor binding radical —R$^3$ of formula IV; or
two R groups, or an R group and an R* group, taken together with the one or more atoms to which they are bonded, form a saturated or unsaturated, spiro or fused, carbocyclic (such as fused 1,2-phenyl) or heterocyclic ring which may be unsubstituted or substituted by one or more groups R or R* groups above;
each G$^1$ and G$^2$ is each independently —OH or —(NR$^2$)$_2$;
with the proviso that at least one of G$^1$ or G$^2$ is —(NR$^2$)$_2$, where each R$^2$ is independently hydrogen, alkyl, aryl, acyl or —R$^3$; and R$^3$ is a folate-receptor binding residue of formula IV:

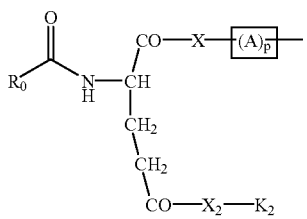

IV wherein $R_0$ is a folate-receptor binding residue of formula:

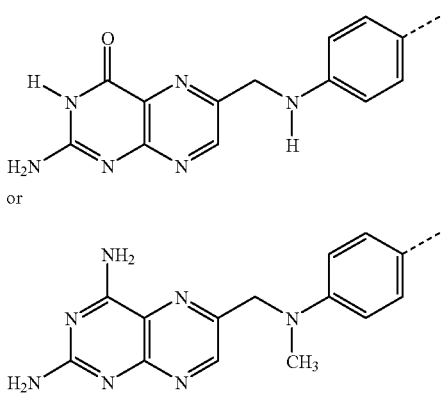

or each X is independently —O—, —S—, —NH— or —N($R_2$)—;

$K_2$ is —H, -alkyl, -alkenyl, -alkynyl, -alkoxy, -aryl, -alkyl, —CON($R_2$)$_2$, -glutamate, or -polyglutamate; wherein $R_2$ is independently hydrogen, alkyl, or aryl;

A is a linking group; and p is 0 or a positive integer.

Figure 18:
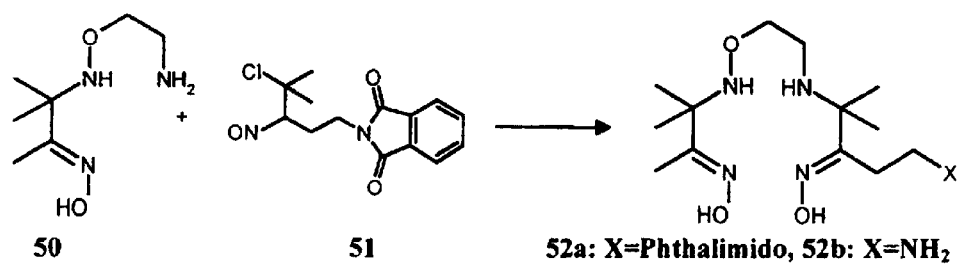
FIG. 18 shows the synthetic scheme for the preparation of the conjugable oxa-PnAO ligand 52b starting from the amine 50.

Folate-receptor binding derivatives of the following ligands are preferred:

3,3,9,9-tetramethyl-4,8-diazaundecane-2,10-dione 2-(2-phenylhydrazone)10-oxime;

3,3,9,9-tetramethyl-4,8-diazaundecane-2,10-dione 2-(2-benzoylhydrazone)10-oxime;

3,3,9,9-tetramethyl-4,8-diazaundecane-2,10-dione-bishydrazone; and 3,3,6,8-tetramethyl-4,8-diazaundecane-2,9-dione 2-(2-phenylhydrazone)9-oxime;

B. Methods for the Preparation of Folate Conjugates with Oxa-PnAO Ligands (i) Preparation of Conjugatable Oxa-PnAO Ligands The conjugatable oxa-PnAO ligand 52b was prepared starting from the amine 50 as depicted in FIG. 18. The amine 50 was made as described by Ramalingam et al. (loc. cit.). Alkylation of 50 by the chloro compound 51 in the presence of diisopropylethyl amine in dimethylformamide gave the phthalimido derivative 52a. Deprotection with hydrazine in dichloromethane afforded the conjugatable amino group-bearing oxa-PnAO ligand 52b.

Figure 19:
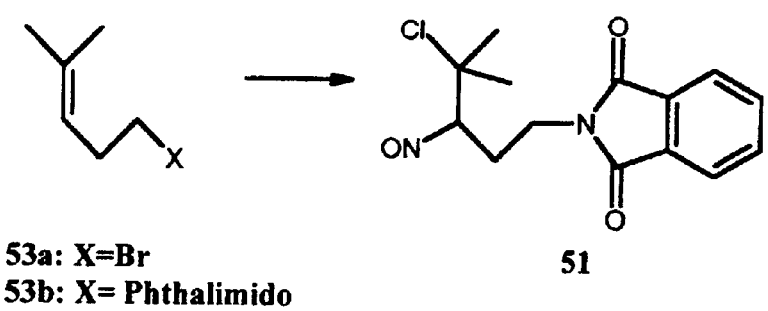
FIG. 19 shows the synthetic scheme for the preparation of the alkylating agent 51.

The alkylating agent 51 was prepared as shown in FIG. 19. Potassium phthalimidate was alkylated with 1-bromo-4-methyl-3-pentene (53a) in dimethylformamide at 90° C. to obtain the phthalimido derivative 53b. Addition of isoamylnitrite to the olefin in concentrated hydrochloric acid afforded the chloronitroso compound 51.

Figure 20:
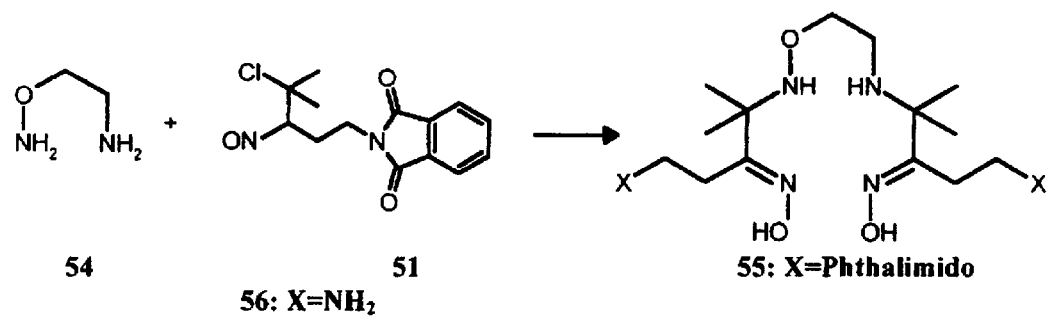
FIG. 20 shows the synthetic scheme for the preparation of the oxa-PnAO ligand 56 bearing two amino groups.

The oxa-PnAO ligand 56 bearing two amino groups could be prepared as shown in FIG. 20. The diamine 54 has been described by Ramalingam et al. (loc. cit.). Bis-alkylation of 54 by the chloro derivative 51 is expected to afford the bis-phthalimido derivative 55. Deprotection with hydrazine will provide the oxa-PnAO ligand 56.

ii) Preparation of Folate Conjugates with the Conjugatable Oxa-PnAO Ligands

Figure 21:
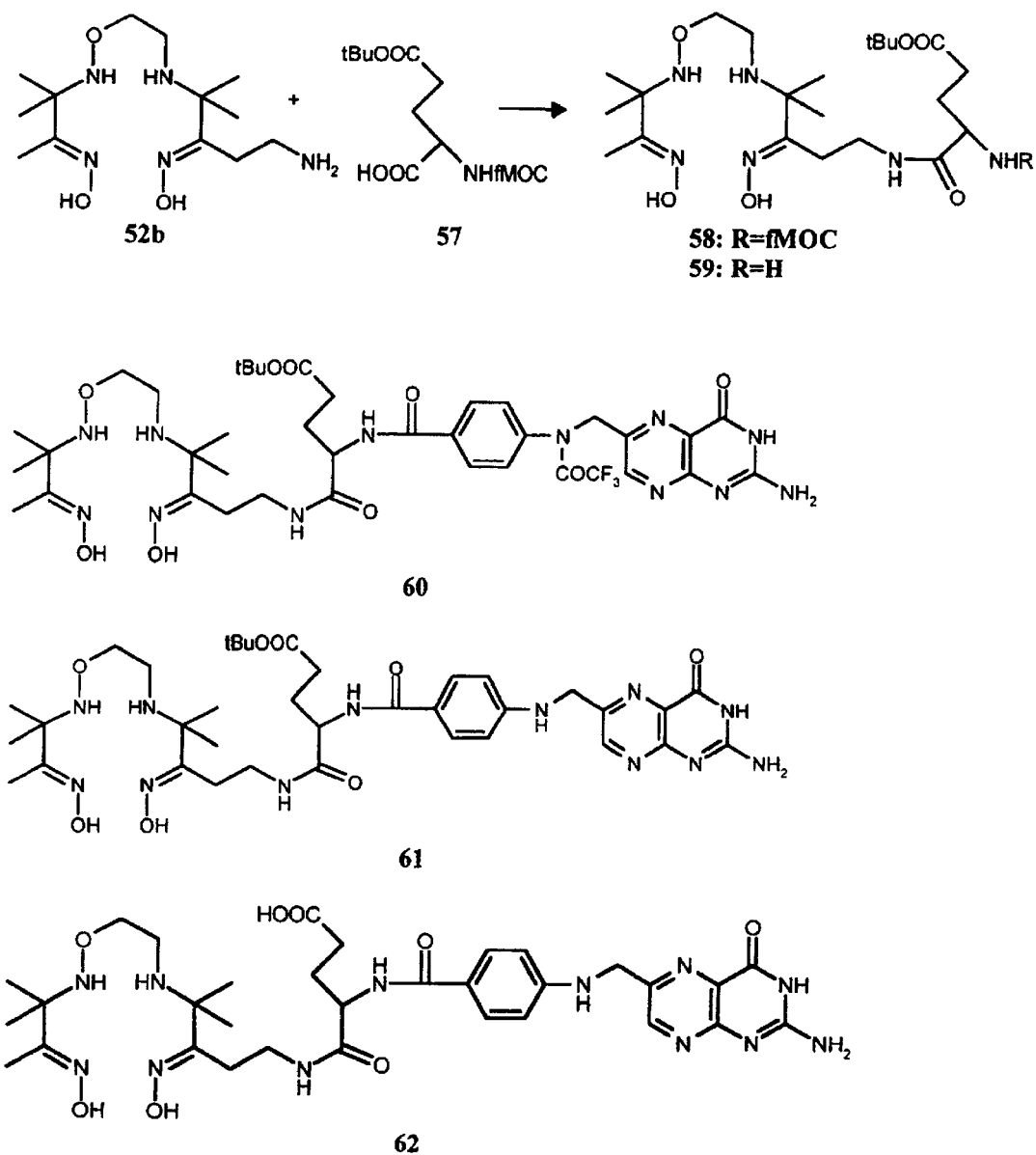
FIG. 21 shows the synthetic scheme for the preparation of the $\alpha$-folate conjugate 62 of the amino group-bearing oxa-PnAO ligand 52b.

The α folate conjugate 62 of the amino group-bearing oxa-PnAO ligand 52b was prepared as shown in FIG. 21. Coupling ligand 52b with the γ-protected glutamate derivative fMOC—NH—E(OtBu)—OH (57) using DCC/HOBT in dimethylformamide provided the glutamate derivative 58. Deprotection with piperidine in acetonitrile gave the amine 59.

Coupling of 59 with the pteroic acid derivative 4 using HOBT/DCC resulted in the protected conjugate 60. Deprotection with piperidine gave the product 61. Further deprotection furnished the desired folate conjugate ligand 62.

Figure 22:
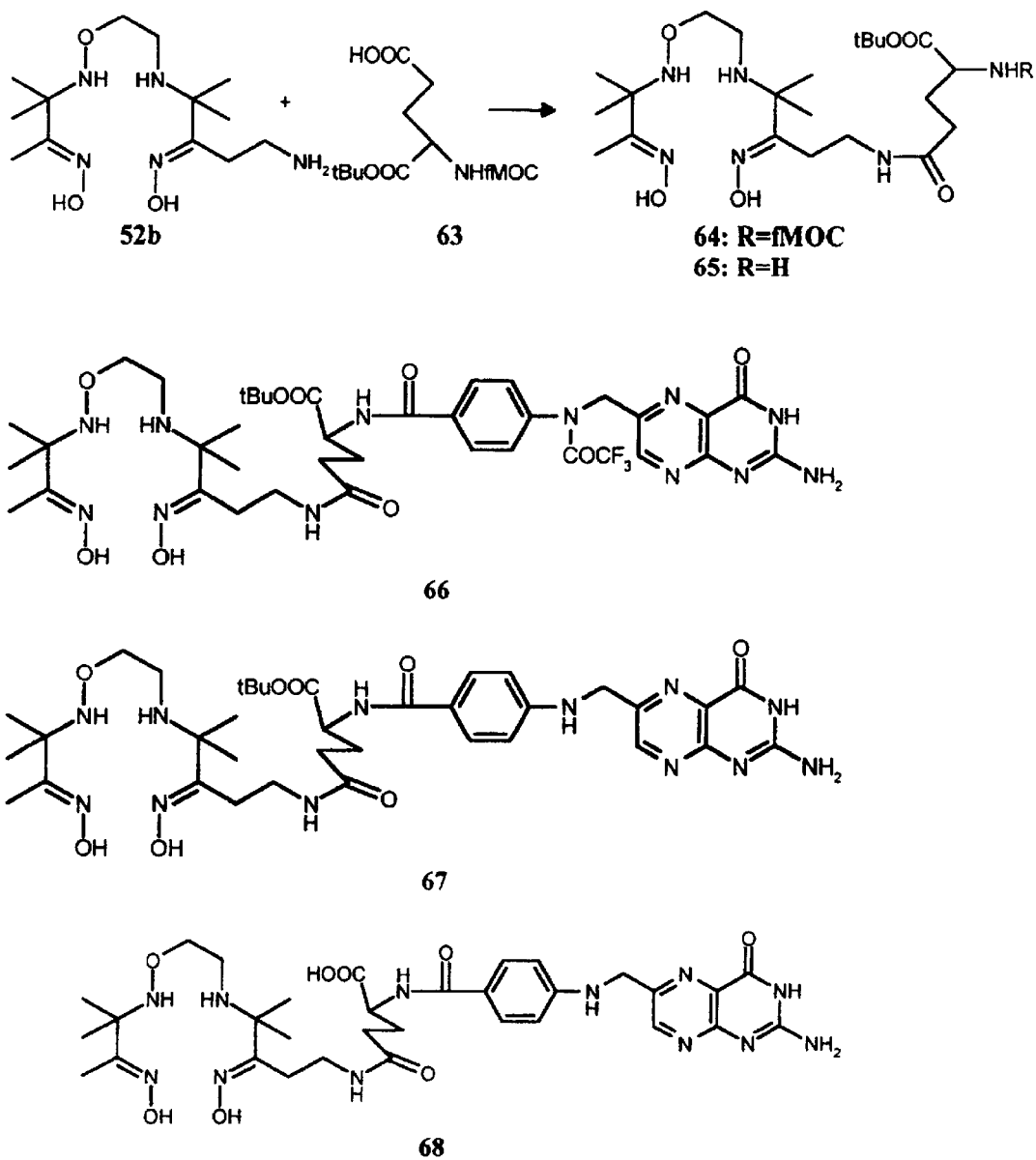
FIG. 22 shows the synthetic scheme for the preparation of gamma folate conjugate 64.

The corresponding gamma folate conjugate 64 was prepared by a similar approach starting from the alpha protected glutamate derivative fMOC—NH—E—(OtBu) (63) as shown in FIG. 22.

Coupling ligand 52b with the oc-protected glutamate derivative fMOC—NH—E(OtBu)—OH (63) using DCC/HOBT in dimethylformamide provided the glutamate derivative 64. Deprotection with piperidine in acetonitrile gave the amine 65. Coupling of 65 with the pteroic acid derivative 4 using HOBT/DCC resulted in the protected conjugate 66. Deprotection with piperidine gave the product 67. Further deprotection furnished the desired folate conjugate ligand 68.

iii) Preparation of Multimeric Folate Conjugates with the Oxa-PnAO Ligands

Conjugates in which more than one folate residue is attached to the oxa-PnAO ligand could be useful since multiple sites of recognition could provide for stronger binding and higher internalization into cells that overexpress the folate receptor. Such ligands could be prepared from the oxa-PnAO ligand that bears two amino groups as in formula 56. Treatment of ligand 56 with the pteroic acid derivative 4 in the presence of DCC/HOBT, followed by successive deprotections, first with piperidine and then with trifluoroacetic acid is expected to furnish the bis α-folate conjugated oxa-PnAO ligand 69. The synthesis of the corresponding bis γ-folate- or mixed bis α-, γ-folate-conjugated oxa-PnAO analogs could be accomplished by similar methods that will be clear to those skilled in the art.

The methods provided for the folate conjugates of the oxa-PnAO ligands are intended for preparation of compounds for use in nuclear medicine and radiotherapy applications and are based on the general oxa-PnAO ligand class described in U.S. Pat. No. 5,608,110. In these ligands the folate side chain has been attached at the oxime carbon (C=NOH) furthest from the oxa moiety. However, analogs wherein the folate- or methotrexate-bearing side chain is attached at both oxime carbon atoms, as for example in formula 69, are also included in the present invention. Similar molecules wherein the CH$_2$—O—NH functionality is replaced by CH$_2$—NR—NH (aza-PnAOs) are included in the present invention. The latter ligand core is covered by U.S. Pat. No. 5,651,954, which is incorporated herein by way of reference.

4. Abbreviations/Definitions

DMF=Dimethylformamide
THF=Tetrahydrofuran
DCC=Dicyclohexylcarbodiimide
HOBT=Hydroxybenzotriazole
TFA=Trifluoroacetic acid
CH$_3$CN=Acetonitrile HATU=[O-(7-azabenzotriazol-1-yl)-1,1,3,3-tetramethyluronium hexafluorophosphate]

Z=Benzyloxycarbonyl

The terms "alkyl" or "alk" as used herein alone or as part of another group, denote optionally substituted, straight and branched chain saturated hydrocarbon groups, preferably having 1 to 12 carbons in the normal chain, most preferably lower alkyl groups. Exemplary unsubstituted such groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl and the like. Exemplary substituents include one or more of the following groups; halo, alkoxy, arylalkyloxy (e.g., benzyloxy), alkylthio, alkenyl, alkynyl, aryl, cycloalkyl, cycloalkenyl, hydroxy, carboxyl (—COOH), amino, alkylamino, dialkylamino, formyl, alkylcarbonyloxy, alkylcarbonyl, heterocyclo, aryloxy or thiol (—SH). Preferred alkyl groups are unsubstituted alkyl, haloalkyl, arylalkyl, aminoalkyl, alkylaminoalkyl, dialkylaminoalkyl, alkoxyalkyl, aryloxyalkyl, hydroxyalkyl and alkoxyalkyl groups.

The terms "lower alk" or "lower alkyl" as used herein denote such optionally substituted groups as described above for alkyl having 1 to 4 carbon atoms in the normal chain.

The term "alkoxy" or "alkylthio" denote an alkyl group as described above bonded through an oxygen linkage (—O—) or a sulfur linkage (—S—), respectively. The term "alkylcarbonyl", as used herein, denotes an alkyl group bonded through a carbonyl group. The term "alkylcarbonyloxy", as used herein, denotes an alkyl group bonded through a carbonyl group which is, in turn, bonded through an oxygen linkage.

The term "alkenyl", as used herein alone or as part of another group, denotes optionally substituted, straight and branched chain hydrocarbon groups containing at least one carbon to carbon double bond in the chain, and preferably having 2 to 10 carbons in the normal chain. Exemplary unsubstituted such groups include ethenyl, propenyl, butenyl, pentenyl, hexenyl, heptenyl, octenyl, nonenyl, decenyl, and the like. Exemplary substituents include one or more alkyl groups as described above and/or one or more groups described above as alkyl substituents.

The term "alkynyl", as used herein alone or as part of another group denotes optionally substituted, straight and branched chain hydrocarbon groups containing at least one carbon to carbon triple bond in the chain, and preferably having 2 to 10 carbons in the normal chain. Exemplary unsubstituted such groups include ethynyl, propynyl, butynyl, pentynyl, hexynyl, heptynyl, octynyl, nonynyl, decynyl, and the like. Exemplary substituents include one or more alkyl groups as described above, and/or one or more groups described above as alkyl substituents.

The term "cycloalkyl", as used herein alone or as part of another group denotes optionally substituted, saturated cyclic hydrocarbon ring systems, preferably containing 1 to 3 rings and 3 to 7 carbons per ring. Exemplary unsubstituted such groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, and/or one or more groups described above as alkyl substituents.

The term "cycloalkenyl", as used herein alone or as part of another group, denotes such optionally substituted groups as described above for cycloalkyl, further containing at least one carbon to carbon double bond forming a partially unsaturated ring. Exemplary substituents include one or more alkyl groups as described above, and/or one or more groups described above as alkyl substituents.

The terms "ar" or "aryl", as used herein alone or as part of another group, denote optionally substituted, homocyclic aromatic groups, preferably containing 1 or 2 rings and 6 to 12 ring carbons. Exemplary unsubstituted such groups include phenyl, biphenyl, and naphthyl. Exemplary substituents include one or more, preferably three or fewer, nitro groups, alkyl groups as described above, and/or one or more groups described above as alkyl substituents. Preferred aryl groups are unsubstituted aryl and hydroxyaryl.

The term "carbocyclic", as used herein alone or as part of another group, denotes optionally substituted saturated, partially unsaturated or aromatic homocyclic hydrocarbon ring systems such as the cycloalkyl, cycloalkenyl or aryl groups described above.

The terms "heterocyclo" or "heterocyclic", as used herein alone or as part of another group, denote optionally substituted fully saturated or unsaturated, aromatic or non-aromatic cyclic groups having at least one heteroatom in at least one ring, preferably monocyclic or bicyclic groups having 5 or 6 atoms in each ring. The heterocyclo group may, for example, have 1 or 2 oxygen atoms, 1 or 2 sulfur atoms, and/or 1 to 4 nitrogen atoms in the ring. Each heterocyclo group may be bonded through any carbon or heteroatom off the ring system. Preferred groups include those of the following formula, which may be bonded through any atom of the ring system:

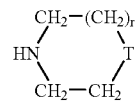

wherein r is 0 or 1 and T is —O—, —S—, —N—$R^8$ or —CH—$R^8$ where $R^8$ is hydrogen, alkyl arylalkyl. Exemplary heterocyclo groups include the following: thienyl, furyl, pyrrolyl, pyridyl, imidazolyl, pyrrolidinyl, piperidinyl, azepinyl, indolyl, isoindolyl, quinolinyl, isoquinolinyl, benzothiazolyl, benzoxazolyl, benzimidazolyl, morpholinyl, piperazinyl, 4-alkylpiperazinyl, 4-alkylpiperidinyl, 3-alkylpyrrolidinyl, oxazolyl, pyrazolyl, thiophenyl, pyridazinyl, thiazolyl, triazolyl, pyrimidinyl, 1,4-dioxanyl, benzoxadiazolyl, and benzofurazanyl. Exemplary substituents include one or more alkyl groups as described above and/or one or more groups described above as alkyl substituents.

The terms "halogen", "halo" or "hal", as used here in alone or as part of another group, denote chlorine, bromine, fluorine and iodine.

The term "acyl", as used herein alone or as part of another group, denotes the moiety formed by removal of the hydroxyl group from the group —COOH of an organic carboxylic acid. Exemplary such groups include alkylcarbonyl, arylcarbonyl, or carbocyclo- or heterocyclo-carbonyl. The term "acyloxy", as used herein alone or as part of another group, denotes an acyl group as described above bonded through an oxygen linkage (—O—).

The term "linking group" as used herein, denotes a group which, alone or together with one or more other groups, covalently bonds a folate receptor binding analog of folic acid to the remainder of a compounds of the present invention.

The term biomolecule as used herein, denotes a "bioactive moiety" such as folate, which is capable of being preferentially taken up at a selected site of a subject by possessing an affinity for the folate binding protein.

5. Detailed Description of the Methods for Metal Complexation

In preparing the compositions of the present invention, the folate receptor-binding moiety is coupled to a metal-chelating ligand moiety, which is complexed with the metal to form a metal chelate. Alternatively, in MRI applications, the ligand may be complexed with a metal, and subsequently conjugated with the folate receptor-binding moiety. The ligands disclosed in (A), (B) and (C) above are complexed with an appropriate metal for the imaging or therapeutic method envisioned. This may be accomplished by methodology known in the art. For example the metal can be added to water in the form of an oxide or in the form of a halide or acetate and treated with an equimolar amount of the ligand molecule. The ligand molecule can be added as an aqueous solution or suspension. Dilute acid or base can be added (where appropriate) to maintain a suitable pH. Heating at temperatures as high as 100° C. for period of up to 24 hours or more may sometimes be employed to facilitate complexation, depending on the metal and the chelator, and their concentrations.

In the examples below, metal chelate synthesis will be illustrated by gadolinium (Gd) and technetium (Tc) complex synthesis. However, it is to be understood that analogous processes can be used to prepare other metal chelate complexes.

More particularly, the method of forming the metal complexes derivatized with folate according to the present invention comprises the following steps.

A metal complex or salt in the desired oxidation state and containing an easily displaceable ligand or ligands (i.e., labile ligands such as $H_2O$, Cl, $NO_3$, or acetate) is mixed with the ligand of the present invention at a pH value suitable for forming the desired complex. The labile ligand is displaced from the metal by the ligands of the present invention to form the metal complexes of the present invention. Illustrative of such methods are the following:

$$MX_3 + LH_3 \rightarrow ML + 3HX \quad (1)$$

wherein

X is Cl, Br, F, $NO_3$; or acetate; and

M is metal such as Gd or Indium in the desired oxidation state;

$$MOCl_4 + LH_2 \rightarrow MOL + 2HCl + 2Cl \quad (2a)$$

$$MO_2(R_4)^{(-/0/+)} + LH_2 \rightarrow MO_2L + 4R^- + 2H^+ \quad (2b)$$

wherein

R is a monodentate ligand, such as pyridine, halogen, phosphine or amine; and

M is a metal such as an isotope of technetium or rhenium;

$$MR_2 + LH_2 \rightarrow ML + 2RH + 2H^+ \quad (3a)$$

$$MOR_2 + LH_2 \rightarrow MOL + 2RH + 2H^+ \quad (3b)$$

wherein

R is a bidentate ligand, such as a sugar, a diol, bis amine or bipyridine; and

M is a metal.

Alternatively, for radiopharmaceutical and radiotherapy applications the metal complexes of the present invention can be prepared from a metal in an oxidation state different from that of the desired complex. In this case, either a reducing agent or an oxidizing agent, (depending on the oxidation state of the metal used and the oxidation state of the desired final product) must be added to the reaction mixture to bring the metal to the desired oxidation state. The oxidant or reductant can be used to form an intermediate complex in the desired oxidation state but with labile ligands. These labile ligands can then be displaced by the desired chelating ligand of the present invention. Alternatively, the labile ligands can be added to the reaction mixture along with the reductant or oxidant and the desired ligand to achieve the change to the desired oxidation state and chelation to the desired metal in a single step.

Also in accordance with the present invention, a method for diagnostic examination or therapeutic treatment of a mammal is provided. This method is based on the mechanism of receptor-mediated endocytosis activity and involves i) the movement of a folate receptor binding moiety, conjugated through its alpha or gamma carboxylate to a chelated radioactive or non-radioactive metal that can be detected by external imaging techniques, or ii) the movement of a folate receptor binding moiety conjugated through its alpha carboxylate to a chemotherapy agent, into the interior of a cell through invagination of the cell membrane. The folate receptor binding moiety serves to deliver the chelated metal or a chemotherapy agent into cells that overexpress folate binding protein, thereby enabling diagnostic examination, radiotherapy or chemotherapeutic treatment of an organ or tissue comprising the cells.

In one aspect the method of the present invention comprises the steps of (a) administering to a mammal a composition comprising a paramagnetic or superparamagnetic metal complexed with a chelating ligand and coupled to a folic acid analog contained in a pharmaceutically acceptable carrier and (b) monitoring the biodistribution of the metal.

In another aspect the method of the present invention comprises the steps of administering to a mammal a composition comprising a radioactive metal complexed with a chelating ligand coupled to a folic acid analog contained in a pharmaceutically acceptable carrier for radiotherapeutic treatment of said mammal and monitoring said treatment.

In still another aspect the method of the present invention comprises the steps of administering to a mammal a composition comprising a chemotherapeutic agent, with or without the presence of a radioactive metal, complexed to a folic acid analog contained in a pharmaceutically acceptable carrier for chemotherapy treatment of said mammal and monitoring said treatment.

In the compositions of the present invention a folic acid analog, carrying the metal-chelate complex or the chemotherapeutic agent, binds to folate binding protein on cell membranes, followed by internalization.

(a) Paramagnetic Metals

Paramagnetic metals are used in affecting the relaxation times of nuclei in mammalian tissue. Certain atomic nuclei, in particular, protons, orient themselves as a result of a strong magnetic field that is applied to them in MR imaging. The pulses of a given radio frequency, or resonance frequency, move the atomic nuclei out of a state of equilibrium. The nuclei then return to their original state of equilibrium as a result of spin-spin and spin-lattice relaxation. The time required for returning to the state of equilibrium, known as relaxation time, gives valuable information on the degree of organization of the atoms and on their interaction with their environment.

On the basis of differences in proton density and relaxation times, images of biological tissues can be obtained which may be used for diagnostic purposes. The greater the differences in the relaxation times of the nuclei which are present in the tissues being examined, the greater will be the contrast in the image that it obtained.

It is known that the relaxation times of neighboring nuclei can be affected by the use of paramagnetic salts. In solution, the paramagnetic salts are toxic in mammals. Hence, to reduce the toxic effect of paramagnetic metal ions administered for diagnostic purposes, they are combined with complex compounds, i.e. complexing agents. Constituting a part of the present invention, the paramagnetic metals are complexed with ligand moieties prior to, or subsequent to, complexation with folates. The folate complexed with metal chelates increases the concentration of the metal that contains high levels of FBP in cells, thus providing increased contrast of the tissue comprising the cells.

The paramagnetic metals used in the composition for MR imaging include the elements having atomic numbers of 22 to 29, 42, 44 and 58–70. Examples of such metals are chromium (III), manganese (II), iron (II), iron (III), cobalt (II), nickel (II), copper (II), praseodymium (III), neodymium (III), samarium (III), gadolinium (III), terbium, (III), dysprosium (III), holmium (III), erbium (III) and ytterbium (III). Chromium (III), manganese (II), iron (III) and gadolinium (III) are particularly preferred.

Doses for administration of paramagnetic metals in the complex of the present invention are from about 0.05 to about 0.3 mmol/kg of body weight.

The metal complexes of the present invention find utility as diagnostic and/or therapeutic agents. Thus, the present invention provides methods for the diagnosis of the presence and/or status of a disease state, or for the treatment of a disease state, comprising the step of administering a metal complex of the present invention to a subject in need thereof. The metal complexes of the present invention may be administered by an appropriate route such as orally, parentally (for example, intravenously), intramuscularly or intraperitoneally or by any other suitable method. For example, the complexes of this invention may be administered to a subject by bolus or slow infusion intravenous injection.

(b) Radioactive Metals

In the embodiment of the present invention directed to radiographic imaging or radiotherapy, radioisotopes are utilized. Preferred radioisotopes include: $^{99m}$Tc, $^{51}$Cr, $^{67}$Ga, $^{68}$Ga, $^{111}$In, $^{168}$Yb, $^{140}$La, $^{90}$Y, $^{88}$Y, $^{153}$Sm, $^{156}$Ho, $^{165}$Dy, $^{64}$Cu, $^{97}$Ru, $^{103}$Ru, $^{186}$Re, $^{188}$Re, $^{203}$Pb, $^{211}$Bi, $^{212}$Bi, $^{213}$Bi and $^{214}$Bi. The choice of metal ion will be determined based on the desired therapeutic or diagnostic application.

The amount of radiopharmaceutical administered may be selected based on the desired use, such as to produce a diagnostic image of an organ, by methods known in the art. Doses may range from about 2 to 200 mCi, or as limited by the in vivo dosimetry provided by the radiopharmaceuticals. The radiopharmaceutical may optionally be co-administered with a metal-free ligand of the folic acid derivatives of the present invention which derivative is present in an amount of from about 0.05 mg to about 200 mg per dose.

6. General Description of the Conjugation of Folates with Chemotherapeutic Agents In this embodiment the present invention comprises a chemotherapeutic compound complexed with a folate receptor-binding ligand through its alpha carboxylate or its alpha and gamma carboxylate functionality, which on administration to a patient, is capable of selectively enhancing the transport of the chemotherapeutic agent across the membrane of cancer cells that overexpress FBP and decreasing the uptake to non-target organs, thereby facilitating treatment of the tumor being targeted.

Chemotherapeutic agents useful in neoplastic disease are listed, for example, in Goodman & Gilman's *The Pharmacological Basis of Therapeutics*, 6$^{th}$ Ed., 1980, MacMillan Publ. Co., N.Y., pp. 1252–1254, *The Merck Index*, 11$^{th}$ Ed. 1989, which are incorporated herein by reference. These chemotherapeutic agents include:

Alkylating Agents
    Alkyl Sulfonates, such as
        Busulfan,
        Improsulfan, and
        Piposulfan,
    Aziridines, such as
        Benzodepa,
        Carboquone,
        Meturedepa, and
        Uredepa
    Ethylenimines and Methylmelamines
        Altretamine,
        Triethylenemelamine,
        Triethylenephosphoramide,
        Triethylenethiophosphoramide, and
        Trimethylolmelamine
    Nitrogen Mustards, such as
        Chlorambucil,
        Chlomaphazine,
        Cyclophosphamide,
        Estramustine,
        Ifosfamide,
        Mechlorethamine,
        Mechlorethamine Oxide Hydrochloride,
        Melphalan,
        Novembichin,
        Phenesterine,
        Prednimustine,
        Trofosfamide and
        Uracil Mustard
    Nitrosoureas, such as
        Carmustine,
        Chlorozotocin,
        Fotemustine,
        Lomustine,
        Nimustine, and
        Ranimustine
    Antibiotics, such as
        Aclacinomycins,
        Actinomycin $F_1$,
        Anthramycin,
        Azaserine,
        Bleomycins,
        Cactinomycin,
        Carubicin,
        Carzinophilin,
        Chromomycins,
        Dactinomycin,
        Daunorubicin,
        Doxorubicin,
        Epirubicin,
        Mitomycins,
        Mycophenolic Acid,
        Nogalamycin,
        Olivomycins,
        Peplomycin,
        Plicamycin,
        Porfiromycin,
        Puromycin,
        Streptonigrin,
        Streptozocin,
        Tubercidin,
        Ubenimex, Zinostatin, and
Zorbucin Antimetabolites, such as
Fludarabine,
6-Mercaptopurine,
Thiamiprine,
Thioguanine,
Ancitabine,
Azacitidine,
6-Azauridine,
Camofur,
Cytarabine,
Doxifluridine,
Enocitabine,
Floxuridine,
Fluorouracil,
Tegafur, and
L-Asparaginase Antineoplastic (Hormonal)
Androgens, such as
Calusterone
Dromostanolone Propionate,
Epitiostanol,
Mepitiostane and
Testolactone Antiadrenals, such as
Aminoflutethimide,
Mitotane, and
Trilostane Antiandrogens, such as
Flutamide and
Nilutamide Antiestrogens, such as
Tamoxifen and
Toremifene Estrogens, such as
Fosfestrol,
Hexestrol and
Polyestradiol Phosphate LH-RH Analogs, such as
Buserelin,
Goserelin,
Leuprolide and
Triptorelin Progestogens, such as
Chlormadinone Acetate,
Medroxyprogesterone
Megestrol Acetate, and
Melengestrol The therapeutic complexes of this invention may be administered to a mammal alone or in combination with pharmaceutically acceptable carriers, the proportion of which is determined by the chemical nature of the chemotherapeutic compound, chosen route of administration and standard pharmaceutical practice.

The physician will determine the most suitable dosage of the present therapeutic agents and it will vary with the form of administration and the particular compound chosen, and also, it will vary with the particular patient under treatment. Dose levels will be equal to or lower than those used with the chemotherapeutic compounds alone since the folate complex effectively delivers the chemotherapeutic compound into the tumor cells.

In chemotherapy the complexes of the present invention can be administered through intravenous, intramuscular or intraperitonal routes in a physiologically acceptable medium, such as saline or water that is buffered or pH adjusted using physiologically acceptable salts or buffers well-known in the art.

The complexes can be administered as a bolus by continuous infusion or given on alternative days determined by experimental methods which are well known to skilled chemotherapists.

7. Description of Kits for Forming Metal Complexes

For radiopharmaceutical or radiotherapy applications it is convenient to prepare the complexes of the present invention at, or near, the site where they are to be used. A single, or multi-vial kit that contains all of the components needed to prepare the complexes of this invention, other than the radionuclide ion itself, is an integral part of this invention.

The amount administered may be selected based on the desired use, such as to produce a diagnostic image of an organ or other site of a subject or a desired radiotherapeutic effect, by methods known in the art. Exemplary dosages are those employing about 2–200 mCi rhenium (for radiotherapy) or about 10–60 mCi technetium (for imaging). The "subject" of the methods of the present invention is preferably a mammal such as a domestic mammal, for example, a dog, cat, horse or the like, or most preferably, a human. Depending upon the metal and ligand used, the complexes of the present invention may be employed as, for example, imaging agents useful for imaging tissues or organs that overexpress folate binding protein, such as tumor cells, epithelial cells, kidneys, gastrointestinal or the hepatobiliary system.

Preferred complexes of the present invention are those comprising a ligand complexed with a radionuclide such as technetium, or rhenium.

Rhenium is particularly useful as a radiotherapy agent. The rhenium employed is preferably one of the radionuclides Re-186 or Re-188, or a mixture thereof, which mixture may also include Re-185 and/or Re-187. Preparation of the complexes of the present invention where the metal is rhenium may be accomplished using rhenium in the +5 or +7 oxidation state. Examples of compounds in which rhenium is in the Re(VII) state are $NH_4ReO_4$ or $KReO_4$. Re(V) is available as, for example, [$ReOCl_4$] ($NBu_4$), [$ReOCl_4$] ($AsPh_4$), $ReOCl_3$ ($PPh_3$) and as $ReO_2$ (pyridine)$_4$+. (Ph is phenyl; Bu is n-butyl). Other rhenium reagents capable of forming a rhenium complex may also be used.

Technetium is particularly useful as a diagnostic imaging agent. The technetium employed is preferably one or more of the radionuclides Tc-99m, Tc-94m or Tc-96. The preferred radioisotope for medical imaging is $^{99m}Tc$. Its 140 keV γ-photon is ideal for use with widely-available gamma cameras. It has short (6 hour) half like, which is desirable when considering patient dosimetry. $^{99m}Tc$ is readily available at relatively low cost through commercially-produced $^{99}Mo/^{99m}Tc$ generator systems. Preparation of the complexes of this invention where the metal is technetium may be accomplished using technetium in the form of the pertechnetate ion. For Tc-99m, the pertechnetate ion is preferably obtained from commercially available technetium-99m parent-daughter generators; such as technetium is in the +7 oxidation state. The generation of the pertechnetate ion using this type of generator is well known in the art, and is described in more detail in U.S. Pat. Nos. 3,369,121 and 3,920,995. These generators may generally be eluted with saline solution, and the pertechnetate ion obtained as the sodium salt. Pertechnetate may also be prepared from cyclotron-produced radioactive technetium using procedures well know in the art.

A preferred single-vial kit of the present invention comprises a ligand described in sections A, B or C, a folic acid derivative of the α-, γ- and bis isomers in a desired ratio, and a source of a pharmaceutically acceptable reducing agent such as a stannous salt. More preferably, in addition, the kit is buffered with a pharmaceutically acceptable acid or base to adjust the pH to a desired value for complex formation.

It is preferred that the kit contents be in lyophilized form. Such a single vial kit may optionally contain exchange ligands such as glucoheptonate, gluconate, mannitol, malate, citric or tartaric acid and may also contain reaction modifiers, such as diethylenetriaminepentaacetic acid or ethylenediamine tetraacetic acid. Additional additives, such as solubilizers (for example α-, β- or γ-cyclodextrin), anti-oxidants (for example ascorbic acid) and/or fillers (for example, NaCl) may be employed to improve the radiochemical purity and stability of the final product, or to aid in the production of the kit.

A preferred multi-vial kit of the present invention comprises, in one vial, the components, other than the radionuclide itself, required to form a labile radionuclide (especially Tc(V)) complex, that is, an exchange ligand and a pharmaceutically acceptable reducing agent such as a stannous salt. The quantity and type of exchange ligand, and amount and type of reducing agent and buffer used may be selected based on the nature of the exchange complex to be formed. The ligand described in A, B, C, D, or E, a folic acid derivative of the α, γ and bis isomers in a desired ratio of the present invention is contained in a second vial, as well as optional additives such as buffers appropriate to adjust the pH to its optimal value.

A single vial kit may be ready for use following addition of the radionuclide ion, such as pertechnetate. A multi-vial kit may be ready for use by addition of the radionuclide ion, such as pertechnetate, to the vial containing exchange ligand and reducing agent, and after waiting an appropriate period of time for formation of a labile complex, the contents of this vial are added to the second vial containing a source of the desired ligand. After a reaction time of about 1 to 60 minutes, the complex of the present invention is formed. It is advantageous that the contents of both vials of this multi-vial kit be lyophilized. As described for the single vial kit, additional additives may be employed to improve the radiochemical purity and stability of the final product, or to aid in the production of the kit.

Alternatively, the multi-vial kit may comprise the desired ligand in one vial and a source of reducing agent such as stannous ion in a second vial. Pertechnetate may be added to the vial containing ligand, and then the contents of the second vial added to initiate labeling. As above, the quantity and type of ligand, buffer pH and reducing agent may be selected based on the nature of the desired ligand use. Again, it is advantageous that the contents of both vials be lyophilized.

8. Examples
    A. Synthesis of Intermediates and Folate Conjugates

EXAMPLE 1

N-Pteroyl-γ-glutamyl-APADO3A (6) [DO3A-APA-(γ)-folate]

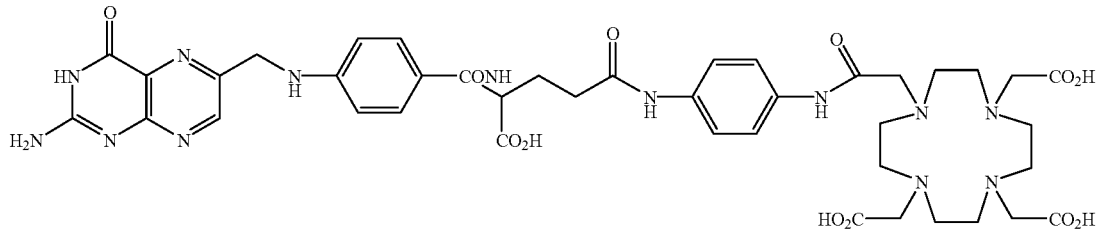

A) N-CBZ-α-t-butyl-L-glutamyl-APADO3A-tri-t-butyl ester (3)

To a cooled solution of N-CBZ-L-glutamic acid-α-t-butyl ester (1) (3.75 g; 11.1 mmol) in DMF (30.0 mL) were added HATU (5.25 g, 13.8 mmol) and diisopropylethylamine 4.45 g (34.4 mmol) and the mixture was stirred at RT for 15 min. APADO3A-tris-t-butyl ester (2) 6.0 g (9.1 mmol) was added and the reaction mixture was stirred at RT for 12 h. DMF was removed under vacuum and the residue was treated with water and extracted with ethyl acetate. The organic layer was washed with 10% NaOH (3×100 mL), water and dried ($Na_2SO_4$). Ethyl acetate was removed on a rotary evaporator and the thick oil obtained was chromatographed over silica gel ($CH_2Cl_2$:$CH_3OH$, 95:5). UV visible fractions were collected and the solvent was removed to give a viscous oil which was dried under vacuum to obtain a foamy solid. Yield 5.5 g (93%). MS: $(M+H)^+=982.7$.

B) L-glutamyl-α-t-butyl-APADO3A-tri-t-butyl ester (3a)

To a solution of N-CBZ-α-t-butyl-L-glutamyl-APADO3A-tri-t-butyl ester (3) (1.0 g; 4.6 mmol) in methanol (50.0 mL) was added 5% Pd-C (500 mg) and the mixture was hydrogenated (30 psi) for 12 h. Catalyst was removed by filtration and methanol was removed to give a colorless thick oil. It was dried under vacuum to afford a foamy solid. Yield 0.82 g (98%). MS: $(M+Na)^+=871$. HRMS (FAB) m/z, Calcd for $C_{43}H_{73}N_7O_{10}$ $(M+Na^+)$ 871.5395; Found: 871.5325.

C) N-($N^{10}$-trifluoroacetylpteroyl)-α-t-butyl-L-glutamyl-APADO3A-tris-t-butyl ester (5)

To a stirred, 0° C. slurry of $N^{10}$-trifluoroacetylpteroic acid (4) (0.204 g; 0.5 mmol) in dimethylformamide [DMF] was added hydroxybenzotriazole (0.092 g, 0.6 mmol). After 10 min dicyclohexylcarbodiimide [DCC] (0.125 g, 0.6 mmol) was added and the slurry was stirred at 0° C. for 1 h. To this suspension was added L-glutamyl-α-t-butyl-APADO3A-tri-t-butyl ester (3a) (0.45 g; 0.53 mmol) followed by diisopropylethylamine (0.13 g, 1 mmol). The reaction mixture was allowed to stir for 2 h at 0° C. and then 12 h at RT. DMF was removed under reduced pressure and the residue was treated with water. The light yellow solid formed was filtered and dried under vacuum. Trituration of the solid with hot ethyl acetate (3×50 mL) and removal of the solvent yielded a light yellow solid. The product was purified by silica gel column chromatography, eluting with $CH_2Cl_2$:$CH_3OH$ (95:5), to afford 0.25 g (40%) of the amide as a white solid. MS: $(M+H)^+=1238.5$. $(M+Na)^+=1260.4$.

D) N-Pteroyl-α-t-butyl-L-glutamyl-APADO3A-tris-t-butyl ester (5a)

To a solution of N-($N^{10}$-trifluoroacetylpteroyl)-α-t-butyl-L-glutamyl-APADO3A-tris-t-butyl ester (5) (0.31 g; 0.25 mmol) in DMF-water (4.5:0.5, 5 mL), piperidine (0.3 mL) was added and the solution was stirred at RT for 24 h. DMF-water were removed under vacuum to give a thick oil. The oil was treated with water (5 mL) and the precipitated yellow solid was filtered, dried under vacuum. Purification by silica gel column chromatography ($CH_2Cl_2$:$CH_3OH$, 95:5) yielded 0.47 g (72.0%). of N-Pteroyl-α-t-butyl-L-glutamyl-APADO3A-tris-t-butyl ester.

This compound was further purified by reverse phase HPLC (Vydac-C18, 10μ, 10×25 cm) with a linear gradient of 0.1% TFA in $H_2O$/$CH_3CN$ (0–60%) over sixty min to give 0.2 g of the product. MS: $(M+H)^+$=1143. HRMS (FAB) m/z, Calcd for $C_{57}H_{83}N_{13}O_{12}$ ($MH^+$) 1142.6379; Found: 1142.6362.

E) N-Pteroyl-γ-L-glutamyl-APADO3A (6)

N-Pteroyl-α-t-butyl-L-glutamyl-APADO3A-tris-t-butyl ester (5a) (0.16 g; 0.14 mmol), was dissolved in concentrated hydrochloric acid (0.3 mL) and stirred for 15 min. Absolute ethanol (3.0 mL) was added to the reaction mixture and the precipitated hydrochloride was centrifuged and the supernatant solution was decanted. The hydrochloride was suspended in ethanol (3.0 mL), stirred for 5 min, centrifuged, and decanted. The solid was treated in the same manner with two additional volumes of ethanol (3.0 mL ). The light yellow hydrochloride obtained was dried under vacuum. Yield 0.16 g. MS: $(M+H)^+$=918.

EXAMPLE 2

Gd-DO3A-APA-(γ)-folate mmoles) in 1.79 mL of 0.04M HCl was added and the solution was stirred under nitrogen at ~40° C. as the reaction mixture pH was gradually adjusted to pH 5.5 using 0.01N NaOH. After four hours, ethanol (50 mL) was added and the reaction mixture volume was reduced to 40 mL by rotary evaporation. Addition of ethanol (80 mL) caused the precipitation of an orange gel, which was isolated by centrifugation at 4° C. The pellet was rinsed with 20 mL of ethanol, and dried in vacuo to yield 35 mg of product. Anal. Calcd. for the Na salt of Gd-DO3A-APA-(γ)-folate $3H_2O.2EtOH.0.15NaCl$ ($C_{45}H_{66}N_{13}O_{17}GdNa.0.15NaCl$, MW=1253.04): Calcd: C, 43.13; H, 5.31; N, 14.53; Cl, 0.566. Found: C, 43.21; H, 4.96; N, 14.47; Cl, 0.56.

Alternatively, the isolated gel was dissolved in 10 mM $(NH_4)HCO_3$ and chromatographed on a DEAE Tris-acryl anion exchange column. Trace impurities were removed from the column by elution with 10 mM $(NH_4)HCO_3$ (200 mL). Product was then eluted from the column using a gradient of 10 mM to 100 mM ammonium bicarbonate, and fractions containing the compound were freeze-dried to give product that is consistent with the anhydrous formulation Na(Gd-DO3A-APA (γ) folate.$CO_3$. Anal Calcd. for $C_{42}H_{49}N_{13}O_{15}GdNa$, (mw=1156.19): Calc. C, 43.63; H, 4.27; N, 15.75. Found: C, 43.84; H, 4.10; N, 15.76.

EXAMPLE 3

$^{153}$Gd-DO3A-APA-(γ)-folate

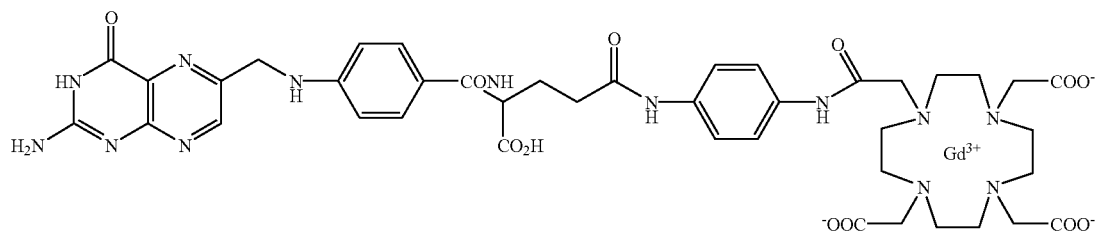

DO3A-APA-(γ)-folate ligand (6) (74 mg; 0.0685 mmoles) was suspended in 20 mL of water and adjusted to pH 5.5 with 26.5 mL of 0.01M NaOH. $GdCl_3.4H_2O$ (0.0716

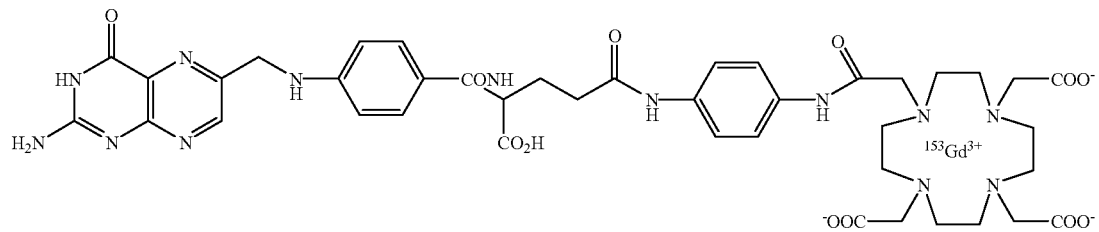

DO3A-APA-(γ)-folate ligand.3HCl.3H$_2$O (6) (10.13 mg, 0.00936 mmoles) was mixed with 7.5 mL of distilled water and adjusted to pH 5.86. A 1 ML aliquot of this solution (0.863 mg, 0.7975 μmol) was added to a 2-dram vial. A solution of GdCl$_3$.4H$_2$O (1.34 mg/mL) was prepared in dilute HCl. An 0.2 mL aliquot of this solution was mixed with 100 μCi of $^{153}$GdCl$_3$ in 0.5M HCl and then transferred to the ligand vial. The resulting solution was heated at 55° C. with stirring, and the pH was adjusted to 6.0 over 30 minutes using 0.1N NaOH. After 1.5 hours, the pH had fallen to 5.2 and $^{153}$Gd-DO3A-APA-(γ)-folate had formed in 96% yield as determined by radioisotope detection using HPLC on a Supelcosil LC-18 column (25 cm×4.6 mm) eluted with a step gradient of 0 to 40% acetonitrile/buffer A. (buffer A=1.0 mM tris buffer pH 7.25 containing 0.2 mM EDTA).

EXAMPLE 4

N-Pteroyl-α-L-glutamyl-APADO3A (10) [DO3A-APA-(α)-folate]

12 hours. The catalyst was removed by filtration on Celite and washed with methanol (3×10 mL). The combined methanolic solution was evaporated to a thick viscous oil. It was dried under vacuum to afford 1.6 g (92%) of L-glutamyl-γ-t-Butyl-APADO3A-tris-t-butylester 8a as a foamy solid. MS: (M+Na)$^+$=871. HRMS (FAB) m/z, Calcd for C$_{43}$H$_{73}$N$_7$O$_{10}$ (M+Na$^+$) 871.5395; Found: 871.5414.

C) N-(N$^{10}$-trifluoroacetylpteroyl)-γ-t-butyl-L-glutamyl-APADO3A-tris-t-butyl ester (9)

To a stirred, 0° C. slurry of N$^{10}$-trifluoroacetylpteroic acid (4) (0.204 g, 0.5 mmol) in DMF was added DCC (0.125 g, 0.6 mmol) and the slurry was stirred at 0° C. for 1 h. To this suspension was added L-glutamyl-γ-t-butyl-APADO3A-tri-t-butyl ester 8a (0.45 g, 0.53 mmol) followed by diisopropylethylamine (0.13 g, 1 mmol). The reaction mixture was allowed to stir for 2 h at 0° C. and then 12 h at RT. DMF was removed under reduced pressure and the residue was treated with water. The light yellow solid formed was filtered and dried under vacuum. Trituration of the solid with hot ethyl acetate (3×50 ml) and removal of the solvent yielded a light

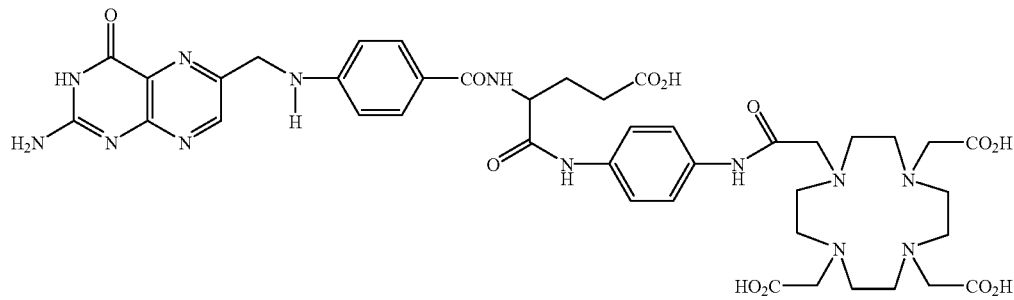

A) N-CBZ-γ-t-butyl-L-glutamyl-APADO3A-tri-t-butyl ester (9)

To an ice-cooled, stirred solution of N-CBZ-L-glutamic acid γ-t-butyl ester (7) (1.2 g; (3.7 mmol) and HATU (1.75 g, 4.6 mmol) in DMF (15 nmL) was added diisopropyl ethylarnine (1.48 g , 11.4 mmol) under nitrogen. The mixture was stirred at 0° C. for 15 min. APADO3A-tris-t-butylester (2) (2.0 g; 3.0 mmol) was added and the reaction mixture was stirred at RT for 12 h. DMF was removed under vacuum and the residue was treated with water and extracted with ethyl acetate (2×150 mL). The ethyl acetate layer was washed with NaOH (10%), water and dried (Na$_2$SO$_4$). The solvent was removed on a rotary evaporator and the residue was purified by column chromatography on silica gel with 5% methanol in CH$_2$Cl$_2$ as the eluant. UV visible fractions were collected and methylene chloride and methanol were removed to give a viscous oil which was dried under vacuum to give a foamy solid. Yield: 2.42 g (82%). MS: (M+H)$^+$= 982.7.

B) L-glutamyl-γ-t-butyl-APADO3A-tri-t-butyl ester (8a)

N-CBZ-γ-t-Butyl-L-glutamyl-APADO3A-tris-t-butylester (8) (2.0 g; 2.0 mmol) was hydrogenated (50 psi) in methanol (50.0 mL) over 30% Pd-C (200 mg) at RT for yellow solid. The product was purified by silica gel column chromatography, eluting with CH$_2$Cl$_2$:CH$_3$OH (95:5), to afford 0.185 g (30%) of the amide as a white solid. MS: (M+H)$^+$=1238.5. HRMS (FAB) m/z, Calcd for C$_{59}$H$_{82}$N$_{13}$O$_{13}$F$_3$ (M+Na$^+$) 1260.6005; Found: 1260.6033.

(D) N-Pteroyl-γ-t-butyl-L-glutamyl-APADO3A-tris-t-butyl ester (9a)

To a solution of APADO3A folate (9) (0.16 g; 125 mmol) in DMF-water (4.5:0.5 mL), piperidine (0.2 mL) was added and the solution was stirred at RT for 24 h. DMF-water were removed under vacuum and the residue was treated with water (5 mL). The precipitated yellow solid was filtered, dried under vacuum and purified by silica gel column chromatography (CH$_2$Cl$_2$:CH$_3$OH, 95:5). UV visible fractions were collected and methylene chloride and methanol were removed to give a solid. Yield: 95 mg (72.0%). The compound was further purified by reverse phase HPLC (Vydac-C18, 10μ, 10×25 cm) with a linear gradient of 0.1% TFA in H$_2$O/CH$_3$CN (0–60%) over sixty min to give 55 mg of yellow solid. MS: (M+H)$^+$=1143. HRMS (FAB) m/z, Calcd for C$_{57}$H$_{83}$N$_{13}$O$_{12}$ (MH$^+$) 1142.6362; Found: 1142.6426.

E) N-Pteroyl-γ-L-glutamyl-APADO3A (10).

N-Pteroyl-α-t-butyl-L-glutamyl-APADO3A-tris-t-butyl ester (9a) (0.1 g, 0.087 mmol), was treated with concentrated hydrochloric acid (0.2 mL) and the mixture was stirred for 15 min. Absolute ethanol (3.0 mL) was added to the reaction mixture and the precipitated solid was centrifuged and the supernatant solution was decanted. The solid was triturated with ethanol (3.0 mL), centrifuged and decanted. The solid was treated in the same manner with two additional volumes of ethanol (3.0 mL) and the hydrochloride obtained was dried under vacuum. Yield 82 mg. MS: $(M+H)^+=918$.

EXAMPLE 5

Gd-DO3A-APA-(α)-folate filtered into a centrifuge tube, an equal volume of acetone (15 mL) was added, and the mixture was chilled to −20° C. The resulting orange precipitate was isolated by centrifugation at 4° C., rinsed with ice-cold ethanol, re-dissolved in a minimal volume of water and freeze-dried to yield 113.8 mg of pale yellow Gd-DO3A-APA-((α)-folate product (77.2% yield), as determined by HPLC on a Supelcosil LC-18 column (25 cm×4.6 mm) eluted with a step gradient of 0 to 40% acetonitrile/buffer A. (buffer A=1.0 mM tris buffer pH 7.25 containing 0.2 mM EDTA). MS: $(M+H)^+=1072$; $(M+H+H_2O)^+=1090$. Anal. Calcd. for $C_{41}H_{47}N_{13}O_{12}NaGd$

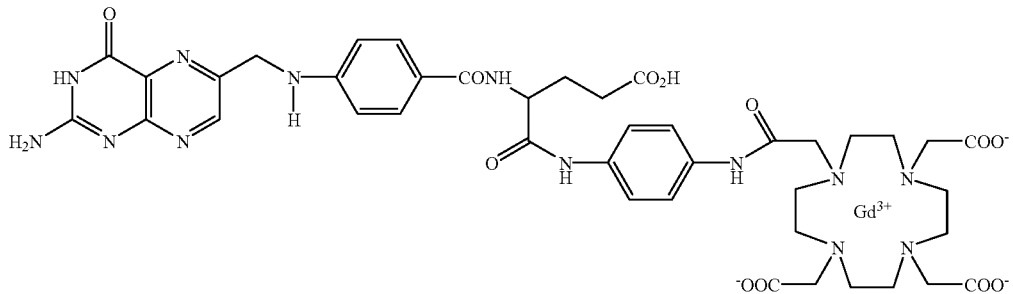

DO3A-APA-(α)-folate.4HCl.4H$_2$O (10) (137 mg, 0.1206 mmoles) was suspended in 4 mL of 0.05M NaOH with stirring under N$_2$. Solid GdCl$_3$.4H$_2$O (45.3 mg, 0.135 mmol) was added to the orange gel-like suspension and NaOH (0.05M) was gradually added dropwise to maintain a pH of ~4.5 to 5.0. After 24 hours, the yield of product was 81.4% as determined using HPLC (A$_{274}$). Water (5 mL) was added, and the pH of the solution was adjusted to 7.0 with 0.05M NaOH. The slightly hazy bright-yellow solution was 5.5 H$_2$O 0.5 NaCl: C, 40.28; H, 4.78; N, 14.90, Na, 2.82, H$_2$O, 8.11. Found: C, 40.41; H, 4.34; N, 14.57, Na, 2.71, H$_2$O, 8.07.

EXAMPLE 6

$^{153}$Gd-DO3A-APA-(α)-folate

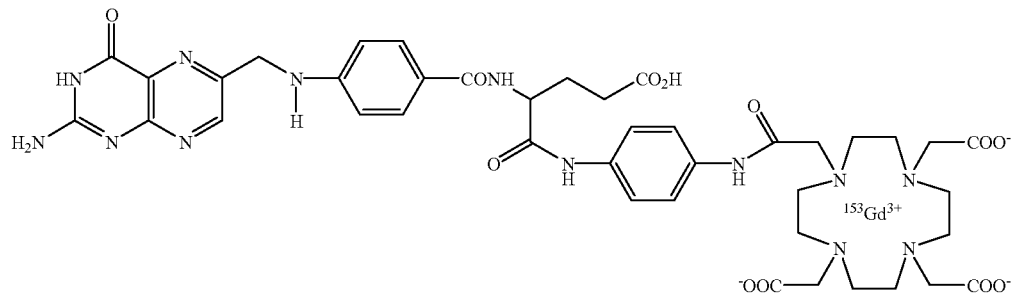

DO3A-APA-(α)-folate 4HCl.4H$_2$O (10) (8.33 mg, 0.00733 mmoles) was mixed with 5.0 mL of distilled water and adjusted to pH 6.8 with 0.1N NaOH. A 25.3 μL aliquot of this solution (35.7 nmol) was added to a 2-dram vial. To this was added 100 μCi of $^{153}$GdCl$_3$ in 0.5M HCl (35.7 nmol, 25.3 μL) and the solution was adjusted gradually to pH 5.2 using 0.1 N NaOH. After the reaction was stirred at room temperature for 3 days, $^{153}$Gd-DO3A-APA-(α)-folate had formed in 51% yield as determined by radioisotope detection using HPLC on a Supelcosil LC-18 column (25 cm×4.6 mm) eluted with a step gradient of 0 to 40% acetonitrile/buffer A. (buffer A=1.0 mM tris buffer pH 7.25 containing 0.2 mM EDTA).

EXAMPLE 7

N-Pteroyl-L-glutamyl-bis APADO3A (14) [Bis [DO3A-APA]-folate]

C) N-(N$^{10}$-trifluoroacetylpteroyl)-L-glutamyl-bisAPADO3A-tris-t-butyl ester (13)

To a cooled solution (0° C.) of N$^{10}$-trifluoroacetylpteroic acid (4) (0.13 g, 0.32 mmol) in dimethylformamide [DMF] (4.0 mL) was added hydroxybenzotriazole (0.052 mg, 0.34 mmol) and the mixture was stirred at 0° C. for 15 min. Cyclohexyl carbodiimide (0.08 g) was added to the reaction mixture and the mixture was stirred at 0° C. for 1 h. L-glutamyl-bis APA DO3A-tris-t-butyl ester (12a) was then added to the reaction mixture followed by diisopropylethylamine and stirred at RT for 18 h. The reaction mixture was concentrated under vacuum and the residue was treated with water. The solid obtained was filtered and dried under vacuum. The crude compound was triturated with ethyl acetate and decanted. The crude compound was chromatographed over silica gel using methylene chloride and methanol as the eluent. Fractions containing the compound were collected and evaporated to give 0.28 g of the coupled product. This was then treated with 0.25 g of decolorizing carbon in methanol. The carbon was filtered and methanol

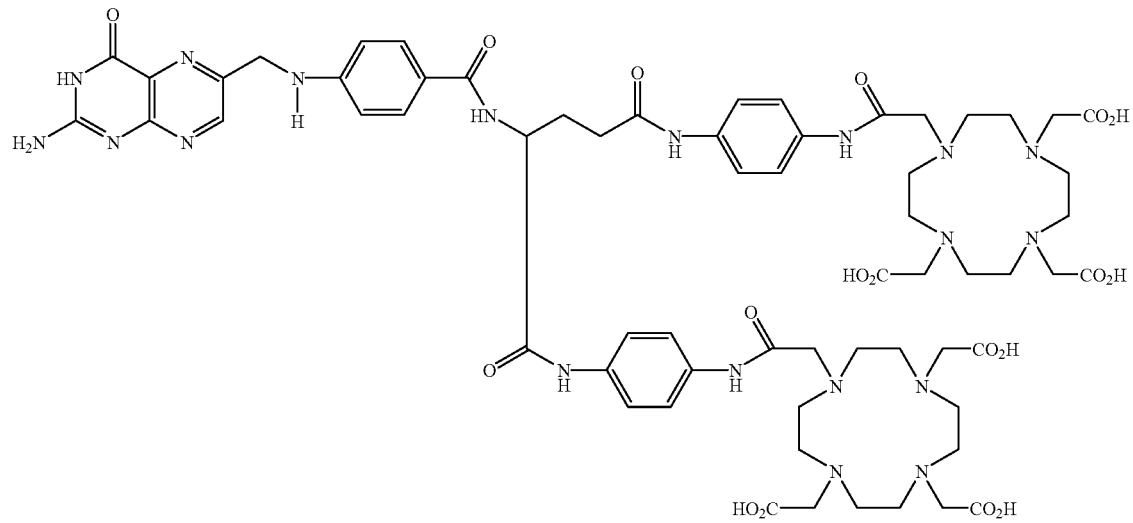

A) N-CBZ-L-glutamyl-bis APADO3A-tris-t-butyl ester (14)

To a cooled (0° C.) solution of N-CBZ-glutamic acid (11) (0.28 g, 1.0 mmol) in dimethyl formamide [DMF] (5.0 mL) were added HATU (1.0 g, 2.63 mmol) and diisopropyl ethylamine (0.52 g, 1.4 mL, 3.85 mmol) and the mixture was stirred at 0° C. for 15 min. APADO3A tris-t-butyl ester (2) (1.32 g, 2.0 mmol) was added to the reaction mixture and stirred at 0° C. for 1 h and at RT for 12 h. Potassium carbonate (1.0 g) was added to the reaction mixture, which was then stirred for 10 min. DMF was removed under vacuum and the residue was treated with water and dried. Crude yield: 1.52 g.

The crude coupled product was then purified by silica gel column chromatography (CH2Cl$_2$: CH$_3$OH, 95:5). Product-containing fractions were collected and the purity was determined by HPLC. Yield: 0.98 g (62%). MS: (M+Na)$^+$= 1593.

B) L-glutamyl-bis APADO3A-tris-t-butyl ester (12a)

CBZ-derivative (12) (0.5 g, 0.3 mmol) was dissolved in methanol (10 mL) and hydrogenated at 40 psi using 5% Pd-C (degussa type) for 12 h. The catalyst was removed by filtration and the methanol was removed on a rotary evaporator to give an oil. It was dried under vacuum to give a foamy solid. Yield: 0.45 g (98%). MS: (M+Na)$^+$=1459.

was removed to give 0.25 g of the pure product. MS: (M+2Na)$^+$1872.

D) N-Pteroyl-L-glutamyl-bisAPADO3A-tris-t-butyl ester (13a)

To a solution of the trifluoroacetyl derivative (13) (0.17 g; 0.099 mmol) in DMF:water (4.5: 0.5 mL) was added piperidine (0.3 mL) and the mixture was stirred at RT for 24 h. DMF was removed under vacuum and the residue was treated with water. The solid obtained was dissolved in methanol (5.0 mL) and treated with decolorizing carbon (100 mg). The carbon was removed by filtration and the methanolic solution was concentrated to give yellow solid. Yield: 140 mg. MS: (M +Na)$^+$=1753.

E) N-Pteroyl-L-glutamyl-bis-APADO3A (14)

N-Pteroyl-L-glutamyl-bisAPADO3A-tris-t-butyl ester (13a) (0.25 g, 0.145 mmol), was treated with concentrated hydrochloric acid (0.2 mL) and the mixture was stirred for 15 min. Absolute ethanol (3.0 mL) was added to the reaction mixture and the precipitated solid was centrifuged and the supernatant solution was decanted. The solid was triturated with ethanol (3.0 mL), centrifuged and decanted. The solid was treated in the same manner with two additional volumes of ethanol (3.0 mL) and the hydrochloride obtained was dried under vacuum. Yield 150 mg. MS: (M+H)$^+$=1395.

EXAMPLE 8

Bis (Gd-DO3A-APA)-folate

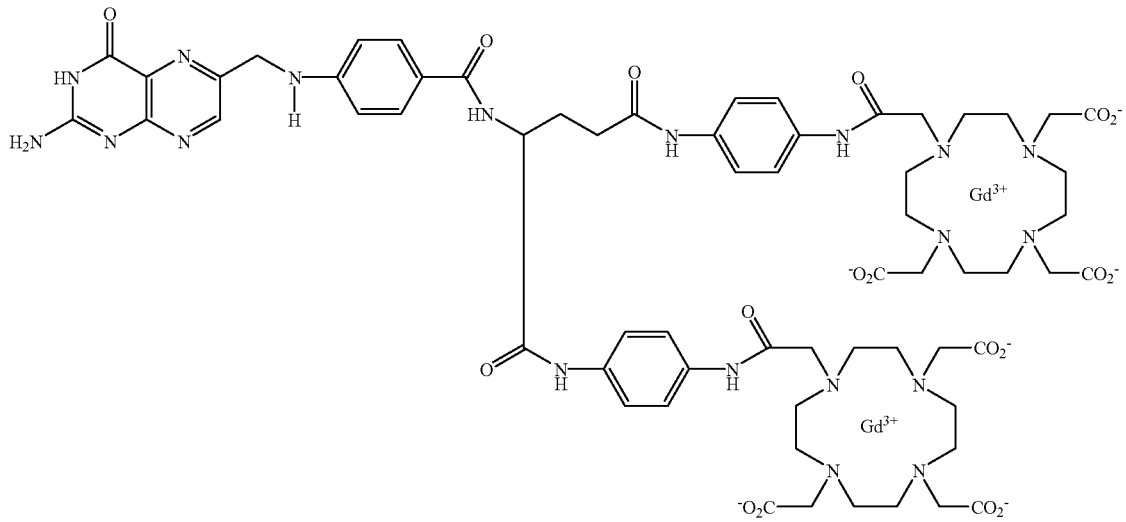

Bis(DO3A-APA)-folate.4HCl.10H$_2$O ligand (14) (75 mg, 0.0414 mmol) was dissolved in 1 mL of water and a solution of GdCl$_3$ in H$_2$O (0.095 mmol, 190 µL) was added with stirring. The pH of the reaction mixture was gradually raised to 6.8 with 1N NaOH, and the solution was allowed to stir overnight at RT in the dark. At 18 hours additional GdCl$_3$ in H$_2$O (0.003 mmol, 5.7 µL) was added. At 24 hours complex formation was determined to be 90% using HPLC (Supelcosil C-18-DB column, 0 to 40% acetonitrile/buffer A step gradient, buffer A=1.0 mM tris acetate buffer pH 7.25, containing 0.2 mM EDTA). Purification was accomplished using semi-preparative HPLC (Supelcosil C-18-DB column, 0 to 40% acetonitrile/water step gradient). The complex cuts were pooled and lyophilized and 36 mg of purified material obtained. After freeze drying, the HPLC purity was 97.3% at A$_{274}$. Overall yield: 50%. Analytical data, calculated for the hydrated HCl salt of Bis-(Gd-DO3A-APA-)folate.2HCl.14H$_2$O (Gd$_2$C$_{63}$O$_{18}$N$_{19}$H$_{76}$(2HCl.14H$_2$O) Mw=2027.7): Calculated C, 37.32%; H, 5.27%; N, 13.12%. Found C, 37.37%; H, 5.04%; N, 12.36%. MS (Electrospray): (M+H)$^+$, m/z=1701; (M+2H)$^{2+}$ Gd$_2$ cluster, m/z=852 [base peak].

EXAMPLE 9

Bis ($^{153}$Gd-DO3A-APA)-folate

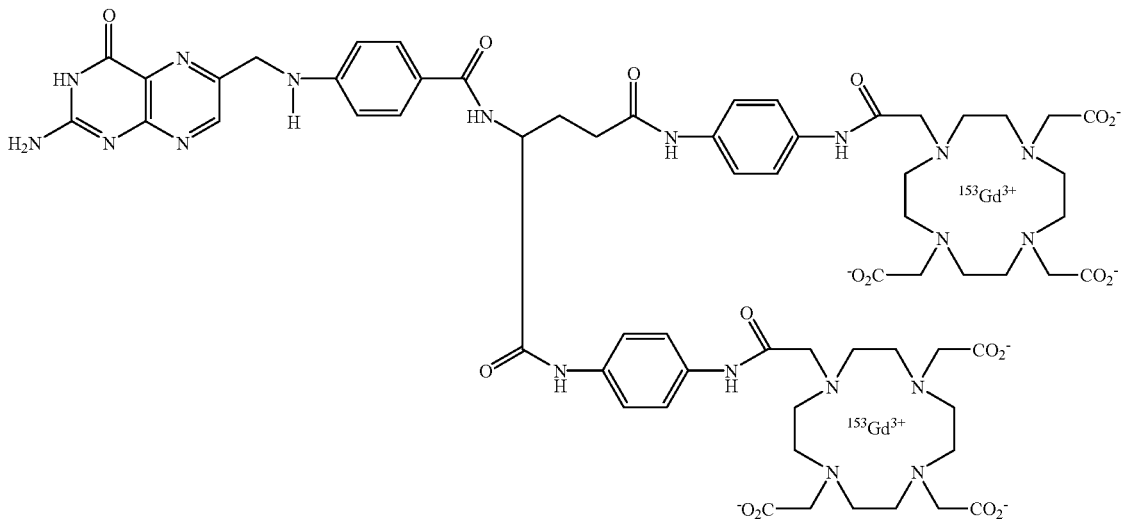

A ligand stock solution (1 mg/mL, 557 nmol/mL) was prepared by dissolving 10 mg of bis(DO3A-APA)-folate 4HCl.10H$_2$O ligand (14) in 10 mL of water. A carrier-added reaction mixture with a 1:1 metal to ligand ratio was prepared by premixing $^{153}$GdCl$_3$/0.5M HCl (23.2 µL, 100 µCi, 62.09 nmol Gd) with an aliquot of a 10 mM GdCl$_3$ stock solution (55.9 µL, 557 nmol), in a 1-dram bottle with stirring, followed by an aliquot of the bis(DO3A-APA)-folate ligand stock solution (557 µL, 310 nmol). The pH of the reaction mixture was gradually raised to 4.9 over two hours with dilute NaOH and it was then stirred in the dark overnight at RT. At 18 hours the pH was raised to 5.8. Complexation was monitored using HPLC (Supelcosil C18 column, acetonitrile/buffer A step gradient, buffer A=1.0 mM tris buffer pH 7.25 containing 0.2 mM EDTA). At 48 hours the pH was 5.8, and complex yield was 65%. The solution was reduced in volume to 250 µL using a nitrogen stream, the compound was purified using preparative HPLC (Supelcosil C18, acetonitrile/water step gradient), and the $^{153}$Gd/Gd-bis-complex-containing fractions were evaporated to dryness under a nitrogen stream. The material was reconstituted in 1.0 mL of water and the pH adjusted to 8.0 using 20 mM Tris HCl buffer. Overall yield: 41% as determined from recovered radioactivity. Radiochemical purity (RCP) was determined by HPLC as 96.4%.

EXAMPLE 10

Tris-t-butyl N-12-(3-amino-2-methoxycarbonyl-1-ethyl)-1,4,7,10-tetracyclododecane-1,4,7-tricarboxylate (17a)

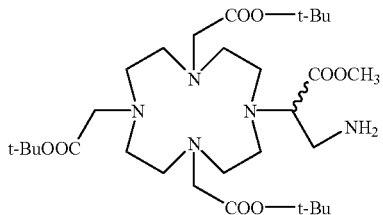

A) Methyl 3-amino-2-hydroxypropionate hydrochloride (19)

A suspension of isoserine (18) (20.0 g, 0.19 mol) in anhydrous methanol (100 mL) was saturated with HCl gas at 0° C. while being stirred with exclusion of moisture. The solid material slowly dissolved to yield a pale yellow liquid after a few minutes. The HCl saturated solution was stirred overnight (20 h) at room temperature. Excess HCl gas was removed by bubbling nitrogen into the reaction mixture and the solvent was removed under reduced pressure to yield the product as a syrup (27.1 g; yield 92%) Mass Spectrum M+H 120. The product was immediately taken to the next step without further purification.

B) Methyl 3-azido-2-hydroxypropionate
i) Preparation of triflylazide

To an ice-cold solution of sodium azide (166.0 g, 2.6 mol) in water (500 mL) dichloromethane (300 mL) was added, followed by trifluoromethanesulfonic anhydride (144.0 g, 0.51 mol) dropwise while maintaining the solution at 0–5° C. The reaction mixture was stirred at room temperature for 2 h. The organic layer was separated, washed first with water (2×100 mL) and then with saturated sodium carbonate (2×100 mL). The organic layer was dried (anhydrous sodium sulfate) and the solvent removed under reduced pressure at room temperature to obtain the product as a colorless oil (89.0 g; Yield: 100%).

ii) Methyl 3-azido-2-hydroxypropionate (16a)

To an ice-cold mixture of methyl 3-amino-2-hydroxypropionate hydrochloride (19) (27.1 g, 0.17 mol) in water (100 mL) and dichloromethane (100 mL) was added sodium carbonate (19.82 g, 0.187 mol) and CuSO$_4$. 5H$_2$O (0.3 g, 1.2 mmol) with stirring. Triflylazide from experiment 10(B)(i) (crude, 44.6 g, 0.25 mol) was added dropwise keeping the reaction temperature at 0–5° C. Methanol (about 100 mL) was added until the reaction mixture became homogeneous. The reaction mixture was allowed to come to room temperature and then stirred for 20 h. Water (500 mL) was added and the aqueous solution thoroughly extracted with dichloromethane (5×100 mL). The combined organic layers were washed with water (2×200 mL), saturated sodium carbonate (2×200 mL), and then dried (anhydrous sodium sulfate). After removal of the solvent, the residue was chromatographed over silica gel. Elution with 30% ethyl acetate in hexanes furnished the product as a colorless oil (14.0 g; Yield: 57%). R$_f$ 0.57 (30% ethyl acetate in hexanes).

C) Methyl 3-azido-2-trifluoromethanesulfonyloxypropionate (16b)

To a solution of methyl 3-azido-2-hydroxypropionate (16a) (14.0 g, 0.097 mol) in dry dichloromethane (50 mL) 2,6-lutidine (20.8 g, 0.194 mol) was added, followed by triflic anhydride (41.0 g, 0.146 mol) dropwise at 0° C. with stirring under nitrogen over a period of 1 h. The reaction mixture was allowed to come to room temperature and stirred for 16 h. The reaction mixture was diluted with 50 mL of dichloromethane and washed first with 2N HCl (2×50 mL) and then with water (2×100 mL). The organic layer was dried. The solvent was removed under reduced pressure at room temperature and the residue chromatographed over silica gel. Elution with hexane/ethyl acetate (9:1) yielded the product as a colorless oil (20.0 g; yield: 74%). R$_f$ 0.7 (30% ethyl acetate/hexane).

D) Tris-t-butyl N12-(3-azido-2-methoxycarbonyl-1-ethyl)-1,4,7,10-tetraazacyclododecane-1,4,7-tricarboxylate DO3A-tri-t-butyl ester hydrochloride (15a) (1.0 g, 1.81 mmol) was treated with 1N NaOH (20 mL) and extracted with ether (4×25 mL). The combined ether extracts were dried (anhydrous Na$_2$SO$_4$), concentrated under reduced pressure, and dried. DO3A-tris-t-butyl ester (0.8 g, 1.6 mmol), thus obtained, was dissolved in dry acetonitrile (5 mL) and anhydrous potassium carbonate (0.28 g, 2 mmol) was added. The mixture was cooled to 0° C. in an ice-bath. Methyl 3-azido-2-trifluoromethanesulfonyloxypropionate (16b) (0.47 g, 1.7 mmol), prepared in experiment 3, was added dropwise with stirring under nitrogen. After the addition, the reaction mixture was allowed to come to room temperature and stirred for 16 h. Acetonitrile was removed under reduced pressure and the resulting residue suspended in 20 mL of water and extracted with dichloromethane (3×20 mL). The combined organic layers were washed with water (4×25 mL) and dried (anhydrous sodium sulfate). The solvent was removed under reduced pressure and the resulting dark red paste was chromatographed over silica gel. Elution with 0.5% MeOH in chloroform yielded the product as a pale yellow paste (0.3 g, yield: 29%) Mass Spectrum M+H 642. R$_f$ 0.4 (9:1 chloroform/MeOH).

E) Tris-t-butyl N12-(3-amino-2-methoxycarbonyl-1-ethyl)-1,4,7,10-tetraazacyclododecane-1,4,7-tricarboxylate (17a)

To a solution of tris-t-butyl N12-(3-azido-2-methoxycarbonyl-1-ethyl)-1,4,7,10-tetracyclododecane-1,4,7-tricarboxylate from experiment 10D, (0.6 g, 0.94 mmol) in a 1:1 mixture of t-butanol and methanol (10 mL), palladium on carbon (10%, 0.12 g) was added and the mixture hydrogenated at 50 p. s. i. until the starting material disappeared as per TLC (4 h). The catalyst was filtered off through a pad of Celite and the filtrate freed of the solvent. The residue was dried in vacuo to obtain the product as a colorless paste (0.56 g; yield: 98%). R$_f$ 0.12 (9:1 chloroform/MeOH).

EXAMPLE 11

N-[1,5-Bis(benzyloxycarbonyl)-3-[2-(benzyloxycarbony)ethyl)]-3-pentyl]-N'-[1,7-bis-(t-butoxycarbony)amino-[4-(3-(t-butyloxycarbonyl)propyl]-4-heptyl]butanedioic diamide (39)

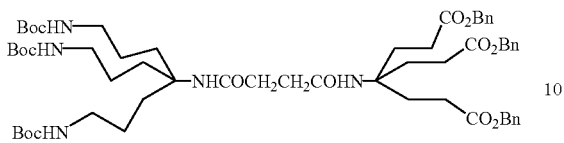

A) 1,5-Bis(benzyloxycarbonyl)-3-[2-(benzyloxycarbony)ethyl]-3-nitro pentane (40)

To a mixture of [3-(2-carboxyethyl)]-3-nitropentane-1,5-dicarboxylic acid (2.8 g, 0.01 mole) (prepared as described by James K. Young et al., *Macromolecules*, 1994, 27, 3464–34-71) and cesium carbonate (3.25 g, 0.025 mol) in acetonitrile (20.0 mL) was added benzylbromide (8.55 g, 6.0 mL, 0.05 mole) and the mixture stirred at RT for 24 h. Inorganic salts were filtered and the salts washed with acetonitrile. The filtrate and the washings were combined and evaporated to obtain an oil. Purification by chromatography over silica gel (hexane: ethyl acetate, 7:3) afforded the benzyl ester (40) as colorless viscous oil (4.5 g, yield: 82%). Mass Spectrum (M+H)hu += 548.

B) 3-Amino-[1,5-bis(benzyloxycarbonyl)-3-[2-(benzyloxycarbony)ethyl)]-pentane (41)

1,5-Bis(benzyloxycarbonyl)-3-[2-(benzyloxycarbony)ethyl]-3-nitro pentane (40) (2.9 g, 0.005 mole) was added to aluminum amalgam (prepared from 1.0 g of aluminum), in a mixture of THF and water (10:2, 10 mL). The mixture was stirred at room temperature for 6 h. The solvents were removed under vacuum and the residue purified by chromatography over silica gel (hexane: ethyl acetate) to obtain the amine product (41) (2.0 g; yield: 77%). Mass Spectrum (M+H)$^+$=518. This product was used in the next step without further purification.

C) N-[1,5-Bis(benzyloxycarbonyl)-3-[2-(benzyloxycarbony)ethyl)]-3-pentyl]-butanedioic monoamide (42)

To a solution of 3-Amino-[1,5-bis(benzyloxycarbonyl)-3-[2-(benzyloxycarbony)ethyl)]-pentane (41) (2.7 g, 0.0049 mole) in pyridine (10.0 mL) was added succinic anhydride (0.5 g, 0.005 mol) and the mixture was stirred at RT for 24 h. Pyridine was removed under vacuum. To the residue water was added and the solution made acidic with 0.1 N citric acid. The solid formed was filtered and air-dried to obtain the monoamide product (2.8 g; yield: 85%). Mass Spectrum (M+H)$^+$=618. mp. 100–102° C. This product was used in the next step without further purification.

D) N-[1,5-Bis(benzyloxycarbonyl)-3-[2-(benzyloxycarbony)ethyl)]-3-pentyl]-N'-[1,7-bis-(t-butoxycarbony)amino-[4-(3-(t-butyloxycarbonyl)propyl]-4-heptyl]butanedioic diamide (39)

To a solution of N-[1,5-Bis(benzyloxycarbonyl)-3-[2-(benzyloxycarbony)ethyl)]-3-pentylamino-butanedioic monoamide (42) (0.62 g, 0.01 mol) in dimethylformamide (7 mL) was added carbonyldiimidazole (0.165 g, 0.01 mol) and the mixture was stirred at room temperature for 15 min. 1,7-Bis[N-t-butoxycarbonyl)amino]4-[3-(N-t-butoxycarbonyl)-amino)propyl]-4-aminoheptane (0.5 g, 0.001 mol) (prepared as previously described by James K. Young et al., *Macromolecules*, 1994, 27, 3464–3471) was the added to the reaction mixture and stirred at room temperature overnight. Dimethylformamide was removed in vacuo and the residue treated with water. The solid that resulted was filtered and air dried. Crystallization from hexane:ethyl acetate furnished the pure diamide product (39) (0.52 g; yield: 47%). Mass Spectrum (M+H)$^+$=1103. mp 95–96° C.

EXAMPLE 12

12-Amino-3,3,9,9-tetramethyl-5-oxa-4,8-diaza-2,10-dodecanedione dioxime (52b)

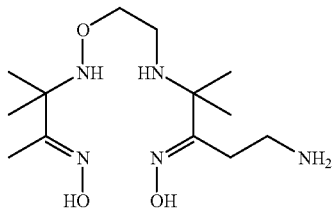

A) 4-Methyl-1-(phthalimido)-3-pentene (53b)

To a suspension of phthalimide, potassium derivative (11.5 g, 0.062 mol) in dry dimethylformamide (60 mL) was added 1-bromo-4-methyl-3-pentene (10.0 g, 0.061 mol) and the suspension was stirred under $N_2$ at 90° C. for 4 h. The reaction mixture was poured into water (300 mL) and the precipitated solid was filtered and washed with water and the solid was dried under vacuum. Yield: 12.8 g (91%). mp 95–97° C. MS: (M+H)$^+$=229.9.

B) 4-Chloro-4-methyl-1-(phthalimido)-3-nitrosopentane (51)

To a cooled (0–5° C.) solution of 4-methyl-1-(phthalimido)-3-pentene (5.0 g, 0.022 mol) and isoamyl nitrite (13.0 g, 15 mL, 0.11 mol) was added concentrated hydrochloric acid (4.0 mL, 0.04 mol) with stirring. The reaction mixture was maintained below 5° C. during the addition and stirred at 5° C. for an additional 2 h. The solid formed was filtered and washed with cold ether:ethanol (3:1, 150 mL) and dried. Yield: 4.72 g (72.8%). It was crystallized from acetonitrile. mp 140–141° C. MS: (M+H)$^+$=296.0.

C) 12-Phthalimido-3,3,9,9-tetramethyl-5-oxa-4,8-diaza-2,10-dodecanedione dioxime (52a)

To a slurry of 3-[[2-(aminoxy)ethyl]amino]-3-methyl-2-butananone oxime hydrochloride (50) (2.15 g, 10 mmol) and 4-chloro-4-methyl-1-(phthalimido)-3-nitroso-pentane (51) (2.95 g, 10.0 mmol) in acetonitrile (100 mL) was added diisopropylethylamine (3.88 g, 5.2 mL, 29.8 mmol) and the reaction mixture was stirred at room temperature for 24 h. The clear light blue solution obtained after completion of the reaction was concentrated and the residue was treated with water. The thick oil obtained was extracted with ether (200 mL), and the ether layer was washed with a saturated solution of sodium bicarbonate, water and dried ($Na_2SO_4$). Evaporation of ether gave a foamy solid, which was purified by column chromatography using methylene chloride and methanol (95:5, 90:10). The fractions containing the product were collected and evaporated to give a white solid. Yield: 3.1 g (71.5%). mp 74–75° C. MS: (M+H)$^+$=434.3.

D) 12-Amino-3,3,9,9-tetramethyl-5-oxa-4,8-diaza-2,10-dodecanedione dioxime (52b)

To a solution of 12-phthalimido-3,3,9,9-tetramethyl-5-oxa-4,8-diaza-2,10-dodecane dione dioxime (52a) (2.0 g, 4.6 mmol) in methylene chloride (100 mL) was added hydrazine (0.3 mL, 9.3 mmol) and the reaction mixture was refluxed for 3 h. The white solid formed was filtered and the filter cake was washed with methylene chloride (50 mL). The combined filtrate and the washings were concentrated to give a thick oil which was dried under vacuum to afford a white solid. Yield: 1.2 g (82%). MS: (M+H)$^+$=304.1. This was used in the next step without further purification.

EXAMPLE 13

12-N-(N-Pteroyl-α-L-glutamyl)-3,3,9,9-tetramethyl-5-oxa-4,8-diaza-2,10-dodecanedione dioxime ligand (62)

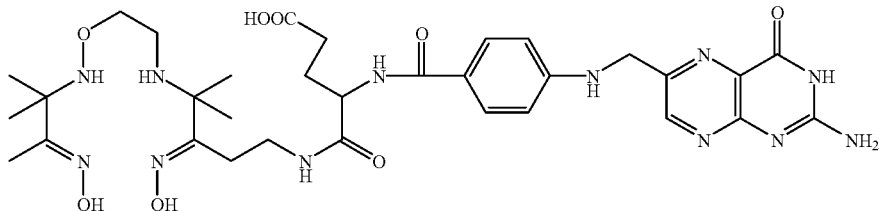

A) 12-N-FMOC-γ-t-Butyl-L-glutamyl-3,3,9,9-tetramethyl-5-oxa-4,8-diaza-2,10-dodecanedione dioxime (58)

To an ice-cooled, stirred solution of commercially available (Bachem) N-FMOC-L-glutamic acid γ-t-butyl ester (57) (0.73 g, 1.65 mmol) in dimethylformamide (2.5 mL) was added hydoxybenzotriazole (0.265 g, 1.73 mmol) and the solution was stirred for 10 min. Dicyclohexylcarbodiimide (0.357 g, 1.73 mmol) was added and the mixture was stirred at 0° C. for 30 min. 12-Amino-3,3,9,9-tetramethyl-5-oxa-4,8-diaza-2,10-dodecanedione dioxime (52b) (0.5 g, 1.65 mmol) was added followed by diisopropylethylamine (0.23 g, 0.3 mL, 1.73 mmol) and the reaction mixture was stirred at room temperature for 6 h. The precipitated dicyclohexylurea was filtered and the DMF was removed under vacuum. The residue was purified by column chromatography on silica gel with CH$_2$Cl$_2$: CH$_3$OH (95:5, 90:10) as the eluant. UV-visible fractions were collected and solvents were removed to give a viscous oil which was dried under vacuum to give a foamy solid. Yield: 0.45 g (38%). MS: (M+H)$^+$=711.5.

B) 12-N-L-Glutamyl-γ-t-butyl-3,3,9,9-tetramethyl-5-oxa-4,8-diaza-2,10-dodecanedione dioxime (59)

To a solution of 12-N-FMOC-γ-t-butyl-L-glutamyl-3,3,9,9-tetramethyl-5-oxa-4,8-diaza-2,10-dodecanedione dioxime (58) (0.45 g, 0.63 mmol) in acetonitrile (2 mL) was added piperidine (0.5 mL) and the mixture was stirred at room temperature for 12 h. Acetonitrile was removed on a rotary evaporator and the residue was purified by silica gel column chromatography using CH$_2$Cl$_2$: CH$_3$OH (95:5, 90:10, 80:20). Fractions containing the product were collected and the solvent was removed to give a thick oil. It was dried under vacuum to give 12-N-L-glutamyl-γ-t-butyl-3,3,9,9-tetramethyl-5-oxa-4,8-diaza-2,10-dodecanedion dioxime as a foamy solid. Yield: 0.18 g (58%). MS: (M+H)$^+$=489.5.

C) 12-N-(N$^{10}$-trifluoroacetylpteroyl)-γ-t-butyl-L-glutamyl)-3,3,9,9-tetramethyl-5-oxa-4,8-diaza-2,10-dodecanedione dioxime (60)

To a stirred, 0° C. slurry of N$^{10}$-trifluoroacetylpteroic acid (4) (0.125 g, 0.3 mmol) in DMF (2.5 mL) was added hydroxybenzotriazole (0.050 g, 0.33 mmol). After 10 min, DCC (0.070 g, 0.34 mmol) was added and the slurry was stirred at 0° C. for 15 min. To this suspension was added 12-N-L-glutamyl-γ-t-butyl-L-3,3,9,9-tetramethyl-5-oxa-4,8-diaza-2,10-dodecanedione dioxime (59) (0.15 g, 0.3 mmol), followed by diisopropylethylamine (0.13 mL, 0.77 mmol). The reaction mixture was allowed to stir for 2 h at 0° C. and then 12 h at RT. DMF was removed under reduced pressure and the residue was treated with water. The light yellow solid formed was filtered and dried under vacuum. The coupled product was purified by reverse phase HPLC (Vydac-C18, 10 μ, 10×25 cm) with a linear gradient of 0.1% TFA in H$_2$O/CH$_3$CN (0–10% over 10 min and 10–40% over 120 min. The fractions containing the product were pooled and freeze-dried to give a light yellow solid. Yield: 0.13 g (37%). MS: (M+H)$^+$=879.5. HRMS (FAB) m/z, Calcd for C$_{38}$H$_{54}$N$_{12}$O$_9$F$_3$: (M+H)$^+$:879.4089. Found: 879.4076.

D) 12-N-(N-Pteroyl-γ-t-butyl-L-glutamyl)-3,3,9,9-tetramethyl-5-oxa-4,8-diaza-2,10-dodecane dione dioxime (61)

To a solution of 12N-(N$^{10}$-trifluoroacetylpteroyl)-γ-t-butyl-L-glutamyl)-3,3,9,9-tetramethyl-5-oxa-4,8-diaza-2,10-dodecanedione dioxime (60) (0.31 g, 0.35 mmol) in DMF-Water (4.5:0.5, 5 mL), was added piperidine (0.3 mL) and the solution was stirred at RT for 24 h. Dimethylformamide-water were removed under vacuum to give a thick oil, which was treated with water (5 mL). The resulting precipitated yellow solid was filtered and dried under vacuum. This compound was purified by reverse phase HPLC (Vydac-C18, 10μ, 10×25 cm) with a linear gradient of 0.1% TFA in H$_2$O/CH$_3$CN (0–10% over 10 min and 10–40% over 120 min. The fractions containing the product were pooled and freeze dried to give a light yellow solid. Yield: 0.15 g (53%). MS: (M+H)$^+$=783.5. HRMS (FAB) m/z, Calcd for C$_{36}$H$_{54}$N$_{12}$O$_8$ (M+H)$^+$:783.4266; Found: 783.4238.

E) 12-N-(N-Pteroyl-α-L-glutamyl)-3,3,9,9-tetramethyl-5-oxa-4,8-diaza-2,10-dodecanedione dioxime(62)

12-(N-Pteroyl-γ-t-butyl-L-glutamyl)-3,3,9,9-tetramethyl-5-oxa-4,8-diaza-2,10-dodecane dione dioxime (61) (0.16 g, 0.2 mmol), was dissolved in trifluoroacetic acid (0.3 mL) and stirred for 30 min. Trifluoroacetic acid was removed under vacuum and the product obtained was purified by reverse phase column chromatography. (Vydac-C18, 10μ, 10×25 cm) with a linear gradient of 0.1% TFA in H$_2$O/CH$_3$CN (0–10% over 10 min. and 10–40% over 120 min). The fractions containing the product were pooled and freeze dried to give a light yellow solid. Yield: 0.095 g (48%). MS: (M+H)$^+$=727.5. HRMS (FAB) m/z, Calcd for C$_{32}$H$_{46}$N$_{12}$O$_8$ (M+H)$^+$:727.3640; Found: 727.3640.

EXAMPLE 14

99m-Technetium complex of 12-(N-Pteroyl-α-L-glutamyl)-3,3,9,9-tetramethyl-5-oxa-4,8-diaza-2,10-dodecanedione dioxime

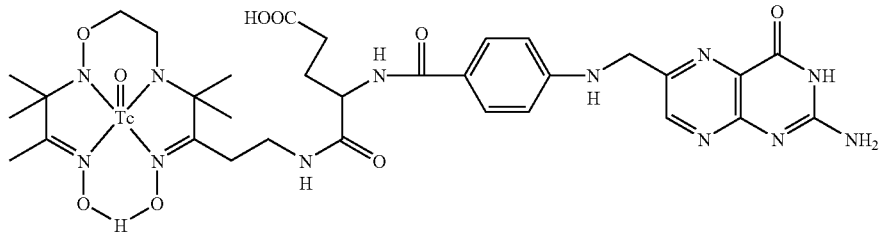

12-(N-Pteroyl-α-L-glutamyl)-3,3,9,9-tetramethyl-5-oxa-4,8-diaza-2,10-dodecanedione dioxime (2–4 mg) was dissolved in 0.1N NaHCO$_3$ (0.5 mL) and $^{99m}$TcO$_4^-$ (0.25 mL, 5–15 mCi) was added, followed by 50 μL of a saturated solution of stannous tartrate in nitrogen-purged normal saline. After 10 minutes, the desired technetium complex was isolated from impurities and excess ligand by preparative HPLC in ~45% yield using a YMC basic column that was conditioned and eluted with a gradient of MeOH/0.1N tris chloride buffer, pH 7.5 at a flow rate of 1.0 mL/min.

EXAMPLE 15

12-(N-Pteroyl-γ-L-glutamyl)-3,3,9,9-tetramethyl-5-oxa-4,8-diaza-2,10-dodecanedione dioxime. (Oxa PnAO Folic acid (γ-isomer)) (68)

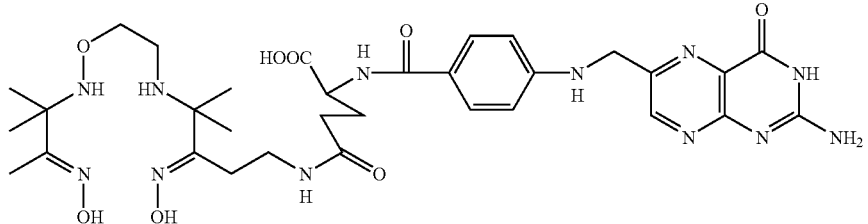

A) 12-N-FMOC-α-t-butyl-L-glutamyl-3,3,9,9-tetramethyl-5-oxa-4,8-diazacanedione dioxime. (64)

To an ice cooled stirred solution of N-FMOC-L-glutamic acid-α-t-butyl ester (63) (0.74 g, 1.74 mmol) and HATU (0.86 g, 2.26 mmol) in methylene chloride (15 mL) was added diisopropylethylamine (0.52 g, 0.75 mL, 4.0 mmol). The reaction mixture was stirred under nitrogen at 0° C. for 15 min. 12-Amino-3,3,9,9-tetramethyl-5-oxa-4,8-diaza-2,10-dodeanedione dioxime (52b) (0.5 g, 1.65 mmol) was added and the reaction mixture was stirred at room temperature for 6 h. Methylene chloride was removed and the residue was treated with water and extracted with methylene chloride (2×50 mL). The methylene chloride solution was washed with sodium bicarbonate solution (2×50 mL), washed with water and dried (Na$_2$SO$_4$). The solvent was removed and the residue was purified by chromatography (silica gel, CH$_2$Cl$_2$:CH$_3$OH, 95:5). Fractions containing the product were collected and the solvents were removed to give a viscous oil, which was dried under vacuum to give a foamy solid. Yield: 0.68 g (58%). MS: (M+H)$^+$=711.5. HRMS (FAB) m/z, Calcd for C$_{37}$H$_{54}$N$_6$O$_8$: (M+H)$^+$: 711.4081. Found: 711.4109.

B) 12-N-L-glutamyl-α-t-Butyl-3,3,9,9-tetramethyl-5-oxa-4,8-diaza-2,10-dodecanedione dioxime (65)

To a solution of 12-N-FMOC-α-t-butyl-L-glutamyl-3,3,9,9-tetramethyl-5-oxa-4,8-diaza-2,10-dodecanedione dioxime (64) (0.68 g, 0.96 mmol) in acetonitrile (5 mL) was added piperidine (0.5 mL) and the mixture was stirred at RT for 12 h. Acetonitrile was removed on a rotary evaporator and the residue was purified by silica gel column chromatography using CH$_2$Cl$_2$: CH$_3$OH (95:5, 90:10, 85:15). Fractions containing the compound were collected and the solvent was removed to give thick oil. It was dried under vacuum to give 12-N-L-glutamyl-a-t-butyl-3,3,9,9-tetramethyl-5-oxa-4,8-diaza-2,10-dodecanedione dioxime as a foamy solid. Yield: 0.37 g (79%). MS: (M+H)$^+$=489.5. HRMS (FAB) m/z, Calcd for C$_{22}$H$_{44}$N$_6$O$_6$ (M+H)$^+$: 489.3401. Found: 489.3376.

C) 12N-(N$^{10}$-trifluoroacetylpteroyl)-α-t-butyl-L-glutamyl)-3,3,9,9-tetramethyl-5-oxa-4,8-diaza-2,10-dodecanedione dioxime(66)

To a stirred, 0° C. slurry of N$^{10}$-trifluoroacetylpteroic acid (4) (0.125 g, 0.3 mmol) in DMF (2.5 mL) was added hydroxybenzotriazole (0.050 g, 0.33 mmol). After 10 min, DCC (0.070 g, 0.34 mmol) was added and the slurry was stirred at 0° C. for 15 min. To this suspension was added 12-N-L-glutamyl-α-t-butyl-L-3,3,9,9-tetramethyl-5-oxa-4,8-diaza-2,10-dodecanedione dioxime (65) (0.15 g, 0.3 mmol) followed by diisopropylethylamine (130.0 mL, 0.77 mmol). The reaction mixture was allowed to stir for 2 h at 0° C. and then 12 h at room temperature. DMF was removed under reduced pressure and the residue was treated with water. The light yellow solid formed was filtered and dried under vacuum. The coupled product was purified by reverse phase HPLC (Vydac-C18, 10μ, 10×25 cm) with a linear gradient of 0.1% TFA in H$_2$O/CH$_3$CN (0–10% over 10 min and 10–40% over 120 min. The fractions containing the product were pooled and freeze-dried to give a light yellow solid. Yield: 0.16 g (59%). MS: (M+H)$^+$=879.5. HRMS (FAB) m/z, Calcd for C$_{38}$H$_{54}$N$_{12}$O$_9$F$_3$ (M+H)$^+$: 879.4089; Found: 879.4091.

D) 12-(N-Pteroyl-α-t-butyl-L-glutamyl)-3,3,9,9-tetramethyl-5-oxa-4,8-diaza-2,10-dodecane dione dioxime (67)

To a solution of 12N-(N[10]-trifluoroacetylpteroyl)-α-t-butyl-L-glutamyl)-3,3,9,9-tetramethyl-5-oxa-4,8-diaza-2,10-dodecanedione dioxime (66) (0.25 g, 0.28 mmol) in DMF-Water (4.5:0.5 mL, 3 mL) was added piperidine (0.25 mL) and the solution was stirred at room temperature for 24 h. Dimethylformamide-water was removed under vacuum to give a thick oil. The oil was treated with water (5 mL) and the precipitated yellow solid was filtered and dried under vacuum. Yield: 0.2 g (90%). An analytical sample was purified by reverse phase HPLC (Vydac-C18, 10μ, 10×25 cm) with a linear gradient of 0.1% TFA in $H_2O/CH_3CN$ (0–10% over 10 min and 10–40% over 120 min). The fractions containing the product were pooled and freeze-dried to give a light yellow solid. MS: $(M+H)^+=783.5$. HRMS (FAB) m/z, Calcd for $C_{36}H_{54}N_{12}O_8$ $(M+H)^+$: 783.4266; Found: 783.4240.

E) 12-(N-Pteroyl-γ-L-glutamyl)-3,3,9,9-tetramethyl-5-oxa-4,8-diaza-2,10-dodecanedione dioxime (68)

12-(N-Pteroyl-α-t-butyl-L-glutamyl)-3,3,9,9-tetramethyl-5-oxa-4,8-diaza-2,10-dodecanedione dioxime (67) (0.135 g) was dissolved in trifluoroacetic acid (0.3 mL) and stirred for 30 min. Trifluoroacetic acid was removed under vacuum and the product obtained was purified by reverse phase column chromatography. (Vydac-C18, 10μ, 10×25 cm) with a linear gradient of 0.1% TFA in $H_2O/CH_3CN$ (0–10% over 10 min and 10–30% over 90 min). The fractions containing the product were pooled and freeze-dried to give a light yellow solid. Yield: 0.065 g (48%). MS: $(M+H)^+=727.5$. HRMS (FAB) m/z, Calcd for $C_{32}H_{46}N_{12}O_8$ $(M+H)^+$: 727.3640; Found: 727.3659.

EXAMPLE 16

99m-Technetium Complex of 12-(N-Pteroyl-γ-L-glutamyl)-3,3,9,9-tetramethyl-5-oxa-4,8-diaza-2,10-dodecanedione dioxime 12-(N-Pteroyl-γ-L-glutamyl)-3,3,9,9-tetramethyl-5-oxa-4,8-diaza-2,10-dodecanedione dioxime (2–4 mg) was dissolved in 0.1N $NaHCO_3$ (0.5 mL) and $^{99m}TcO_4^-$ (0.25 mL, 5–15 mCi) was added, followed by 50 μL of a saturated solution of stannous tartrate in nitrogen-purged normal saline. After 10 minutes at room temperature, the desired technetium complex was purified from impurities and excess ligand by preparative HPLC using a YMC basic column that was conditioned and eluted with a gradient of MeOH/0.1N tris chloride buffer, pH 7.5 at a flow rate of 1.0 mL. The desired product was isolated in ~45% yield.

B. Biological Evaluation

EXAMPLE 17

Binding Studies with $^{153}$Gd-DO3A-APA-folate (α or γ isomer) in KB and JAR Cells in Vitro Cell culture: KB cells (a human nasopharyngeal epidermal carcinoma cell line) and JAR cells (a human choriocarcinoma cell line) were obtained from ATCC (American Type Culture Collection). Both cell lines are reported to overexpress transcripts encoding folate binding protein. KB cells were grown in folate-free Minimal Essential Medium with Earle's salts, 1-glutamine and non-essential amino acids obtained from Life Technologies, Inc. JAR cells were grown in RPMI formulated without folic acid, (catalog #27016, Life Technologies, Inc). The media for each cell line was supplemented with 10% defined fetal calf serum (HyClone, Inc.) Monolayers were cultured at 37° C. in a humidified atmosphere containing 5% $CO_2$.

Forty-eight hours prior to each experiment, $5 \times 10^5$ cells were seeded into 35 mm culture dishes and allowed to grow for 2 days in folate-depleted media. The cells were then washed with Tris-buffered saline (TBS=150 mM NaCl, 50 mM Tris, pH 7.5) and 1 mL of fresh media containing 10 pmol $^{153}$Gd-DO3A-APA-folate (α or γ isomer) and 0–900 pmol of cold native folate per sample was added. Control experiments were performed using 10 pmol of $^3$H folate (Amersham International) and 0–900 pmol of cold native folate. The cells were incubated for 30 min at 37° C. They were then washed three times with ice cold TBS and suspended in one ml of water. Cell associated radioactivity was determined by gamma ($^{153}$Gd-folate) or scintillation counting ($^3$H-folate) of a 500 μl aliquot of this suspension; 100 μl was used in the BCA protein assay (Pierce catalog #23225), which was used to determine and normalize for cellular protein content.

Data from these studies in KB cells are shown in FIG. 1. In KB cells, the data demonstrate that $^3$H folate and the

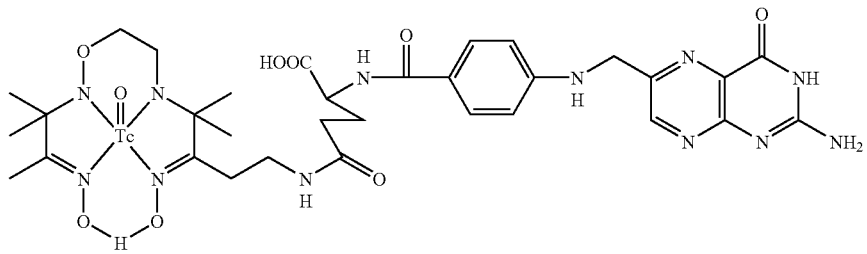

complexes of this invention were equally effective in their ability to compete with cold native folate for binding to KB cells that overexpress folate binding protein. No significant differences were seen in the amount of $^3$H-folate or $^{153}$Gd-DO3A-APA- (α)- or (γ)-folate isomers that were bound to the KB cells. These results indicate that covalent attachment of a metal chelate to either the alpha or gamma carboxylate of folic acid does not compromise the ability of the conjugate to bind to KB cells. The results obtained for the alpha isomer are surprising in light of Wang et al., who, as noted above, have taught that alpha conjugates show no ability to compete with native folate.

Figure 2:
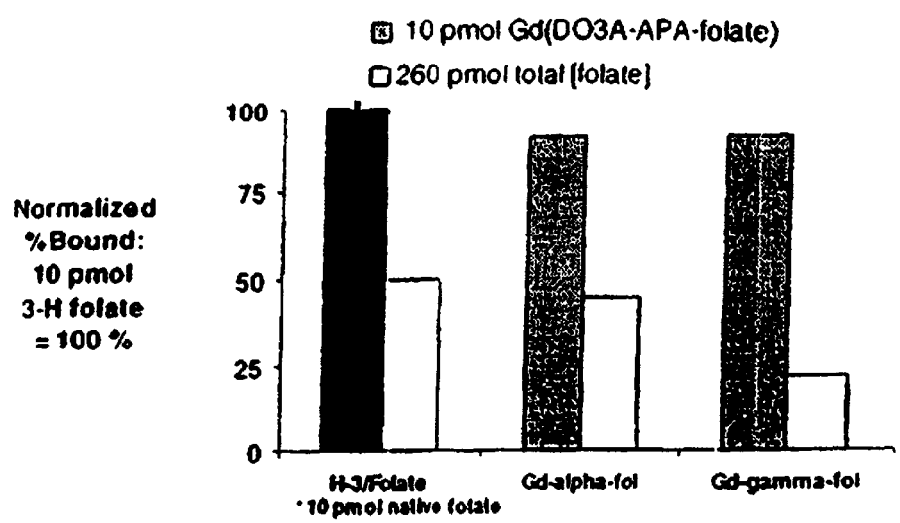
FIG. 2 shows binding of $^3$H-folate and of the alpha or gamma isomer of $^{153}$Gd-DO3A-APA-folate to KB cells at 4° C. in the presence and absence of excess folate.

In a second experiment, the ability of the alpha and gamma isomers of $^{153}$Gd-DO3A-APA-folate to bind to KB cells at 4° C. was studied. KB cells (~5×10$^5$ cells/well) were seeded into 35-mm wells and incubated for 48 hours as described above. The cells were then cooled to 4° C. for 30 min and incubated with the following mixtures for 30 min at 4° C.:

1. 10 pmol of $^3$H-folate
2. 10 pmol of $^3$H-folate and 250 pmol of native folate
3. 10 pmol of $^{153}$Gd/Gd(DO3A-APA-α-folate)
4. 10 pmol of $^{153}$Gd/Gd(DO3A-APA-α-folate) and 250 pmol of native folate
5. 10 pmol of $^{153}$Gd/Gd(DO3A-APA-γ-folate)
6. 10 pmol of $^{153}$Gd/Gd(DO3A-APA-γ-folate) and 250 pmol of native folate Following the incubation period, the cells were washed 3 times with ice-cold Tris-buffered saline. The cells were then stripped from the plates using 1.0 mL of water. Aliquots of the water/cell mixture were assayed for the respective radioisotopes and for cellular protein (to determine the number of KB cells present in each well). The radioassay data were used to calculate the % of radiolabeled compound bound to the cells in the absence and presence of unlabeled native folate. The results from this study are given in FIG. 2. Data in FIG. 2 are presented as the percentage bound, relative to the % bound in the control wells containing 10 pmol of $^3$H-folate.

These data indicate that when 10 pmol of $^{153}$Gd/Gd (DO3A-APA-folate) was incubated with KB cells for 30 min at 4° C., the α- and γ-isomers of $^{153}$Gd/Gd(DO3A-APA-folate) both bound to the KB cells to the same extent as that observed with 10 pmol of $^3$H-folate. (FIG. 2, dark bars).

These binding experiments were repeated in the presence of 250 pmol of cold native folate, to determine if the addition of excess cold folate would cause a decrease in the quantity of $^3$H or $^{153}$Gd bound to the KB cells at the end of the experiment. Such a result is expected if the radiolabeled compounds and native folate compete for binding to folate binding protein on the KB cells and an excess of cold folate is added. The results observed (FIG. 2, white bars) indicate that both native folate and the alpha and gamma isomers of $^{153}$Gd/Gd(DO3A-APA-folate) do compete for folate binding protein on the KB cells, and that the addition of 250 pmol of cold folate causes a similar effect on the degree of binding of 10 pmol $^3$H-folate as it does on the binding of 10 pmol of either the alpha or gamma isomer of $^{153}$Gd/Gd(DO3A-APA-folate).

Figure 3:
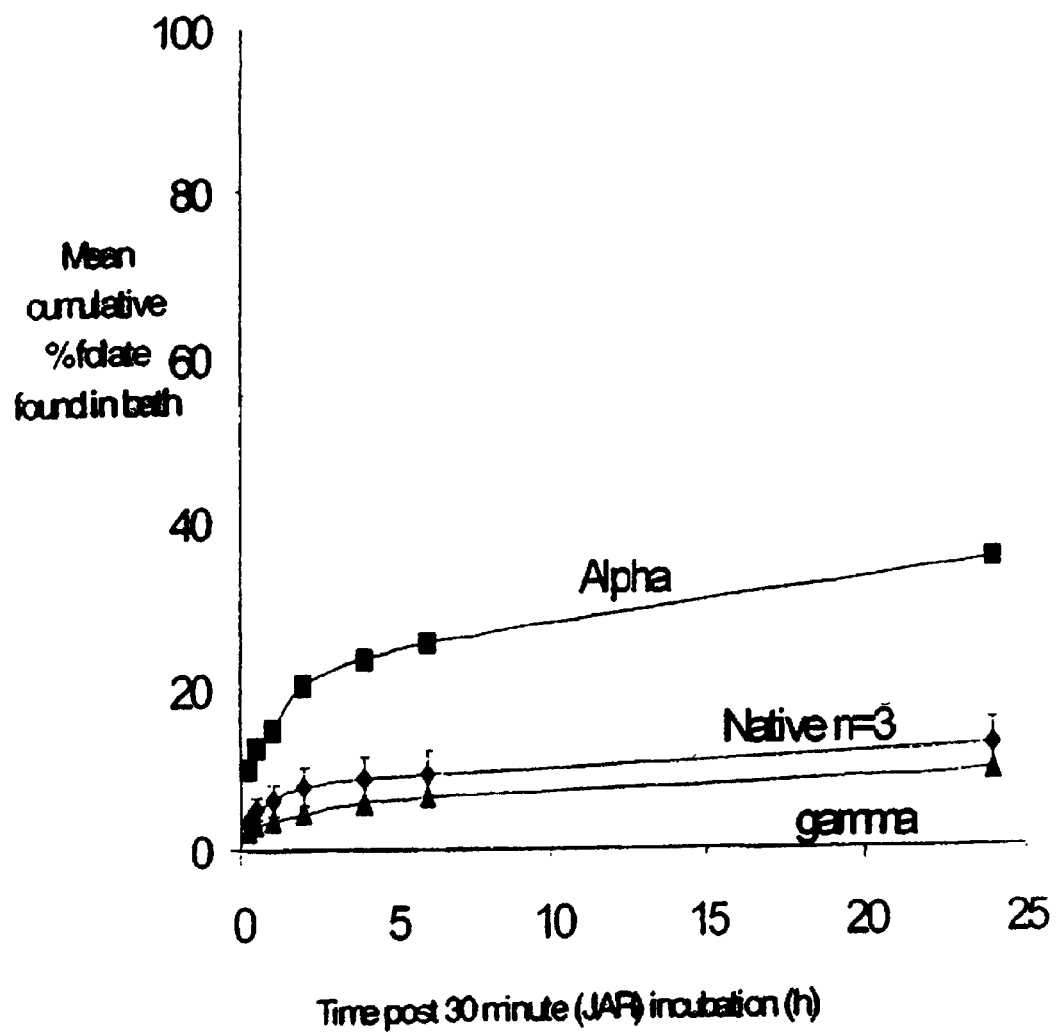
FIG. 3 shows washout of $^{153}$Gd(DO3A-APA)-($\alpha$- or $\gamma$-)folate or $^3$H-folate from JAR cells.

Data from studies in JAR cells are shown in FIG. 3.

In these cells, the (α)- or (γ)-isomers of $^{153}$Gd-DO3A-APA-folate were equally effective in their ability to compete with cold native folate for binding to the JAR cells. In contrast to the data from KB cells, binding of these Gd-folate compounds to JAR cells was about half as effective as that of the radiolabeled control ($^3$H-folate) under comparable test conditions, as shown in FIG. 1A.

The finding that the alpha and gamma isomers are equivalent in their ability to compete with native folate for binding to the JAR cells is again surprising, as the results are contrary to the recent patent publication of Low, Green, et al. (WO 96/36367) which teaches away from the alpha isomer being a compound that is taken up by folate uptake mechanism(s) such that it could be used to image the distribution of the same. Even more surprising was the result obtained with the Bis(DO3A-APA)folate compound, which contains a metal chelate moiety at both the alpha and gamma carboxylates of folate; at some folate concentrations, binding of this compound was higher than that observed for the $^3$H-folate control.

EXAMPLE 18

In Vitro Efflux Studies with $^3$H folate, $^{153}$Gd-DO3A-APA-(α)- and -(γ)-folate Efflux studies were performed to examine the washout of Gd-folates or native folate from KB and JAR cells in vitro. Briefly, 250 pmol of $^3$H-folate, $^{153}$Gd-DO3A-APA-(γ)-folate or $^{153}$Gd-DO3A-APA-(α)-folate was incubated with approximately 100,000 KB or JAR cells for 30 minutes at 37° C., 5% $CO_2$. Under these conditions, KB and JAR cells were previously shown to reach saturation for folate uptake/association. At the end of the 30-min incubation period, the cells were washed five times with ice-cold media lacking folate.

These folate-loaded cells were then incubated at 37° C. for 24 hours with folate-depleted media. At predetermined intervals during this time, the incubation medium was removed and replaced with fresh medium at 37° C. The radioactivity present in each aliquot of the incubation medium was used to determine the rate at which radioactivity from the $^3$H-folate, $^{153}$Gd-DO3A-APA-(γ)-folate or $^{153}$Gd-DO3A-APA-(α)-folate washed out of the cells. At the end of the study, the cells were suspended in one ml of water and assayed for radioactivity and protein content.

The results of washout studies with the alpha and gamma isomers of Gd(DO3A-APA)-folate and native folate are compared in FIGS. 3 and 3A. The data show that when there is no added folate in the media, washout from KB and JAR cells is faster for the alpha derivative than it is for the gamma isomer or native substrate. This finding may be relevant to the in vivo situation where the levels of extracellular folate will drop after the initial bolus.

EXAMPLE 19

In Vitro Exchange Studies with $^3$H-folate, $^{153}$Gd-DO3A-APA-(α)- and -(γ)-folate Exchange studies were performed to examine the effect of native folate on the radioactivity levels in KB or JAR cells that had been pre-loaded with a saturating level of radiolabeled Gd-folates or native folate in vitro. $^3$H-folate, $^{153}$Gd-DO3A-APA-(γ)-folate or $^{153}$Gd-DO3A-APA-(α)-folate (250 pmol) was incubated with KB or JAR cells as described in Example 18. At the end of the 30-min incubation period, these $^{153}$Gd-folate or $^3$H-folate-loaded cells were washed five times with ice-cold media containing 250 nM cold, native folate and were then incubated at 37° C. for 24 hours with media that contained 250 pmol of cold folate. At predetermined intervals during this time, the incubation medium was removed and replaced with fresh medium at 37° C. The radioactivity present in each aliquot of the incubation medium was used to determine the rate at which radioactivity from the $^3$H-folate, $^{153}$Gd-DO3A-APA-(γ)-folate or $^{153}$Gd-DO3A-APA-(α)-folate washed out of the cells. At the end of the study, the cells were suspended in one ml of water and assayed for radioactivity and protein content.

Figure 4:
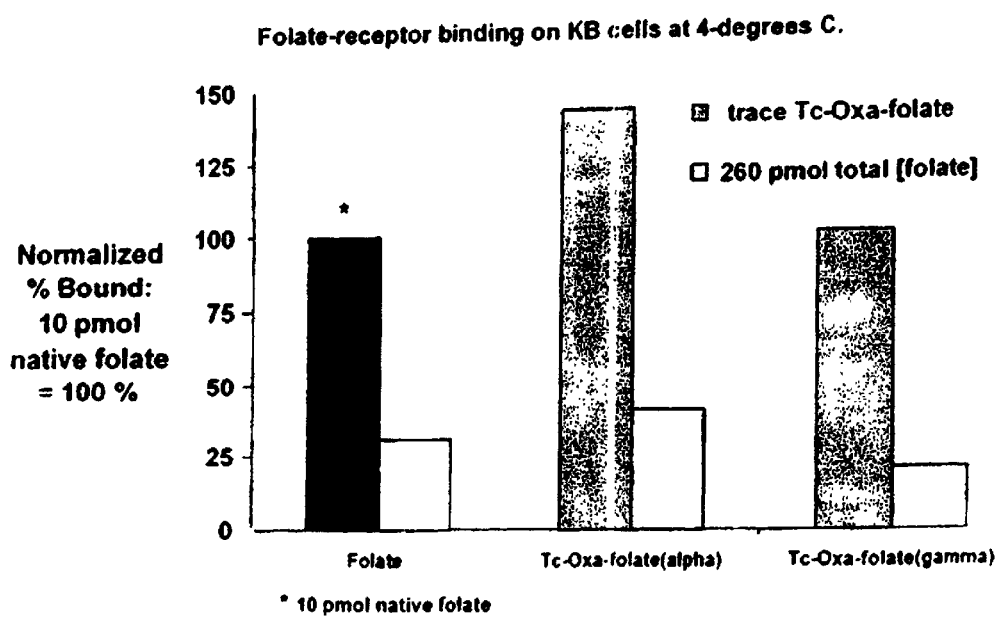
FIG. 4 shows binding of $^3$H-folate and alpha or gamma isomer of $^{99m}$Tc-Oxa-folate to KB cells at 4° C. in the presence and absence of excess folate.
Figure 4A:
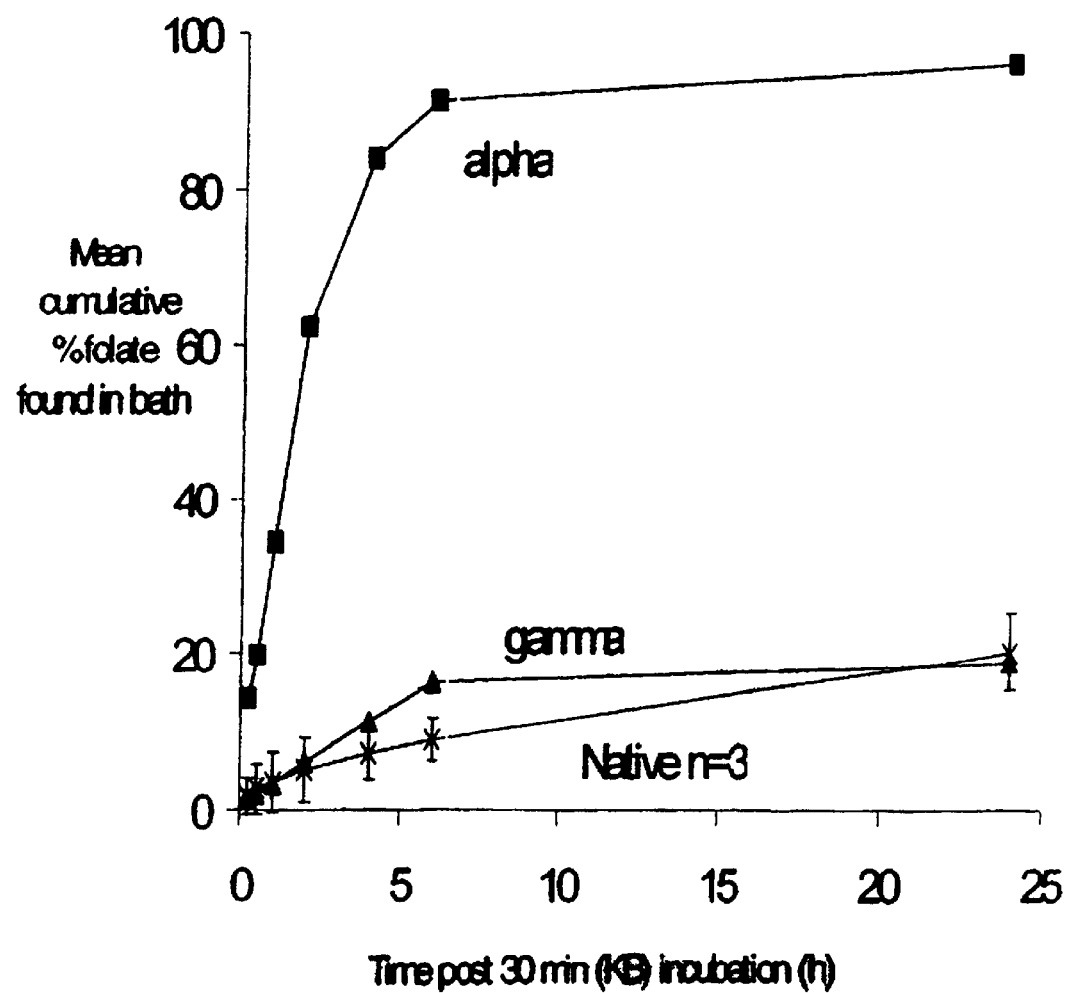
FIG. 4A shows exchange (with 250 nm cold folate in the medium) of folates from KB cells.

The results of these exchange studies in KB cells are shown in FIG. 4A. KB cells that were loaded with a saturating dose of $^{153}$Gd-DO3A-APA-(α)-folate and subsequently incubated with solutions containing cold native folate lost close to 100% of their radioactivity to the incubation bath within 24 hours, suggesting that the alpha isomer exchanges with the native folate present in the external medium. In contrast, KB cells loaded with $^3$H folate or Gd-DO3A-APA-(γ)-folate lost only 20% of the initial radioactivity in the cells to the medium over 24 hours.

Figure 4B:
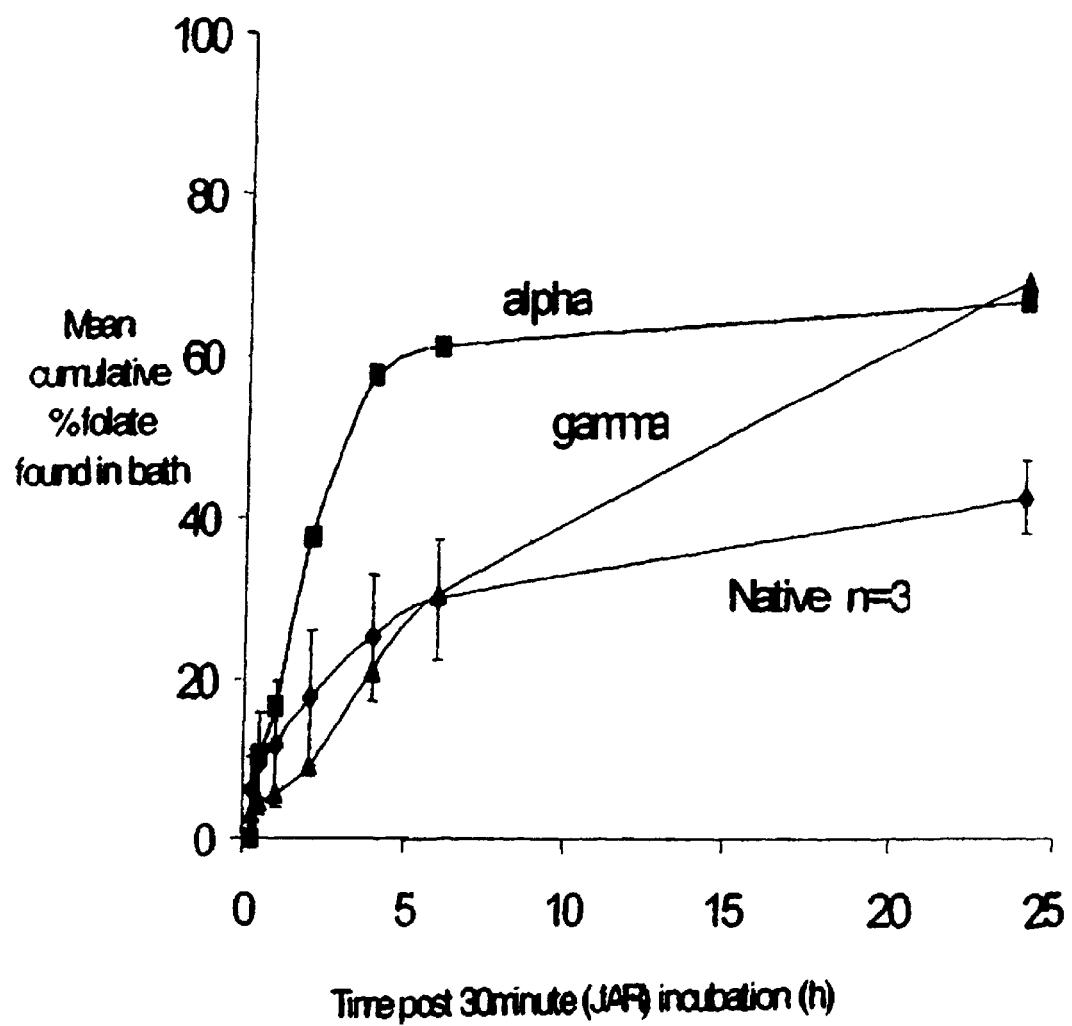
FIG. 4B shows exchange (with 250 nm cold folate in the medium) of folates from JAR cells.

The results of the exchange studies in JAR cells are shown in FIG. 4B. In this cell line, the alpha compound again showed a faster initial net rate of loss of radiolabel to the media than was observed with the gamma and native folate compounds. After 6 hours, 60% of the radioactivity from the cells loaded with the alpha isomer was found in the medium, whereas only 30% of the starting activity had been lost from JAR cells that were loaded with either Gd(DO3A-APA)-folate gamma isomer or $^3$H folate. After 24 hours the gamma isomer and native folate also showed significant net loss of activity from the JAR cells to the medium. At 24 hours the amounts of alpha and gamma compound that had washed from the cell were similar.

These studies demonstrate that the clearance properties of the compound derivatized at the alpha carboxylate of folate are significantly different from those of the gamma analog or underivatized native folate. In vivo, this property may be advantageous as it may serve to reduce the half-life of radioactivity in cells that bind folate analogs, which may improve the dosimetry properties of the agent. For applications in MR imaging this property may be advantageous as it may serve to reduce the biological half-life of the agent in cells that bind folate analogs, which may improve the toxicological profile of the agent.

EXAMPLE 20

Biodistribution Studies in Tumor-bearing Nude Mice at "Tracer" Doses of Gd-DO3A-APA-(α)-folate, Gd-DO3A-APA-(γ)-folate and Bis(Gd-DO3A-APA)-folate To define the ability of the complexes of this invention to target folate-binding protein-expressing tumor cells in vivo, distribution studies were conducted in female athymic (Nu/Nu) mice that were implanted with KB or JAR tumors. The mice were maintained on an ad libitum folate-depleted diet (gamma-irradiated Purina folate-deficient basal diet 5831C-2 with 1% succincyl sulphathiazole) beginning two weeks prior to inoculation. This diet was maintained throughout the duration of the study. The mice were inoculated subcutaneously in the scapular region with 0.1 mL of a tumor cell suspension containing 4×10$^6$ KB or JAR cells. When tumors had grown to 0.2–0.4 cm$^3$ (2–4 weeks), animals were anesthetized (100 mg ketamine/kg, i.m. and 10 mg xylazine/kg i.p.) and a "trace" dose (0.08 nmol/kg) of either $^{153}$Gd-DO3A-APA-(α)-folate, $^{153}$Gd-DO3A-APA-(γ)-folate or Bis($^{153}$Gd-DO3A-APA)-folate in a volume of 0.2 mL was delivered via tail-vein injection (n=3 animals/compound). Thirty minutes post injection, the mice were sacrificed and selected organs were removed, weighed, and assayed for radioactivity, in order to determine the % injected dose/g-tissue (% ID/g) and the % injected dose/organ (% ID/organ), following procedures known to those skilled in the art. The 30 min tumor and kidney biodistribution results obtained following a tracer (0.08 nmol/kg) dose of Gd-folate are shown in Table I. These data show that the % ID/g in tumor is comparable for all three compounds studied. This result is surprising in light of Low, Green et al, who teach that folates derivatized in the alpha position have little affinity for KB cells in vitro, and by extension, in vivo. The data further show that the % ID/g in kidney is higher for Gd-DO3A-APA-(γ)-folate than it is for the two compounds that are derivatized in the alpha position (Gd-DO3A-APA-(α)-folate and Bis(Gd-DO3A-APA)-folate.

TABLE I

| Distribution data: KB Mice (N = 3/data set @ 30 min) (0.08 nmol/kg) | Gd-DO3A-APA-(α)-folate | Bis(Gd-DO3A-APA)-folate | Gd-DO3A-APA-(γ)-folate |
| --- | --- | --- | --- |
| % ID/g-tumor | 7.7 (1.3) | 5.9 (0.8) | 8.9 (2.0) |
| % ID/g kidneys | 39.0 (2.4) | 47 (6) | 58.4 (8.3) |

These results suggest that the radiation dose to kidney that is provided by the two radiolabeled folate compounds that are derivatized in the alpha position will be lower than that provided by the compound that is only derivatized at the gamma carboxylate. Improved kidney dosimetry is attained without adversely affecting tumor radioactivity levels, which are roughly comparable for all three compounds. As radiation background from kidney will interfere with the ability to image folate-receptor positive tissues in adjacent tissues (e.g. ovarian and uterine tumors), substitution at the alpha position may provide a distinct advantage. Implications for the radiation dose provided by alpha-substituted radiotherapeutic folate derivatives to target and non-target tissues are obvious.

Improved results with alpha-derivatized complexes were also seen in a study that compared the levels of radioactivity found in the kidney and urine following a 0.08 nmol/kg dose of one of the three radiolabeled $^{153}$Gd-folate derivatives. Data obtained at 30 and 60 minutes post injection are shown in Table II.

TABLE II

| Compound: dose | % ID/Organ (S.D.) at 30 or 60 min Post Injection | | | |
| --- | --- | --- | --- | --- |
| | Kidneys: | | Urine/Bladder: | |
| 0.08 nmol/kg | 30 min | 60 min | 30 min | 60 min |
| Gd-DO3A-APA-(α)-folate | 116.5 (1.1) (N = 3,KB) | 21.0 (1.8) (n = 2,JAR) | 23.3 (5.2) (N = 3,KB) | 21.6 (2.4) (N = 2,JAR) |
| Bis(Gd-DO3A-APA)-folate | 17.5 (1.7) (N = 6,KB/JAR) | 17.8 (3.0) (N = 2,JAR) | 18.5 (7.7) (N = 6,KB/JAR) | 30.3 (5.0) (N = 2,JAR) |
| Gd-DO3A-APA-(γ)-folate | 19.8 (1.1) (N = 3,KB) | 34.3 (7.0) (N = 3,JAR) | 3.3 (9.6) (N = 3,KB) | 5.2 (1.6) (N = 2,JAR) |

Radioactivity in the kidney following injection of the gamma-folate derivative was higher than that for the alpha and bis derivatives at both 30 and 60 minutes. The amount of radioactivity in the urine and bladder for the alpha compounds was different from that observed with the gamma isomer. Between 20 and 30% of the radioactivity was excreted for the alpha and bis compounds over one hour. In contrast the gamma-Gd(folate) compound did not show any appreciable renal excretion even at 60 min.

EXAMPLE 21

Biodistribution Studies in Tumor-bearing Nude Mice at "MRI" Dose Levels (0.1 mmol/kg) of $^{153}$Gd/Gd-DO3A-APA-(α)-folate, $^{153}$Gd/Gd-DO3A-APA-(γ)-folate and Bis($^{153}$Gd/Gd-DO3A-APA) folate Biodistribution studies were performed using female nu/nu mice implanted with subcutaneous JAR tumors using the general procedures described in the example above. Animals were sacrificed 60 min post IV injection of an "MRI" dose level (0.1 mmol/kg) of $^{153}$Gd/Gd-DO3A-APA-(α)-folate, $^{153}$Gd/Gd-DO3A-APA-(γ)-folate or Bis($^{153}$Gd/Gd-DO3A-APA)folate and selected organs were removed, weighed, and assayed for radioactivity, in order to determine the % injected dose/g-tissue (% ID/g) in the tumors. The data obtained in JAR tumors are shown in Table III.

TABLE III

| Mean % ID/g-JAR Tumor (60 min) 100 μmol/kg dose | Tissue | Tumor % ID/g | [Gd] in tumor tissue (μM) |
|---|---|---|---|
| $^{153}$Gd/Gd-DO3A-APA-(α)-folate (N = 4) | JAR Tumor | 2.43 (0.71) | 55 (20) |
| $^{153}$Gd/Gd-DO3A-APA-(γ)-folate (N = 3) | JAR Tumor | 1.83 (0.87) | 44 (20.8) |
| Bis($^{153}$Gd/Gd-DO3A-APA)folate (n = 3) (79.2 μmol/kg dose) | JAR Tumor | 1.48 (0.12) | 55 (4) |

The % ID/g values in tumor 60 min post injection of a 0.1 mmol/kg dose were comparable for the Gd-DO3A-APA-(α) and (γ)-folate and Bis complexes. This result was surprising in light of the reports of Wang et al. and the patent of Low et al. as uptake of the alpha derivatized compounds would not be expected based on literature teachings. The concentration of gadolinium in these tumors was calculated from the observed % ID/g values, and it was found the gadolinium concentrations achieved in the tumors with all three Gd-folate compounds were sufficient to provide detectable enhancement of the MRI signal from the tumor. Kidney localization was also noted for all three compounds, suggesting MRI applications for these compounds in selective enhancement of the signal intensity from kidney as well as tumor.

EXAMPLE 22

Biological Evaluation of the Alpha and Gamma Isomers of $^{99m}$Tc-oxa-folate in KB Cells The ability of the alpha and gamma isomers of $^{99m}$Tc-oxa-folate to bind to KB cells was studied at 4° C. KB cells (~5×10$^5$ cells/well) were seeded into 35-mm wells and incubated for 48 hours as described in example 17 above. The alpha and gamma isomers of $^{99m}$Tc-oxa-folate, were prepared and purified as described in examples 14 and 16.

The cells were then cooled to 4° C. for 30 min and incubated with the following mixtures for 30min at 4° C.:

1. 10 pmol of $^3$H-folate
2. 10 pmol of $^3$H-folate and 250 pmol of native folate
3. Trace amounts (~0.5 μCi) of $^{99m}$Tc-Oxa-α-folate
4. Trace amounts (~0.5 μCi) of $^{99m}$Tc-Oxa-α-folate and 260 pmol of native folate
5. Trace amounts (~0.5 μCi) of $^{99m}$Tc-Oxa-γ-folate
6. Trace amounts (~0.5 μCi) of $^{99m}$Tc-Oxa-γ-folate and 260 pmol of native folate Following the incubation period, the cells were washed 3 times with ice-cold Tris-buffered saline. The cells were then stripped from the plates using 1.0 mL of water. Aliquots of the water/cell mixture were assayed for the respective radio-isotopes and for cellular protein (to determine the number of KB cells present in each well). The radioassay data were used to calculate the % of radiolabeled compound bound to the cells in the absence and presence of unlabeled native folate. The results from this study are given in FIG. 4. Data in FIG. 4 are presented as the percentage bound, relative to the % bound in the control wells containing 10 pmol of $^3$H-folate.

These data indicate that when $^{99m}$Tc-Oxa-folate was incubated with KB cells for 30 min at 4° C., the γ-isomer of $^{99m}$Tc-Oxa-folate bound to the KB cells to the same extent as that observed with 10 pmol of $^3$H-folate; binding observed with the alpha isomer of $^{99m}$Tc-Oxa-folate was 140% of that observed with 10 pmol of $^3$H-folate. (FIG. 4, dark bars).

These binding experiments were repeated in the presence of 250–260 pmol of cold native folate, to determine if the addition of excess cold folate would cause a decrease in the quantity of $^3$H or $^{153}$Gd bound to the KB cells at the end of the experiment. Such a result is expected if the radiolabeled compounds and native folate compete for binding to folate binding protein on the KB cells and an excess of cold folate is added. The results observed (FIG. 4, white bars) indicate that both native folate and the alpha and gamma isomers of $^{99m}$Tc-Oxa-folate do compete for folate binding protein on the KB cells, and that the addition of 250 pmol of cold folate causes a similar effect on the degree of binding of 10 pmol $^3$H-folate as it does on the binding of 10 pmol of either the alpha or gamma isomer of $^{99m}$Tc-Oxa-folate.

Having described the invention, it is understood that changes and modifications may be effected within the spirit and scope of the invention.

What is claimed is:

1. A diagnostic, therapeutic or radiotherapeutic or chemotherapeutic composition for visualization, therapy, chemotherapy or radiotherapy of tissues or organs that overexpress folate-binding protein comprising:

a) folate-receptor binding ligand comprising one or more folate-receptor binding moieties, at least one of which is conjugated through its alpha carboxylate via an optional linking group to one or more macrocyclic or non-macrocyclic metal-chelating ligand radicals that are optionally chelated to paramagnetic, superparamagnetic, radioactive or non-radioactive metals for detection outside the body by imaging means for diagnosis or for providing a therapeutic, chemotherapeutic, or radiotherapeutic effect; wherein said folate receptor binding ligand has the structure of formula II:

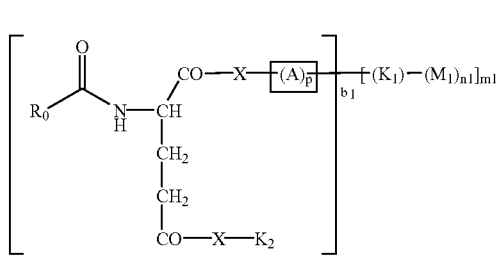

wherein $R_0$ is a folate-receptor binding residue of formula:

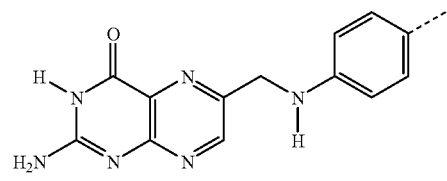

or

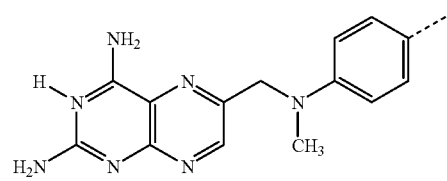

each X is independently —O—, —S—, —NH—, or —$NR_1$—;
n1 is 0 or 1;
b1 is 1 to 3;
m1 is 1 to 81;
each $K_1$ is independently
  a) a macrocyclic or non-macrocyclic metal-chelating ligand radical that is optionally chelated to a paramagnetic, superparamagnetic, radioactive or non-radioactive metal $M_1$, or
  b) a chemotherapeutic drug;
—$K_2$ is —H, -alkyl, -alkenyl, -alkynyl, -alkoxy, -aryl, -alkyl, —$CON(R_2)_2$, -glutamate, -polyglutamate, or —$K_3$;
—$K_3$ is

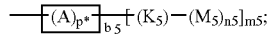

wherein
  —$K_5$ is either
    a) a macrocyclic or non-macrocyclic metal-chelating ligand that is optionally chelated to a paramagnetic, superparamagnetic, radioactive or non-radioactive metal $M_5$, or
    b) a chemotherapeutic drug
n5 is 0 or 1;
b5 is 1 to 3;
m5 is 1 to 81;
—(A)p— and —(A)p*— are each independently optional linkers comprising a straight or branched chain wherein the moieties "A" are the same or different and selected from the group consisting of: —$CH_2$—, —$CHR_3$—,
—$CR_4R_5$—, —CH=CH—, —CH=$CR_6$—, >$CR_7$—$CR_8$<, —C=C—, —$CR_9$=$CR_{10}$—, —C≡C—, -cycloalkylidene-, -cycloalkenyl-, -arylidene-, -heterocyclo-, carbonyl (—CO—), —O—, —S—, —NH—, —HC=N—, —$CR_{11}$=N—, —$NR_{12}$—, —CS—,

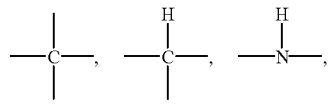

and
p and p* are independently 0 to 24, or —X—[(A)]p— and —X—[(A)p]*- may each independently be the group —Q— wherein —Q— is —[C(R')(R'')]$_{s1}$—[C(t)($R_{21}$)]$_{s2}$—[C($R_{22}$)($R_{23}$)]$_{s3}$—X3-Y—X4—;
wherein
  each s1, s2, s3, and s4 is independently 0 to 2; each X3, X4, X5, and X6 is independently a single bond, —O—, —S—, or —N($R_{24}$)—;
  Y is a single bond, —C($R_{25}$)($R_{26}$)—, or Y1 wherein, Y1 is —C(=X5)—X6—W—, wherein
  W is a single bond, -alkylidene-, -cycloalkylidene-, -arylidene-, alkenylidene-, or -alkynylidene-, whose carbon atoms may or may not be substituted;
  t is H, $R_{27}$, —C(O)$OR_{28}$, —P(O)($OR_{29}$)OH, —P(O)($OR_{30}$)$OR_{31}$, —P(O)($OR_{32}$)$R_{33}$, —P(O)(OH)$R_{34}$, —C(O)N($R_{35}$)($R_{36}$), or C(O)NH($R_{37}$);
each R' and R'' is independently a single bond, H, alkyl, alkoxy, cycloalkyl, hydroxyalkyl, aryl, or heterocyclo, each of which is optionally substituted,
each $R_3$ through $R_5$, $R_7$, $R_8$, $R_{21}$ through $R_{23}$, and $R_{25}$ through $R_{27}$ is independently H, alkyl, alkoxy, halogen, hydroxy, cycloalkyl, hydroxyalkyl, aryl, or heterocyclo, each of which is optionally substituted;
each $R_1$, $R_2$, $R_6$, $R_9$ through $R_{12}$, $R_{24}$, and $R_{28}$ through $R_{37}$ is independently H, alkyl, alkenyl, cycloalkyl, aryl, a 5- or 6- membered nitrogen or oxygen containing heterocycle;
wherein
  —$K_2$ is

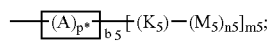

and both —$K_1$ and —$K_5$ are macrocyclic or non-macrocyclic metal chelates that are each optionally chelated to radioactive, nonradioactive, paramagnetic or superparamagnetic metals $M_1$ or $M_5$;
wherein —[(A)p]—$K_1$ and —[(A)p*]—$K_5$ are each in their entirety, polydentate ligands radicals of formula IIIa–IIIc;

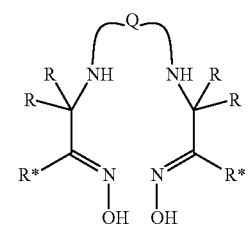

IIIa

-continued

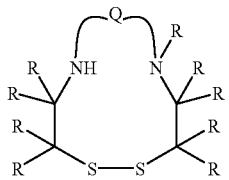
IIIb

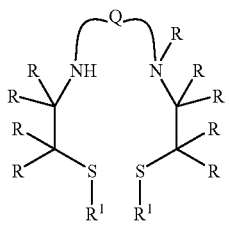
IIIc wherein
Q is the group —(C(RR))$_{m1}$—Y$^1$(C(RR))$_{m2}$—(Y$^2$—(C(RR))$_{m3}$)$_{n-}$, wherein
Y$^1$ and Y$^2$ are independently —CH$_2$—, —NR—, —O—, —S—, —SO—, —SO$_2$— or —Se—;
n is 0 or 1; and m1, m2 and m3 are integers independently selected from 0 to 4, provided that the sum of m1 and m2 is greater than zero;
all R and R* groups are independently —R$_4$, —Cl, —F, —Br, —OR$^5$, —COOR$^5$, —CON(R$^5$)$_2$, —N(R$^5$)$_2$, -alkyl-COOR$^5$, -alkyl-C(O)—N(R$^5$)$_2$; -alkyl-N(R$^5$)$_2$; —C(O)OR$^5$; —C(O)N(R$^5$)$_2$; -aryl-N(R$^5$)$_2$; acyl; acyloxy; heterocyclo; hydroxyalkyl; —SO$_2$—R$^5$; -alkyl-SO$_2$—R$^5$; or —R$^3$;
wherein
each —[R$^3$]— is, in its entirety, the linking group —[(A)p]— or —[(A)p*]— that serves to couple the metal chelating ligand radical to —X—;
each —R$^4$ is independently —H, -alkyl, -alkoxy, -hydroxy, -cycloalkyl, hydroxyalkyl, -aryl, or -heterocyclo, each of which is optionally substituted;
each —R$^5$ is independently —H, -alkyl, -aryl, -cycloalkyl or -hydroxyalkyl, each of which is independently substituted;
with the provisos that a carbon atom bearing an R group is not directly bonded to more than one heteroatom; and
at least one R or R* group on each —K$_1$ and —K$_5$ is —[R$^3$]—;
or a pharmaceutically acceptable salt thereof; in a pharmaceutically acceptable carrier.

2. The composition of claim 1 wherein both —K$_1$ and —K$_5$ are metal-chelating ligand radicals of formula V:

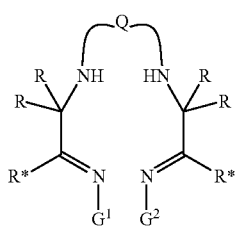
V wherein
—Q— is the group —(C(RR))$_{m1}$—(Y$^1$)$_n$—(C(RR))$_{m2}$—(Y$^2$—(C(RR))$_{m3}$)$_{n1}$;
Y$^1$ and Y$^2$ are each independently —CH$_2$—, —NR$^5$—, —O—, —S—, —SO—, —SO$_2$— or —Se—;
n and n1 are each independently 0 or 1; and m1, m2 and m3 are independently 0 or an integer from 1 to 4; provided that m1 and m2 are not both 0, that m1+m2+n+n1 is less than 6 and that a carbon atom bearing an R group is not directly bonded to more than one heteroatom;
each —R and —R* group is independently: —R$^4$; -alkoxy; -hydroxy; -halogen, especially fluoro; -haloalkyl; —OR$^5$; —C(O)—R$^5$, —C(O)—N(R$^5$)$_2$, —N(R$^5$)$_2$, —N(R$^5$)—COR$^5$; -alkyl-C(O)—OR$^5$, -alkyl-C(O)—N(R$^5$)$_2$, -alkyl-N(R$^5$)$_2$—, -alkyl-N(R$^5$)—COR$^5$, -aryl-C(O)—OR$^5$, -aryl-C(O)—N(R$^5$)$_2$, aryl-N(R$^5$)$_2$—, -aryl-N(R$^5$)—COR$^5$, -nitrile, -acyl, -acyloxy, -heterocyclo, -hydroxyalkyl, alkoxyalkyl, hydroxyaryl, arylalkyl, —SO$_2$—R$^5$, -alkyl-SO$_2$—R$^5$, or —[R$^3$]—
wherein
each —[R$^3$]— is, in its entirety, the linking group —[(A)p]— or —[(A)p*]— that serves to couple the metal chelating ligand radical —K$_1$ or —K$_5$ to —X—;
each —R$^4$ is independently —H, -alkyl, -alkoxy, -hydroxy, -cycloalkyl, -hydroxyalkyl, -aryl, or -heterocyclo, each of which is optionally substituted;
each —R$^5$ is independently —H, -alkyl, -aryl, -cycloalkyl or -hydroxyalkyl, each of which is optionally substituted; or
two R groups, or an R group and an R* group, taken together with the one or more atoms to which they are bonded, form a saturated or unsaturated, spiro or fused, carbocyclic (such as fused 1,2-phenyl) or heterocyclic ring which may be unsubstituted or substituted by one or more groups R or R* groups above;
each G$^1$ and G$^2$ is independently —OH or —(NR$^6$)$_2$; with the proviso that at least one of G$^1$ or G$^2$ is —(NR$^6$)$_2$, where each R$^6$ is independently hydrogen, alkyl, aryl, acyl or —[R$^3$]—; and
A is a linking group; and p is 0 or a positive integer;
with the proviso that at least one R, R*, or R$^6$ group is —[R$^3$]—;
or a pharmaceutically acceptable salt thereof.

3. A diagnostic, therapeutic or radiotherapeutic composition for visualization, therapy or radiotherapy of tissues or organs that overexpress folate-binding protein using nuclear medicine, magnetic resonance imaging or neutron capture radiotherapy applications comprising;

a) a folate-receptor binding ligand and
b) a pharmaceutically acceptable carrier wherein said folate-receptor binding ligand has the structure of formula IIb:

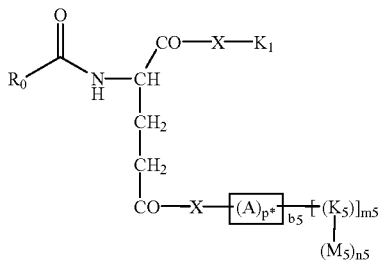

IIb wherein
—$K_1$ is —H, -alkyl, -alkenyl, -alkynyl, -alkoxy, -aryl, -alkyl, —$CON(R_2)_2$, -glutamate, or -polyglutamate;
—$K_5$ is a polydentate metal chelating ligand;
$M_5$ is a radioactive, paramagnetic or superparamagnetic metal;
each —X— is independently —O—, —S—, —NH—, or —$NR_1$—;
b5=1 to 3, m5=1; n5 is 0 or 1;
—$R_0$ is a folate-receptor binding residue of formula:

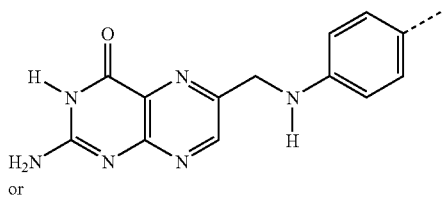

or

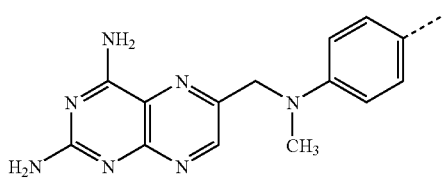

each —[(A)p*]— is an optional linker independently comprising a straight or branched chain made up of "p*" individual (A) moieties that are the same or different and are selected from the group consisting of: —$CH_2$—, —$CHR_3$—, —$CR_4R_5$—, —CH=CH—, —CH=$CR_6$—, >$CR_7$—$CR_8$<, >C=C<, —$CR_9$=$CR_{10}$—, —C≡C—, -cycloalkylidene-, -cycloalkenyl-, -arylidene-, -heterocyclo-, carbonyl (—CO—), —O—, —S—, —NH—, —HC=N—, —$CR_{11}$=N—, —$NR_{12}$—, —CS—, and

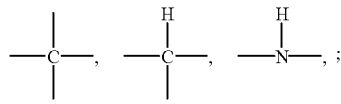

and p* is 0 to 24;
or —X—[(A)]p*— is, in its entirety, the group —Q— wherein
—Q— is —[C(R')(R")]$_{s1}$—[C(t)(R$_{21}$)]$_{s2}$—[C(R$_{22}$)(R$_{23}$)]$_{s3}$—X3—Y—X4—;
wherein
s1, s2, s3, and s4 are independently 0 to 2;
X3, X4, X5, and X6 are independently a single bond, —O—, —S—, or —N(R$_{24}$)—;

Y is a single bond, —C(R$_{25}$)(R$_{26}$)—, or —Y1—
wherein
Y1 is —C(=X5)—X6—W—, wherein
W is a single bond, -alkylidene-, -cycloalkylidene-, -arylidene-, -alkenylidene-, or -alkynylidene-, whose carbon atoms are optionally substituted;
t is H, R$_{27}$, —C(O)OR$_{28}$, —P(O)(OR$_{29}$))OH, —P(O)(OR$_{30}$))OR$_{31}$, —P(O)(OR$_{32}$)R$_{33}$, —P(O)(OH)R$_{34}$—C(O)N(R$_{35}$)(R$_{36}$), or C(O)NH(R$_{37}$);
each —R' and —R" is independently a single bond, —H, -alkyl, -alkoxy, -cycloalkyl, -hydroxyalkyl, -aryl, or -heterocyclo, each of which is optionally substituted,
each —R$_3$ through —R$_5$, —R$_7$, —R$_8$, —R$_{21}$ through —R$_{23}$, and —R$_{25}$ through —R$_{27}$ is independently —H, -alkyl, -alkoxy, -halogen, -hydroxy, -cycloalkyl, -hydroxyalkyl, -aryl, or -heterocyclo, each of which is optionally substituted;
each —R$_1$, —R$_2$, —R$_6$, R$_9$ through —R$_{12}$, —R$_{24}$, and —R$_{28}$ through —R$_{37}$ is independently —H, -alkyl, -alkenyl, -cycloalkyl, -aryl, or a 5- or 6-membered nitrogen or oxygen containing heterocycle;
wherein —K$_5$ is a polydentate metal-chelating ligand radical of formula V:

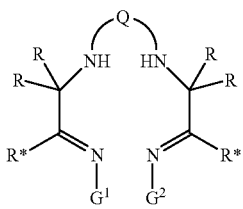

V wherein
Q is the group —(C(RR))$_{m1}$—(Y$^1$)$_n$—(C(RR))$_{m2}$—(Y$^2$—(C(RR))$_{m3}$)$_{n1}$;
Y$^1$ and Y$^2$ are each independently —CH$_2$—, —NR—, —O—, —S—, —SO—, —SO$_2$— or —Se—;
n and n1 are each independently 0 or 1; and m1, m2 and m3 are independently 0 or an integer from 1 to 4; provided that m1 and m2 are not both 0, that m1+m2+n+n1 is less than 6 and that a carbon atom bearing an R group is not directly bonded to more than one heteroatom;
each R and R* group is independently; —H, —R$_4$; -alkoxy; -hydroxy; -halogen, -haloalkyl, —OR$^5$, —C(O)—R$^5$, —C(O)—N(R$^5$)$_2$, —N(R$^5$)$_2$, —N(R$^5$)—COR$^5$, -alkyl-C(O)—OR$^5$, -alkyl-C(O)—N(R$^5$)$_2$, -alkyl-N(R$^5$)$_2$—, -alkyl-N(R$^5$)—COR$^5$, -aryl-C(O)—OR$^5$, -aryl-C(O)—N(R$^5$)$_2$—, -aryl-N(R$^5$)$_2$—, -aryl-N(R$^5$)—COR$^5$, -nitrile, -acyl, -acyloxy, -heterocyclo, -hydroxyalkyl, -alkoxyalkyl, -hydroxyaryl, -arylalkyl, —SO$_2$—R$^5$, -alkyl-SO$_2$—R$^5$, or —[R$^3$]—;
wherein
each —[R$^3$]— is, in its entirety, the linking group —[(A)p*]— that serves to couple the metal chelating ligand radical —K$_5$ to —X—;
each —R$^4$ is independently —H, -alkyl, -alkoxy, -hydroxy, -cycloalkyl, -hydroxyalkyl, -aryl, or -heterocyclo, each of which is optionally substituted;
each —R$^5$ is independently —H, -alkyl, -aryl, -cycloalkyl or -hydroxyalkyl, each of which is independently substituted; or two R groups, or an R* group, taken together with the one or more atoms to which they are bonded, form a saturated or unsaturated, spiro or fused, carbocyclic or heterocyclic ring which is optionally substituted by one or more groups R or R* groups above;

each —$G^1$ and —$G^2$ is independently —OH or —$(NR^6)_2$; with the proviso that at least one of —$G^1$ or —$G^2$ is —$(NR^6)_2$, where each —$R^6$ is independently -hydrogen, -alkyl, -aryl, -acyl or —$[R^3]$—; and A is a linking group; and p is 0 or a positive integer; with the proviso that at one to three —R, —R*, or —$R^6$ groups is —$[R^3]$—;

or a pharmaceutically acceptable salt thereof.

4. The composition of claim 3 wherein $M_1$ or both $M_1$ and $M_5$ are paramagnetic or superparamagnetic metals and $K_1$ or both —$K_1$ and —$K_5$ are enhanced relaxivity polyaza macrocyclic radicals of formula VI;

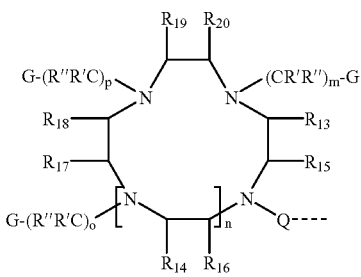

VI wherein n is 0 or 1;

each m, o, and p is independently 1 or 2;

Q is —$[C(R')(R'')]_{s1}$—$[C(t)(R_{21})]_{s2}$—$[C(R_{22})(R_{23})]_{s3}$—X3—Y—X4—; wherein s1, s2, s3, and s4 are independently 0 to 2;

Y is a single bond, —$C(R_{25})(R_{26})$—, or Y1 wherein, Y1 is —C(=X5)—X6—W—, wherein W is a single bond, -alkylidene-, -cycloalkylidene-, -arylidene-, -alkenylidene-, or -alkynylidene-, whose carbon atoms are optionally substituted;

t is H, $R_{27}$, —$C(O)OR_{28}$, —$P(O)(OR_{29}))OH$, —$P(O)(OR_{30}))OR_{31}$, —$P(O)(OR_{32})R_{33}$, —$P(O)(OH)R_{34}$—C(O)N($R_{35}$)($R_{36}$), or C(O)NH($R_{37}$);

each G is independently —C(O)OR''', —P(O)(OR''')OH, —P(O)(OR''')_2, —P(O)(OR''')R'', —P(O)(OH)R''C(O)N(R''')_2, or C(O)NH(R''');

each —R' and —R'' is independently a single bond, —H, -alkyl, -alkoxy, -cycloalkyl, hydroxyalkyl, -aryl, or -heterocyclo, each of which is optionally substituted, each —R''' is independently a —H, -alkyl, -cycloalkyl, -hydroxyalkyl, -aryl, or -heterocyclo, each of which is optionally substituted, each —$R_{13}$ through —$R_{23}$, and —$R_{25}$ through —$R_{27}$ is independently —H, -alkyl, -alkoxy, -halogen, -hydroxy, -cycloalkyl, -hydroxyalkyl, aryl, or -heterocyclo, each of which is optionally substituted;

each —$R_{24}$, and —$R_{28}$ through —$R_{37}$ is independently —H, -alkyl, -alkenyl, -cycloalkyl, -aryl, a 5- or 6-membered nitrogen or oxygen containing heterocycle, each of which is optionally substituted;

or $R_{13}$ together with $R_{15}$, and $R_{17}$ together with $R_{18}$, independently form, together with the carbon atoms in the polyazamacrocycle to which they are attached, a fused fully or partially saturated non-aromatic cyclohexyl ring which are optionally substituted by one or more halogen, alkyl, ether, hydroxy, or hydroxyalkyl groups, and which are optionally fused to a carbocyclic ring, or $R_{13}$ and $R_{15}$ are each hydrogen and $R_{17}$, together with $R_{18}$, forms a fused fully or partially saturated non-aromatic cyclohexyl ring as defined above, or $R_{13}$, together with $R_{15}$, forms a fused fully or partially saturated non-aromatic cyclohexyl ring as defined above, and $R_{17}$ and $R_{18}$ are hydrogen;

or a pharmaceutically acceptable salt thereof.

5. A conjugatable polyaza macrocyclic intermediate useful for the preparation of a composition for visualization or radiotherapy of tissues or organs that overexpress folate-binding protein using magnetic resonance imaging or neutron capture therapy techniques comprising one or more folate-receptor binding residues conjugated to one or more enhanced relaxivity polyaza macrocyclic radicals which are optionally chelated to a paramagnetic or superparamagnetic metal capable of either being detected outside the body by imaging means for diagnosis or capable of providing a radiotherapeutic effect using neutron capture therapy; wherein said folate-receptor binding compound has the structure of formula IIc:

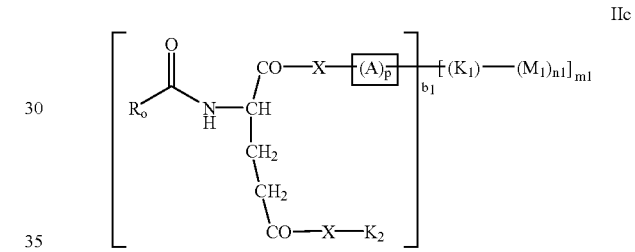

IIc wherein $R_0$ is a folate-receptor binding moiety of formula:

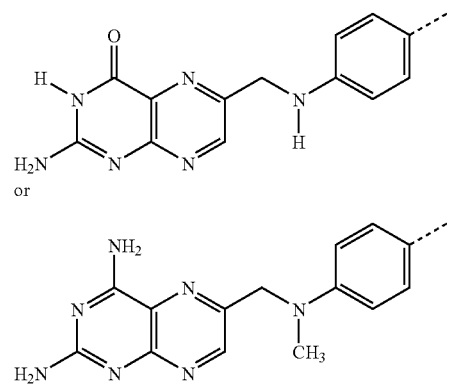

each X is independently —O—, —S—, —NH—, or —$NR_1$—;

n1 and n5 are independently 0 or 1;

b1 and b5 are independently 1 to 3;

m1 and m5 are independently 1 to 81;

each —$K_1$ is independently —H, -alkyl, -alkenyl, -alkynyl, -alkoxy, -aryl, -alkyl, —CON($R_2$)_2, -glutamate, -polyglutamate, or —$K_4$;

each —$K_2$ is independently —H, -alkyl, -alkenyl, -alkynyl, -alkoxy, -aryl, -alkyl, —CON($R_2$)_2, -glutamate, -polyglutamate, or —$K_3$;

—K₃ is

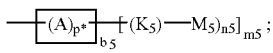

M₁ and M₅ are paramagnetic or superparamagnetic metals; and

—K₄ and —K₅ are each independently enhanced-relaxivity polyaza macrocyclic metal-chelating ligand radicals of formula VI that are optionally chelated to M₁ and M₅;

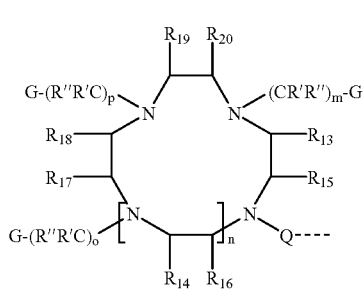

wherein
n is 0 or 1;
each m, o, and p is independently 1 or 2;
Q is —[C(R')(R")]ₛ₁—[C(t)(R₂₁)]ₛ₂—[C(R₂₂)(R₂₃)]ₛ₃—X3—Y—X4—; wherein
s1, s2, s3, and s4 are independently 0 to 2;
X3, X4, X5, and X6 are independently a single bond, —O—, —S—, or —N(R₂₄)—;
Y is a single bond, —C(R₂₅)(R₂₆)—, or Y1, wherein Y1 is —C(=X5)—X6—W—, wherein
W is a single bond, -alkylidene-, -cycloalkylidene-, -arylidene-, -alkenylidene-, or -alkynylidene-, whose carbon atoms are optionally substituted;
t is H, R₂₇, —C(O)OR₂₈, —P(O)(OR₂₉))OH, —P(O)(OR₃₀))OR₃₁, —P(O)(OR₃₂)R₃₃, —P(O)(OH)R₃₄—C(O)N(R₃₅)(R₃₆), or C(O)NH(R₃₇);
each G is independently —C(O)OR''', —P(O)(OR''')OH, —P(O)(OR''')₂, —P(O)(OR''')R'', —P(O)(OH)R''C(O)N(R''')₂, or C(O)NH(R''');
each R' and R" is independently a single bond, —H, -alkyl, -alkoxy, -cycloalkyl, -hydroxyalkyl, -aryl, or -heterocyclo, each of which is optionally substituted,
each R''' is independently —H, -alkyl, -cycloalkyl, -hydroxyalkyl, -aryl, or -heterocyclo, each of which is optionally substituted,
each —R₁₃ through —R₂₃, and —R₂₅ through —R₂₇ is independently —H, -alkyl, -alkoxy, -halogen, -hydroxy, -cycloalkyl, -hydroxyalkyl, -aryl, or -heterocyclo, each of which is optionally substituted;
each —R₂₄, and —R₂₈ through —R₃₇ is independently —H, -alkyl, -alkenyl, -cycloalkyl, -aryl, a 5- or 6-membered nitrogen or oxygen containing heterocycle, each of which is optionally substituted;
or R₁₃ together with R₁₅, and R₁₇ together with R₁₈, independently form, together with the carbon atoms in the polyazamacrocycle to which they are attached, a fused fully or partially saturated non-aromatic cyclohexyl ring which may be unsubstituted or substituted by one or more halogen, alkyl, ether, hydroxy, or hydroxyalkyl groups, and which may be further fused to a carbocyclic ring, or R₁₃ and R₁₅ are each hydrogen and R₁₇, together with R₁₈, forms a fused fully or partially saturated non-aromatic cyclohexyl ring as defined above, or R₁₃, together with R₁₅, forms a fused fully or partially saturated non-aromatic cyclohexyl ring as defined above, and R₁₇ and R₁₈ are hydrogen;

—(A)p— and —(A)p*— are optional linkers each independently comprising a straight or branched chain made up of moieties that are the same or different and selected from the group consisting of; —CH₂—, —CHR₃—, —CR₄R₅—, —CH=CH—, —CH=CR₆—, >CR₇—CR₈<, —C=C—, —CR₉=CR₁₀—, —C≡C—, -cycloalkylidene-, -cycloalkenyl-, -arylidene-, -heterocyclo-, carbonyl (—CO—), —O—, —S—, —NH—, —HC=N—, —CR₁₁=N—, —NR₁₂—, —CS—,

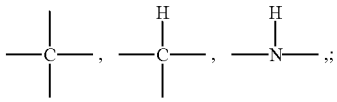

and p and p* are each individually 0 to 24;
or —X—[(A)p]— or —X—[(A)p*]— in its entirety is the group —Q— as defined above each —R₃ through —R₅, —R₇ and —R₈ is independently —H, -alkyl, -alkenyl, -alkoxy, -aryl, a 5- or 6-membered nitrogen or oxygen containing heterocycle, halogen, hydroxy or -hydroxyalkyl; and
each —R₁, —R₂, —R₆, —R₉ through —R₁₂ is independently —H, -alkyl, -alkoxy, -cycloalkyl, -aryl, -heterocyclo, -hydroxy or -hydroxyalkyl;
or a pharmaceutically acceptable salt thereof;
said intermediate containing at least one free amine, carboxylate or thiocarboxylate functionality that can be used for conjugation to targeting vectors such as folate, said intermediates having the structure of formula VIa:

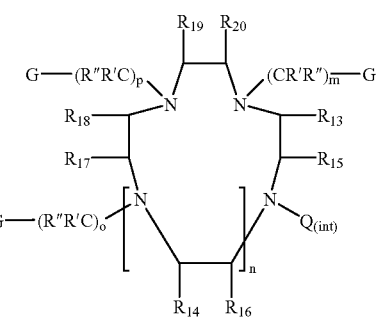

wherein
n is 0 or 1;
each m, o, and p is independently 1 or 2;
—Q(int) is a conjugatable amine-, carboxylate- or thiocarboxylate-containing group of formula —[C(R')(R")]ₛ₁—[C(t)(R₂₁)]ₛ₂—[C(R₂₂)(R₂₃)]ₛ₃—X₃—Y—X₄; wherein
s1, s2, s3, and s4 are independently 0 to 2;
X₃ is a single bond, —O—, —S—, —NH— or —NR₂₄— if Y is present, or X₃ is —OH, —SH, —NH₂ or —N(R₂₄)H if Y and X₄ are absent;
X₄ is a single bond, —OH, —COOH, —SH, —NHR₂₄ or —NH₂;

Y is a single bond, —C(R$_{25}$)(R$_{26}$)—, or Y1 wherein,
  Y1 is —C(═X5)—X6—W—, wherein
    X5 is ═O or ═S;
    X$_6$ is a single bond, —SH, —NH(R$_{38}$), —NH$_2$ or —OH if W and X4 are absent, and is —S—, —O—, —NH—, or —N(R$_{39}$)—, if W and X$_4$ are present;
  W is a single bond, or is -alkylidene-, -cycloalkylidene-, -arylidene-, -alkenylidene-, or -alkynylidene-, whose carbon atoms are optionally substituted;
  t is —H, —R$_{27}$, —C(O)OR$_{28}$, —P(O)(OR$_{29}$))OH, —P(O)(OR$_{30}$))OR$_{31}$, —P(O)(OR$_{32}$)R$_{33}$, —P(O)(OH) R$_{34}$—C(O)N(R$_{35}$)(R$_{36}$), or —C(O)NH(R$_{37}$);
  each —G is independently —C(O)OR''', —P(O)(OR''') OH, —P(O)(OR''')$_2$, —P(O)(OR''')R'', —P(O)(OH) R''—C(O)N(R''')$_2$, or —C(O)NH(R''');
    each —R' and —R'' is independently a single bond, —H, -alkyl, -alkoxy, -cycloalkyl, -hydroxyalkyl, -aryl, or -heterocyclo, each of which is optionally substituted,
    each —R''' is independently —H, -alkyl, -cycloalkyl, -hydroxyalkyl, -aryl, or -heterocyclo, each of which is optionally substituted,
    each —R$_{13}$ through —R$_{23}$, —R$_{25}$ through —R$_{27}$ is independently —H, -alkyl, alkoxy, -halogen, -hydroxy, -cycloalkyl, -hydroxyalkyl, -aryl, or -heterocyclo, each of which is optionally substituted;
    each —R$_{24}$, and —R$_{28}$ through —R$_{39}$ is independently —H, -alkyl, -alkenyl, cycloalkyl, aryl, a 5- or 6-membered nitrogen or oxygen containing heterocycle, each of which is optionally substituted;
  or R$_{13}$ together with R$_{15}$, and R$_{17}$ together with R$_{18}$, independently form, together with the carbon atoms in the polyazamacrocycle to which they are attached, a fused fully or partially saturated non-aromatic cyclohexyl ring which are optionally substituted by one or more halogen, alkyl, ether, hydroxy, or hydroxyalkyl groups, and which are optionally further fused to a carbocyclic ring, or R$_{13}$ and R$_{15}$ are each hydrogen and R$_{17}$, together with R$_{18}$, forms a fused full or partially saturated non-aromatic cyclohexyl ring as defined above, or R$_{13}$, together with R$_{15}$, forms a fused fully or partially saturated non-aromatic cyclohexyl ring as defined above, and R$_{17}$ and R$_{18}$ are hydrogen;
or a pharmaceutically acceptable thereof.

6. A composition comprising folate-receptor binding ligands and a pharmaceutically acceptable carrier for use in nuclear medicine, magnetic resonance imaging, or neutron capture therapy techniques, said folate-receptor binding ligands comprising dendrimeric first-, second-, third-, and fourth-generation conjugates containing one folate-receptor binding moiety coupled to one or more macrocyclic metal-chelating ligand radicals that are optionally chelated to paramagnetic, superparamagnetic, radioactive or non-radioactive metals for detection outside the body by imaging means for diagnosis or for providing a therapeutic or radiotherapeutic effect; wherein said folate-receptor binding compounds have the structure of formulae VIIa–VIId:

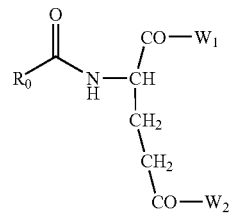

VIIa–VIId wherein R$_0$ is a folate-receptor moiety of formula:

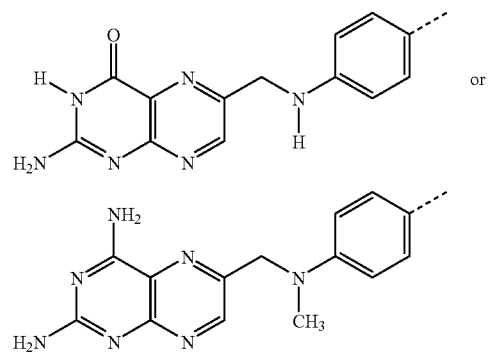

or wherein for the first generation dendrimers of formula VIIa, bearing one folate-receptor binding moiety and 3 or 6 metal chelating ligand radicals:
  W$_1$ and W$_2$ are each independently —OR''', —SR''', —NR'''R'''—CON(R$_2$)$_2$, -glutamate, -polyglutamate, or —K$_6$;
wherein each —R''' is independently -cycloalkyl, -hydroxyalkyl, or -heterocyclo;
  with the proviso that either W$_1$, W$_2$, or both W$_1$ and W$_2$ of formula VIIa must be —K$_6$, where —K$_6$ is a moiety of formula VIIIa;

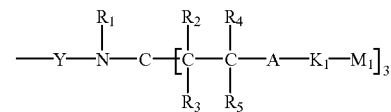

VIIIa wherein
  Y is —Y'—C(═X)— wherein
    X is ═O or ═S;
    Y' is N(R$_6$)—Z—; wherein
  Z is a single bond, -alkylidene-, -vinylidene-, -cycloalkylidene-, or -arylidene-;
  A is —C(═O)—, C(═S), or —CH$_2$—N(R$_7$)—;
  M$_1$ is a superparamagnetic, paramagnetic, radioactive or non-radioactive metal, and
  K$_1$ is a macrocyclic metal chelating ligand moiety; and,
wherein for second generation dendrimers, bearing one folate receptor binding moiety and 9 or 18 macrocyclic metal-chelating ligand radicals and having the structure of formula VIIb:
  W$_1$ and W$_2$ are each independently —OR''', —SR'''—NR'''R''', or —K$_7$, wherein each —R''' is independently —H, -alkyl, -aryl, -cycloalkyl, -hydroxyalkyl, or -heterocyclo, and —K$_7$ is a residue of formula VIIIb; with the proviso that either W$_1$, W$_2$, or both $W_1$ and $W_2$ must be $—K_7$

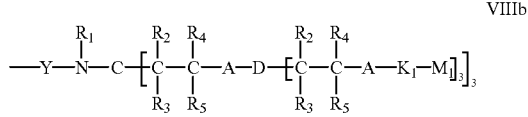

wherein

Y is a single bond or $—Y'—C(=X)—$ wherein X is $=O$ or $=S$ and Y' is $—N(R_6)—Z—$; wherein
Z is a single bond, -alkylidene-, -vinylidene-, -cycloalkylidene-, or -arylidene-;
A is $—C(O)—$, $—C(S)—$, or $—CH_2—N(R_7)—$;
D is $—N(R_6)—C—$ if A is $—C(O)—$ or $—C(S)—$ or $—C(=X_2)—E—N(R_7)—C—$ if A is $—CH_2—N(R_7)—$; wherein
E is a single bond, -alkylidene-, -vinylidene-, -cycloalkylidene-, or -arylidene- and $X_2$ is $=O$ or $=S$;

and wherein
for the third generation dendrimeric compounds of formula VIIc; bearing one folate receptor binding residue and 27 or 54 macrocyclic metal-chelating ligand radicals:
$W_1$ and $W_2$ are each independently $—OR'''$, $—SR'''$, $—NR'''R'''$, or $—K_8$ wherein each $—R'''$ is independently $—H$, -alkyl, -aryl, -cycloalkyl, -hydroxyalkyl, or -heterocyclo, and $—K_8$ is a moiety of formula VIIIc;
with the proviso that either $W_1$, $W_2$, or both $W_1$ and $W_2$ of the compounds of formula VIIc must be $—K_8$:

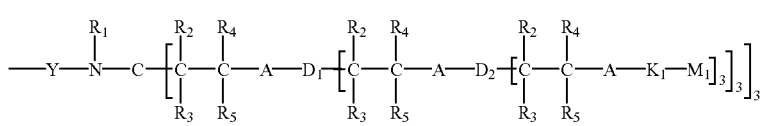

wherein,
Y is a single bond or $—Y'—C(=X)—$ wherein
X is $=O$ or $=S$;
Y' is $—N(R_6)—Z—$; wherein
Z is a single bond, -alkylidene-, -vinylidene-, -cycloalkylidene-, or -arylidene-;
A is $—C(O)—$, $—C(S)—$, or $—CH_2—N(R_7)—$;
$D_1$ and $D_2$ are each independently $—N(R_6)—C$ if A is $—C(O)—$ or $—C(S)—$, and $—C(=X_2)—E—N(R_7)—C$ if A is $—CH_2—N(R_7)—$; wherein
E is a single bond, -alkylidene-, -vinylidene-, -cycloalkylidene-, or -arylidene- and $X_2$ is $=O$ or $=S$;

and wherein for the fourth generation dendrimeric compounds of formula VIId; bearing one folate receptor binding moiety and 81 or 162 macrocyclic metal-chelating ligand radicals;
$W_1$ and $W_2$ are each independently $—OR'''$, $—SR'''$, $—NR'''R'''$ or $—K_9$, wherein each $R'''$ is independently $—H$, -alkyl, -aryl, -cycloalkyl, -hydroxyalkyl, or -heterocyclo and $—K_9$ is a moiety of formula VIIId; with the proviso that either $W_1$, $W_2$, or both $W_1$ and $W_2$ of the compounds of formula VIId must be $—K_9$);

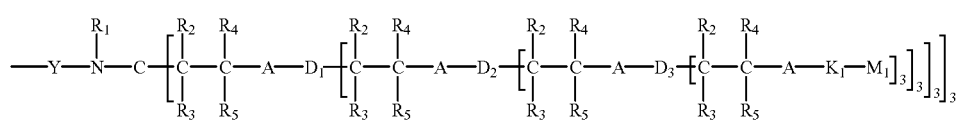

wherein Y is a single bond or $—y'—C(=X)—$ wherein
X is $=O$ or $=S$;
Y' is $—N(R_6)—Z—$; wherein
Z is a single bond, -alkylidene-, -vinylidene-, -cycloalkylidene-, or -arylidene-;
A is $—C(O)—$, $—C(S)—$, or $—CH_2—N(R_7)—$;
$D_1$, $D_2$, and $D_3$ are each independently $—N(R_6)—C$ if A is $—C(O)—$ or $C(S)—$, and $—C(=X_2)—E—N(R_7)—C$ if A is $—CH_2—N(R_7)—$; wherein E is a single bond, -alkylidene-, -vinylidene-, -cycloalkylidene-, or -arylidene- and $X_2$ is $=O$ or $=S$; and
each $—R_1$ to $—R_7$ of the compounds of formula VIIIa–VIIId is independently $—H$, -alkyl, -hydroxyalkyl, -alkoxy, -alkoxyalkyl, -cycloalkyl, or -aryl; each of which is optionally substituted,
or a pharmaceutically acceptable salt thereof.

7. The composition of claim 6 wherein $W_1$ of formula VIIa–VIId is a moiety of formula VIIIa, VIIIb, VIIIc or VIIId and $W_2$ of formula VIIa–VIId is $—OR'''$, $—SR'''$, $—NR'''R'''—CON(R_2)_2$, -glutamate, or -polyglutamate, wherein each $R'''$ is independently -aryl, -cycloalkyl, or -heterocyclo.

8. The composition of claim 6 wherein $W_2$ of formula VIIa–VIId is a moiety of formula VIIIa, VIIIb, VIIIc or VIIId; and $W_1$ of formula VIIa–VIId is $—OR'''$, $—SR'''$, $—NR'''R'''—CON(R_2)_2$, -glutamate, or -polyglutamate, wherein each $R'''$ is independently aryl, -cycloalkyl, or -heterocyclo.

9. The composition of claim 6 wherein both $W_1$ and $W_2$ of formula VIIa–VIId is a moiety of formula VIIIb, VIIIc or VIIId].

10. The composition of formula VIIa–VIId of claim 6 wherein $M_1$ is a radioactive-, paramagnetic- or superparamagnetic- metal and each $K_1$ is a macrocyclic metal chelating ligand radical of formula VI;

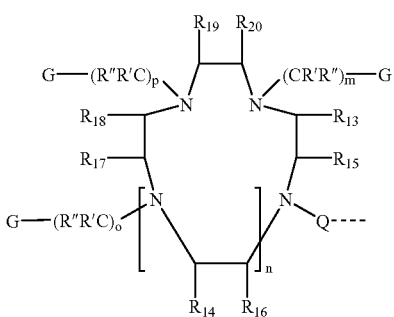

VI wherein said metal chelating radical is attached to the remainder of the compound of formulae VIIa–VIId via the free —N(R)— atom of the function —Q— if A is —C(O)— or —C(S)— or through the free —C(O)— atom of the function —Q— if A is —CH$_2$—N(R$_7$)—; wherein —Q— is —[C(R')(R'')]$_{s1}$—[C(t)(R$_{21}$)]$_{s2}$—[C(R$_{22}$)(R$_{23}$)]$_{s3}$—X3—Y—X4—; wherein s1, s2, s3, and s4 are independently 0 to 2;

X3, X4, X5, and X6 are independently a single bond, —O—, —S—, or —N(R$_{24}$)—;

Y is a single bond, —C(R$_{25}$)(R$_{26}$)—, or Y1, wherein Y1 is —C(=X5)—X6—W—, wherein W is a single bond, -alkylidene-, -cycloalkylidene-, -arylidene-, -alkenylidene-, or -alkynylidene-, whose carbon atoms are optionally substituted;

t is H, R$_{27}$, —C(O)OR$_{28}$, —P(O)(OR$_{29}$))OH, —P(O)(OR$_{30}$))OR$_{31}$, —P(O)(OR$_{32}$)R$_{33}$, —P(O)(OH)R$_{34}$, —C(O)N(R$_{35}$)(R$_{36}$), or C(O)NH(R$_{37}$);

each G is independently —C(O)OR''', —P(O)(OR''')OH, —P(O)(OR''')$_2$, —P(O)(OR''')R'', —P(O)(OH)R''C(O)N(R''')$_2$, or C(O)NH(R''');

each R' and R'' is independently a single bond, —H, -alkyl, -alkoxy, -cycloalkyl, -hydroxyalkyl, -aryl, or -heterocyclo, each of which is optionally substituted, each R''' is independently —H, -alkyl, -cycloalkyl, -hydroxyalkyl, -aryl, or -heterocyclo, each of which is optionally substituted, each —R$_{13}$ through —R$_{23}$, and —R$_{25}$ through —R$_{27}$ is independently —H, -alkyl, -alkoxy, -halogen, -hydroxy, -cycloalkyl, -hydroxyalkyl, -aryl, or -heterocyclo, each of which is optionally substituted;

each —R$_{24}$, and —R$_{28}$ through —R$_{37}$ is independently —H, -alkyl, -alkenyl, -cycloalkyl, -aryl, or a 5- or 6-membered nitrogen or oxygen containing heterocycle, each of which is optionally substituted;

or a pharmaceutically accepted salt thereof.

11. The composition of formula VIIa–VIId of claim 6 wherein M$_1$ is a radioactive metal and at least one —K$_1$ is a macrocyclic metal chelating ligand radical of formula V:

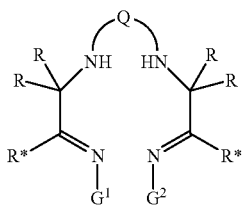

V wherein

—Q— is the group —(C(RR))$_{m1}$—(Y$^1$)$_n$—(C(RR))$_{m2}$—(Y$^2$—(C(RR))$_{m3}$)$_{n1}$;

Y$^1$ and Y$^2$ are each independently —CH$_2$—, —NR—, —O—, —S—, —SO—, —SO$_2$— or —Se—;

n and n1 are each independently 0 or 1; and m1, m2 and m3 are independently 0 or an integer from 1 to 4; provided that m1 and m2 are not both 0, that m1+m2+n+n1 is less than 6 and that a carbon atom bearing an R group is not directly bonded to more than one heteroatom;

each —R and —R* group is independently: —R$^4$; -alkoxy; -hydroxy; -halogen, especially fluoro, -haloalkyl, —OR$^5$, —C(O)—R$^5$, —C(O)—N(R$^5$)$_2$, —N(R$^5$)$_2$, —N(R$^5$)—COR$^5$, -alkyl-C(O)—OR$^5$, -alkyl-C(O)—N(R$^5$)$_2$, -alkyl-N(R$^5$)$_2$—, -alkyl-N(R$^5$)—COR$^5$, -aryl-C(O)—OR$^5$, -aryl-C(O)—N(R$^5$)$_2$, -aryl-N(R$^5$)$_2$—, -aryl-N(R$^5$)—COR$^5$, -nitrile, -acyl, -acyloxy, -heterocyclo, -hydroxyalkyl, -alkoxyalkyl, -hydroxyaryl, arylalkyl, —SO$_2$—R$^5$, -alkyl-SO$_2$—R$^5$, or —[R$^3$]—; wherein —[R$^3$]— is a linking group —[(A)p]— that links the metal chelating ligand radical of formula V to the remainder of the molecule of formulae VIIa through VIId;

wherein —[(A)p]— comprises a straight or branched chain of individual moieties that are the same or different and selected from the group consisting of: —CH$_2$—, —CHR$_3$—, —CR$_4$R$_5$—, —CH=CH—, —CH=CR$_6$—, >CR$_7$—CR$_8$<, —C=C—, —CR$_9$=CR$_{10}$—, —C≡C—, -cycloalkylidene-, -cycloalkenyl-, -arylidene-, -heterocyclo-, carbonyl (—CO—), —O—, —S—, —NH—, —HC=N—, —CR$_{11}$=N—, —NR$_{12}$—, (—CS—),

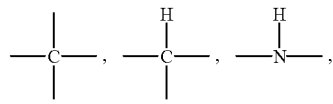

and p is an integer from 0 to 24;

each —R$^4$ and —R$^3$ through —R$^5$ is independently —H, -alkyl, -alkoxy, -hydroxy, -cycloalkyl, -hydroxyalkyl, -aryl, or -heterocyclo, each of which is optionally substituted;

each —R$^5$ and —R$^6$ through —R$^{12}$ is independently —H, -alkyl, -aryl, -cycloalkyl or -hydroxyalkyl, each of which is independently substituted; or two R groups, or an R group and an R* group, taken together with the one or more atoms to which they are bonded, form a saturated or unsaturated, spiro or fused, carbocyclic or heterocyclic ring which is optionally substituted by one or more R or R* groups;

each —G$^1$ and —G$^2$ is independently —OH or —(NR$^6$)$_2$; with the proviso that at least one of —G$^1$ or —G$^2$ is —(NR$^6$)$_2$, and each —R$^6$ is independently -hydrogen, -alkyl, -aryl, -acyl or —[R$^3$]—;

with the proviso that at least one —R , —R*, or —R$^6$ group is —[R$^3$]—;

or a pharmaceutically acceptable salt thereof.

12. The composition of formula VIIa–VIId of claim 6 wherein M$_1$ is a radioactive isotope and at least one K$_1$ is a macrocyclic metal chelating ligand of formula IIIa–IIIc:

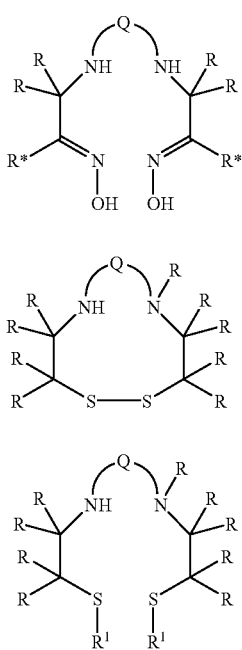

IIIa

IIIb

IIIc wherein

Q is the group —(C(RR))$_{m1}$—Y$^1$(C(RR))$_{m2}$—(Y$^2$(C(RR))$_{m3}$)$_n$—, wherein
Y$^1$ and Y$^2$ are independently —CH$_2$—, —NR—, —O—, —S—, —SO—, —SO$_2$— or —Se—;
n is 0 or 1; and m1, m2 and m3 are integers from 0 to 4, provided that the sum of m1 and m2 is greater than zero;

all R and R* groups are independently —R$^4$, —Cl, —F, —Br, —OR$^5$, —COOR$^5$, —CON(R$^5$)$_2$, —N(R$^5$)$_2$, -alkyl-COOR$^5$, -alkyl-C(O)—N(R$^5$)$_2$, -alkyl-N(R$^5$)$_2$, —C(O)OR$^5$, —C(O)N(R$^5$)$_2$, -aryl-N(R$^5$)$_2$, -acyl, -acyloxy, -heterocyclo, -hydroxyalkyl, —SO$_2$—R$^5$, -alkyl-SO$_2$—R$^5$, or —[R$^3$]—; wherein —[R$^3$]— is a linking group —[(A)p]— that links the metal chelating ligand of formula IIIa, IIIb, or IIIc to the remainder of the molecule; wherein —[(A)p]— comprises a straight or branched chain of individual moieties that are the same or different and selected from the group consisting of: —CH$_2$—, —CHR$_3$—, —CR$_4$R$_5$—, —CH═CH—, —CH═CR$_6$—, >CR$_7$—CR$_8$<, —C═C—, —CR$_9$═CR$_{10}$—, —C≡C—, -cycloalkylidene-, -cycloalkenyl-, -arylidene-, -heterocyclo-, carbonyl —(CO)—, —O—, —S—, —NH—, —HC═N—, —CR$_{11}$═N—, —NR$_{12}$—, —(CS)—

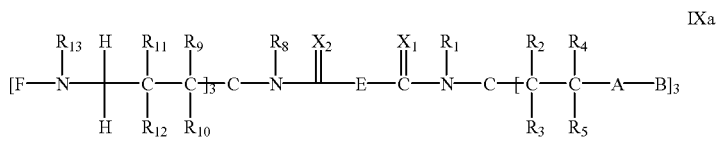

and p is an integer from 0 to 24;

each —R$^4$ and —R$_3$ through —R$_5$ is independently —H, -alkyl, -alkoxy, -hydroxy, -cycloalkyl, -hydroxyalkyl, -aryl, or -heterocyclo, each of which is optionally substituted;

each —R$^5$ and —R$_6$ through —R$_{12}$ is independently —H, -alkyl, -aryl, -cycloalkyl or -hydroxyalkyl, each of which is independently substituted;

with the provisos that a carbon atom bearing an —R group is not directly bonded to more than one heteroatom; and that at least one —R or —R* group on —K$_1$ is —[R$^3$]— or a pharmaceutically acceptable salt thereof.

13. A folate-receptor binding ligand comprising dendrimeric first-, second-, third-, and fourth- generation conjugates containing one or more folate-receptor binding moieties coupled to one or more macrocyclic metal-chelating ligand radicals for detection outside the body by imaging means for diagnosis or for providing a therapeutic or radiotherapeutic effect, wherein said folate-receptor binding ligands have the structure of formulae IXa, IXb, IXc, and IXd, representing dendrimers of generations 1, 2, 3, and 4, respectively, wherein for the first generation dendrimers of formula IXa, bearing three folate and three metal chelating ligand radicals;

IXa

[F—N(H)—C(R$_{13}$)(H)—C(R$_{11}$)(R$_{12}$)—C(R$_9$)(R$_{10}$)—$]_3$C—N(X$_2$)—E—C(X$_1$)—N(R$_1$)—C(R$_2$)(R$_3$)—C(R$_4$)(R$_5$)—A—B]$_3$

F is a folate-receptor binding moiety of formula:

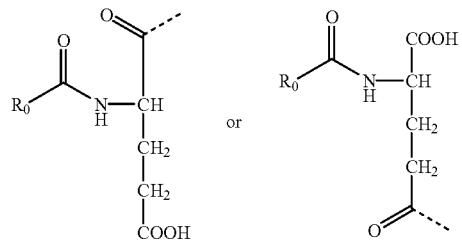

wherein R$_0$ is a moiety of formula:

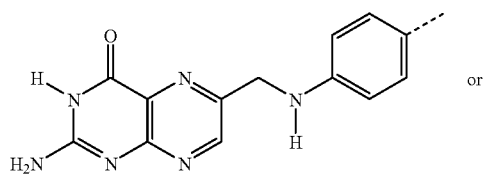

or

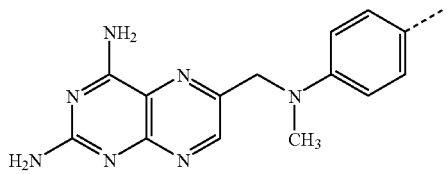

each $X_1$ through $X_4$ is independently $=$O or $=$S;

each A is —C(O)—, —C(S)—, or —CH$_2$—N(R$_7$)—;

E is a single bond, -alkylidene-, -vinylidene-, -cycloalkylidene-, or -arylidene-;

B is a macrocyclic metal-chelating ligand radical that is attached to A via an amide or thioamide bond and is optionally chelated to a paramagnetic, superparamagnetic, radioactive or non-radioactive metal;

—$R_1$, —$R_6$ through —$R_8$, —$R_{13}$, and —$R_{14}$ are independently —H, -alkyl, -hydroxyalkyl, -cycloalkyl, or -aryl;

—$R_2$ through —$R_5$ and —$R_9$ through —$R_{12}$ are independently —H, -alkyl, -hydroxyalkyl, -alkoxy, -hydroxyalkyl, -halogen, -cycloalkyl, -aryl or -heterocyclo;

or a pharmaceutically accepted salt thereof;

and wherein for the second generation dendrimeric compounds of formula IXb, bearing nine folate-receptor binding moieties and nine metal-chelating ligand radicals:

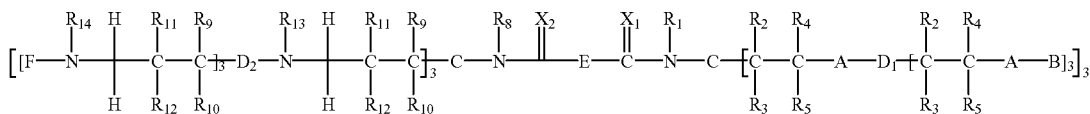

IXb

A, B, E, F, $X_1$ through $X_4$ and all —R groups are as defined for the compounds of formula IXa;

$D_1$ and $D_2$ are independently —N(R$_6$)—C if A is —C(O)— or —C(S)—, and —C($=$X$_3$)—E—N(R$_7$)—C if A is —CH$_2$—N(R$_7$)—;

and wherein for the third generation dendrimeric compounds of formula IXc, bearing 27 folate receptor binding moieties and 27 metal chelating ligand radicals:

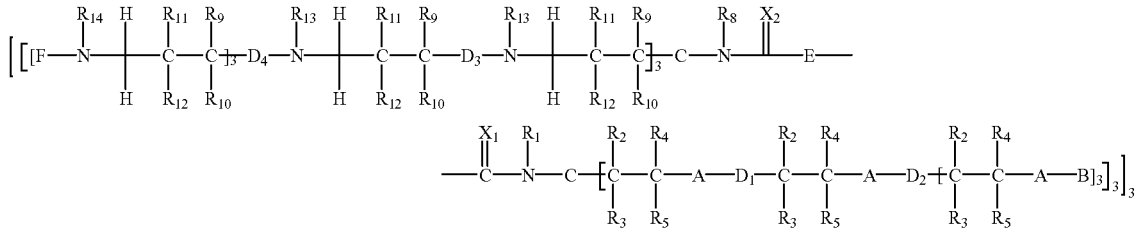

IXc $D_1$, $D_2$, $D_3$, and $D_4$ are independently —N(R$_6$)—C if A is —C(O)— or —C(S)—, and —C($=$X$_3$)—E—N(R$_7$)—C if A is —CH$_2$—N(R$_7$)—; and all other groups are defined as above;

and wherein for the fourth generation dendrimeric compounds of formula IXd, bearing 81 folate receptor binding moieties to 81 metal chelating ligands:

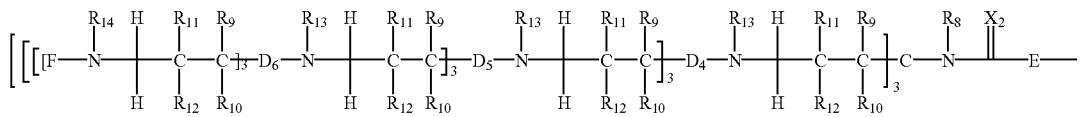

IXd

-continued

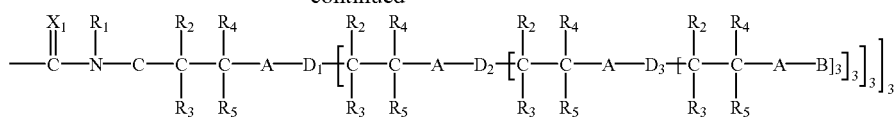

$D_1$, $D_2$, $D_3$, $D_4$, $D_5$, and $D_6$ are each independently —N($R_6$)—C if A is —C(O)— or —C(S)—, and —C(=$X_3$)—E—N(R7)—C if A is —CH$_2$—N($R_7$)—;

or a pharmaceutically acceptable salt thereof.

14. The folate-receptor binding ligand of claim 13 wherein F of formulae IXb, IXc, and IXd is a folate-receptor binding moiety of formula:

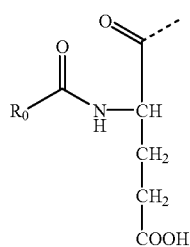

wherein $R_0$ is a moiety of formula:

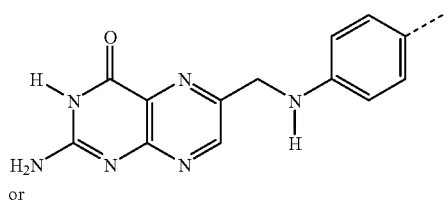

or

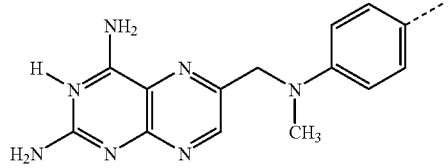

or a pharmaceutically acceptable salt thereof.

15. The folate-receptor binding ligand of claim 13 wherein F of formulae IXb, IXc, and IXd is a folate receptor binding moiety of formula:

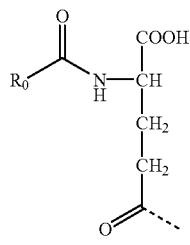

wherein $R_0$ is a moiety of formula:

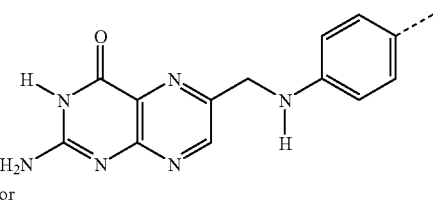

or

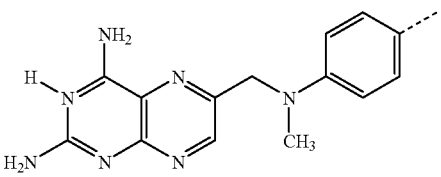

or a pharmaceutically acceptable salt thereof.

16. The folate receptor binding ligand of formulae IXb, IXc, and IXd of claim 13, wherein B is a polyaza macrocyclic ligand radical of formula VIc that is optionally chelated to a paramagnetic, superparamagnetic, radioactive or non-radioactive metal,

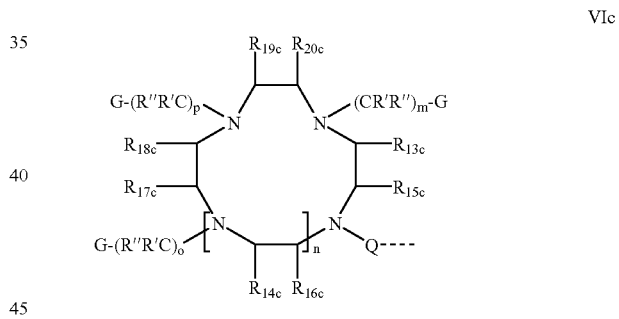

VIc wherein said macrocyclic ligand radical is attached to A via an amide or thioamide linkage through a free —C(O)— group of the function —Q— if A is —CH$_2$—N($R_7$)—;
—Q— is —[C(R')(R")]$_{s1}$—C(t)($R_{21}$)]$_{s2}$—[C($R_{22}$)($R_{23}$)]$_{s3}$—$X_3$—Y—$X_4$—; wherein
s1, s2, s3, and s4 are independently 0 to 2;
—$X_3$, —$X_4$, —$X_5$, and —$X_6$ are independently a single bond, —O—, —S—, or —N($R_{24}$)—;
Y is a single bond, —C($R_{25}$)($R_{26}$)—, or Y1,
wherein Y1 is —C(=$X_5$)—$X_6$—W—, wherein
W is a single bond, -alkylidene-, -cycloalkylidene-, arylidene-, -alkenylidene-, or -alkynylidene-, whose carbon atoms are optionally substituted;
t is H, $R_{27}$, —C(O)O$R_{28}$, —P(O)(O$R_{29}$)OH, —P(O)(O$R_{30}$))O$R_{31}$, —P(O)(O$R_{32}$)$R_{33}$, —P(O)(OH)$R_{34}$, —C(O)N($R_{35}$)($R_{36}$), or C(O)NH($R_{37}$);
each G is independently —C(O)OR''', —P(O)(OR''')OH, —P(O)(OR''')$_2$, —P(O)(OR''')R'', —P(O)(OH)R''—C(O)N(R''')$_2$, or —C(O)NH(R''');

each —R' and —R" is independently a single bond, —H, -alkyl, -alkoxy, -cycloalkyl, -hydroxyalkyl, -aryl, or -heterocyclo, each of which is optionally substituted, each —R'" is independently —H, -alkyl, -cycloalkyl, -hydroxyalkyl, -aryl, or -heterocyclo, each of which is optionally substituted, each —$R_{13c}$ through —$R_{20c}$, —$R_{21}$ through —$R_{23}$, and —$R_{25}$ through —$R_{27}$ is independently —H, -alkyl, -alkoxy, -halogen, -hydroxy, -cycloalkyl, -hydroxyalkyl, -aryl, or -heterocyclo, each of which is optionally substituted;

each —$R_{24}$, and —$R_{28}$ through —$R_{37}$ is independently —H, -alkyl, -alkenyl, -cycloalkyl, -aryl, a 5- or 6-membered nitrogen or oxygen-containing heterocycle, each of which is optionally substituted;

or a pharmaceutically accepted salt thereof.

17. The folate-receptor binding ligand of formulae IXa, IXb, IXc, and IXd of claim 13 wherein B is a metal-chelating ligand radical of formula IIIa–IIIc that is optionally chelated to a paramagnetic, superparamagnetic, radioactive or non-radioactive metal:

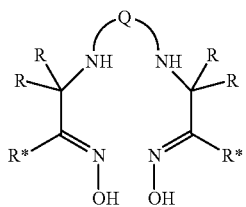

IIIa

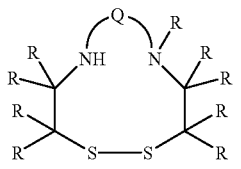

IIIb

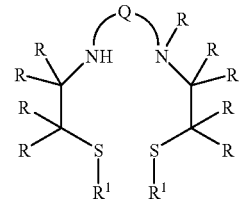

IIIc wherein

Q is the group —$(C(RR))_{m1}$—$Y^1(C(RR))_{m2}$—$(Y^2$—$(C(RR))_{m3})_n$—, wherein $Y^1$ and $Y^2$ are independently —$CH_2$—, —NR—, —O—, —S—, —SO—, —$SO_2$— or —Se—;

n is 0 or 1; and m1, m2 and m3 are integers from 0 to 4, provided that the sum of m1 and m2 is greater than zero;

all R and R* groups are independently —$R^4$, —Cl, —F, —Br, —$OR^5$, —$COOR^5$, —$CON(R^5)_2$, —$N(R^5)_2$, -alkyl-$COOR^5$, -alkyl-C(O)—$N(R^5)_2$, -alkyl-$N(R^5)_2$, —$C(O)OR^5$, —$C(O)N(R^5)_2$, -aryl-$N(R^5)_2$, acyl, acyloxy, heterocyclo, hydroxyalkyl, —$SO_2$—$R^5$, -alkyl-$SO_2$—$R^5$, or —$[R^3]$—;

wherein —$[R^3]$— is a linking group —$[(A)p]$— that couples the metal chelating radical of formula IIIa, IIIb, or IIIc to the remainder of the molecule;

—$[(A)p]$— comprises a straight or branched chain of individual moieties that are the same or different and selected from the group consisting of; —$CH_2$—, —$CHR_3$—, —$CR_4R_5$—, —CH=CH—, —CH=$CR_6$—, >$CR_7$—$CR_8$<, —C≡C—, —$CR_9$=$CR_{10}$—, —C≡C—, -cycloalkylidene-, -cycloalkenyl-, -arylidene-, -heterocyclo-, carbonyl —(CO)—, —O—, —S—, —NH—, —HC=N—, —$CR_{11}$=N—, —$NR_{12}$—, —CS—, and

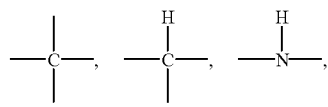

and p is an integer from 0 to 24;

each —$R^4$ and —$R_3$ through —$R_5$ is independently —H, -alkyl, -alkoxy, -hydroxy, -cycloalkyl, -hydroxyalkyl, -aryl, or -heterocyclo, each of which is optionally substituted;

each —$R^5$ and —$R_6$ through —$R_{12}$ is independently —H, -alkyl, -aryl, -cycloalkyl or -hydroxyalkyl, each of which is independently substituted;

with the provisos that a carbon atom bearing an —R group is not directly bonded to more than one heteroatom; and that at least one —R or —R* group on the metal chelating radical —$K_1$ of formulae IIIa, IIIb, or IIIc is —$[R^3]$—;

or a pharmaceutically acceptable salt thereof.

18. The folate-receptor binding ligand of formulae IXa, IXb, IXc, and IXd of claim 13, wherein B is a metal-chelating ligand radical of formula V that is optionally chelated to a paramagnetic, superparamagnetic, radioactive or non-radioactive metal:

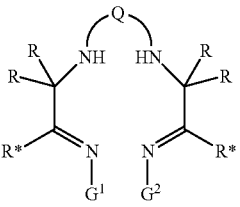

V wherein

—Q— is the group —$(C(RR))_{m1}$—$(Y^1)_n$—$(C(RR))_{m2}$—$(Y^2$—$(C(RR))_{m3})_{n1}$;

$Y^1$ and $Y^2$ are each independently —$CH_2$—, —NR—, —O—, —S—, —SO—, —$SO_2$— or —Se—;

n and n1 are each independently 0 or 1; and m1, m2 and m3 are 0 or an integer from 1 to 4; provided that m1 and m2 are not both 0, that m1+m2+n+n1 is less than 6 and that a carbon atom bearing an R group is not directly bonded to more than one heteroatom;

each —R and —R* group is independently: —$R^4$; -alkoxy; -hydroxy; -halogen, -haloalkyl, —$OR^5$, —C(O)—$R^5$, —C(O)—$N(R^5)_2$, —$N(R^5)_2$, —$N(R^5)$—$COR^5$, -alkyl-C(O)—$OR^5$, -alkyl-C(O)—$N(R^5)_2$, -alkyl-$N(R^5)_2$—, -alkyl-$N(R^5)$—$COR^5$, -aryl-C(O)—$OR^5$, -aryl-C(O)—$N(R^5)_2$, aryl-$N(R^5)_2$—, -aryl-N($R^5$)—$COR^5$, -nitrile, -acyl, -acyloxy, -heterocyclo, -hydroxyalkyl, -alkoxyalkyl, -hydroxyaryl, arylalkyl, —SO$_2$—R$^5$, -alkyl-SO$_2$—R$^5$, or —[R$^3$]—; wherein —[R$^3$]— is a linking group —[(A)p]— that links the metal chelating ligand radical of formula V to the remainder of the molecule of formulae IXa, IXb, IXc, and IXd;

wherein —[(A)p]— comprises a straight or branched chain of individual moieties that are the same or different and are selected from the group consisting of: —CH$_2$—, —CHR$_3$—, —CR$_4$R$_5$—, —CH=CH—, —CH=CR$_6$—, >CR$_7$—CR$_8$<, —C=C—, —CR$_9$=CR$_{10}$—, —C≡C—, -cycloalkylidene-, -cycloalkenyl-, -arylidene-, -heterocyclo-, carbonyl (—CO—), —O—, —S—, —NH—, —HC=N—, —CR$_{11}$=N—, —NR$_{12}$—, —CS—),

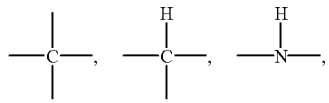

and p is an integer from 0 to 24;
each —R$^4$ and —R$_3$ through —R$_5$ is independently —H, -alkyl, -alkoxy, -hydroxy, -cycloalkyl, -hydroxyalkyl, -aryl, or -heterocyclo, each of which is optionally substituted;
each —R$^5$ and —R$_6$ through —R$_{12}$ is independently —H, -alkyl, -aryl, -cycloalkyl or -hydroxyalkyl, each of which is independently substituted; or
two R groups, or an R group and an R* group, taken together with the one or more atoms to which they are bonded, form a saturated or unsaturated, spiro or fused, carbocyclic or heterocyclic ring which may be unsubstituted or substituted by one or more groups of R or R*;
each —G$^1$ and —G$^2$ is independently —OH or —(NR$^6$)$_2$; with the proviso that at least one of —G$^1$ or —G$^2$ is —(NR$^6$)$_2$, and each —R$^6$ is independently -hydrogen, -alkyl, -aryl, -acyl or —[R$^3$]—;
with the provisos that a carbon atom bearing an —R group is not directly bonded to more than one heteroatom and that at least one —R , —R*, or —R$^6$ group on the metal chelating radical —K$_1$ of formula V is —[R$^3$]—;
or a pharmaceutically acceptable salt thereof.

19. The composition of claim 6 wherein W$_1$, W$_2$ or both W$_1$ and W$_2$ contain metal chelating ligands of formula V that are chelated to a radioactive metal:

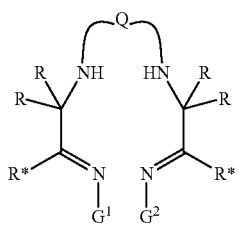

V wherein
Q is the group —(C(RR))$_{m1}$—(Y$^1$)$_n$—(C(RR))$_{m2}$—(Y$^2$—(C(RR))$_{m3}$)$_{n1}$;
Y$^1$ and Y$^2$ are each independently —CH$_2$—, —NR—, —O—, —S—, —SO—, —SO$_2$— or —Se—;
n and n1 are each independently 0 or 1; and m1, m2 and m3 are independently 0 or an integer from 1 to 4;
provided that m1 and m2 are not both 0, that m1+m2+n+n1 is less than 6 and that a carbon atom bearing an R group is not directly bonded to more than one heteroatom;
each R and R* group is independently: —H, —R$^4$; -alkoxy; -hydroxy; -halogen, especially fluoro, -haloalkyl, —OR$^5$, —C(O)—R$^5$, —C(O)—N(R$^5$)$_2$, —N(R$^5$)$_2$, —N(R$^5$)—COR$^5$, -alkyl-C(O)—OR$^5$, -alkyl-C(O)—N(R$^5$)$_2$, -alkyl-N(R$^5$)$_2$—, -alkyl-N(R$^5$)—COR$^5$, -aryl-C(O)—OR$^5$, -aryl-C(O)—N(R$^5$)$_2$, aryl-N(R$^5$)$_2$—, -aryl-N(R$^5$)—COR$^5$, -nitrile, -acyl, -acyloxy, -heterocyclo, -hydroxyalkyl, -alkoxyalkyl, -hydroxyaryl, -arylalkyl, —SO$_2$—R$^5$, -alkyl-SO$_2$—R$^5$, or —[R$^3$]—;
wherein
each —[R$^3$]— is, in its entirety, the linking group —[(A)p*]— that serves to couple the metal chelating ligand radical —K$_5$ to —X—;
each —R$^4$ is independently —H, -alkyl, -alkoxy, -hydroxy, -cycloalkyl, -hydroxyalkyl, -aryl, or -heterocyclo, each of which is optionally substituted;
each —R$^5$ is independently —H, -alkyl, -aryl, -cycloalkyl or -hydroxyalkyl, each of which is independently substituted; or
two R groups, or an R group and an R* group, taken together with the one or more atoms to which they are bonded, form a saturated or unsaturated, spiro or fused, carbocyclic (such as fused 1,2-phenyl) or heterocyclic ring which may be unsubstituted or substituted by one or more groups R or R* groups above;
each —G$^1$ and —G$^2$ is independently —OH or —(NR$^6$)$_2$; with the proviso that at least one of —G$^1$ or —G$^2$ is —(NR$^6$)$_2$, where each —R$^6$ is independently -hydrogen, -alkyl, -aryl, -acyl or —[R$^3$]—; and
A is a linking group; and p is 0 or a positive integer;
with the proviso that at one to three —R, —R*, or —R$^6$ groups is —[R$^3$]—;
or a pharmaceutically acceptable salt thereof.

20. The composition of claim 6 wherein W$_1$, W$_2$ or both W$_1$ and W$_2$ contain metal chelating ligands of formula V that are chelated to a radioactive metal:

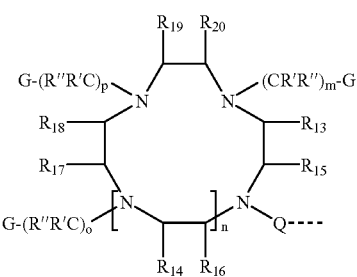

VI wherein
n is 0;
each m, o, and p is independently 1 or 2;
Q is —[C(R')(R")]$_{s1}$—[C(t)(R$_{21}$)]$_{s2}$——[C(R$_{22}$)(R$_{23}$)]$_{s3}$—X3—Y—X4—;
wherein
s1, s2, s3, and s4 are independently 0 to 2;
X3, X4, X5 and X6 are independently a single bond, —O—, —S—, or —N(R$_{24}$)—;
Y is a —C(R$_{25}$)(R$_{26}$)—, or Y1 wherein Y1 is —C(=X5)—X6—W—, wherein W is a single bond, -alkylidene-, -cycloalkylidene-, -arylidene-, -alkenylidene-, or -alkynylidene-, whose carbon atoms may or may not be substituted;

t is H, $R_{27}$, —C(O)OR$_{28}$, —P(O)(OR$_{29}$))OH, —P(O)(OR$_{30}$))OR$_{31}$, —P(O)(OR$_{32}$)R$_{33}$, —P(O)(OH)R$_{34}$—C(O)N(R$^{35}$)(R$_{36}$), or C(O)NH(R$_{37}$);

each G is independently —C(O)OR''', —P(O)(OR''')OH, —P(O)(OR''')$_2$, —P(O)(OR''')R'', —P(O)(OH)R''C(O)N(R''')$_2$, or C(O)NH(R''');

each —R' and —R" is independently a single bond, —H, -alkyl, -alkoxy, -cycloalkyl, hydroxyalkyl, -aryl, or -heterocyclo, each of which is optionally substituted, each —R''' is independently a —H, -alkyl, -cycloalkyl, -hydroxyalkyl, -aryl, or -heterocyclo, each of which is optionally substituted;

each —$R_{13}$ through —$R_{23}$, and —$R_{24}$, through —$R_{27}$ is independently —H, -alkyl, -alkoxy, -halogen, -hydroxy, -cycloalkyl, -hydroxyalkyl, aryl, or -heterocyclo, each of which is optionally substituted;

each —$R_{24}$, and —$R_{28}$ through —$R_{37}$ is independently —H, -alkyl, -alkenyl, -cycloalkyl, -aryl, a 5- or 6-membered nitrogen or oxygen containing heterocycle, each of which is optionally substituted;

or $R_{13}$ together with $R_{15}$, and $R_{17}$ together with $R_{18}$, independently form, together with the carbon atoms in the poly-aza macrocycle to which they are attached, a fused fully or partially saturated non-aromatic cyclohexyl ring which may be unsubstituted or substituted by one or more halogen, alkyl, ether, hydroxy, or hydroxyalkyl groups, and which may be further fused to a carbocyclic ring, or $R_{13}$ and $R_{15}$ are each hydrogen and $R_{17}$, together with $R_{18}$, forms a fused fully or partially saturated non-aromatic cyclohexyl ring as defined above, or $R_{13}$, together with $R_{15}$, forms a fused fully or partially saturated non-aromatic cyclohexyl ring and $R_{17}$ and $R_{18}$ are hydrogen;

or a pharmaceutically acceptable salt thereof.

\* \* \* \* \*